(12) United States Patent
Corbau et al.

(10) Patent No.: US 7,141,585 B2
(45) Date of Patent: Nov. 28, 2006

(54) PYRAZOLE DERIVATIVES

(75) Inventors: Romuald Gaston Corbau, Sandwich (GB); Charles Eric Mowbray, County of Kent (GB); Manoussos Perros, Sandwich (GB); Paul Anthony Stupple, Sandwich (GB); Anthony Wood, Sandwich (GB)

(73) Assignee: Agouron Pharmaceuticals, Inc., San Diego, CA (US)

( * ) Notice: Subject to any disclaimer, the term of this patent is extended or adjusted under 35 U.S.C. 154(b) by 271 days.

(21) Appl. No.: 10/832,920

(22) Filed: Apr. 26, 2004

(65) Prior Publication Data

US 2004/0209862 A1    Oct. 21, 2004

Related U.S. Application Data

(62) Division of application No. 09/899,322, filed on Jul. 5, 2001, now Pat. No. 6,750,230.

(60) Provisional application No. 60/220,087, filed on Jul. 21, 2000.

(30) Foreign Application Priority Data

Jul. 7, 2000    (GB)    .................. 0016787.4

(51) Int. Cl.
*A61K 31/435*    (2006.01)

(52) U.S. Cl. .................... 514/326; 514/341; 514/406; 514/407; 546/407; 546/211; 546/275.7; 548/376.1

(58) Field of Classification Search ................ 514/326, 514/341, 406, 407; 548/376.1
See application file for complete search history.

(56) References Cited

FOREIGN PATENT DOCUMENTS

| | | |
|---|---|---|
| AU | 4227585 | 5/1985 |
| AU | 664686 | 12/1985 |
| AU | 7980087 | 10/1986 |
| CA | 2163174 | 5/1996 |
| CA | 2163175 | 5/1996 |
| DE | 2829289 | 1/1980 |
| DE | 3520330 | 12/1986 |
| DE | 3603291 | 8/1987 |
| DE | 3617554 | 11/1987 |
| DE | 3711928 | 10/1988 |
| DE | 4023488 | 1/1992 |
| DE | 4333659 | 4/1995 |
| DE | 4411235 | 10/1995 |
| DE | 19518054 | 9/1996 |
| DE | 19521822 | 12/1996 |
| DE | 19622189 | 12/1997 |
| DE | 19629826 | 1/1998 |
| DE | 19827855 | 12/1999 |
| DE | 19829616 | 1/2000 |
| DE | 19837067 | 2/2000 |
| EP | 0129846 | 6/1984 |
| EP | 0201852 | 5/1986 |
| EP | 0203428 | 5/1986 |
| EP | 0272704 | 12/1987 |
| EP | 0301339 | 7/1988 |
| EP | 0329326 | 2/1989 |
| EP | 0556396 | 11/1991 |
| EP | 0627423 | 1/1993 |
| EP | 0658547 | 12/1994 |
| EP | 0691128 | 6/1995 |
| EP | 0786455 | 9/1995 |
| EP | 0846686 | 6/1998 |
| EP | 0890573 | 1/1999 |
| EP | 0959074 | 11/1999 |
| EP | 1072597 | 1/2001 |
| FR | 2745467 | 9/1997 |
| FR | 2795726 | 1/2000 |
| GB | 2224208 | 5/1990 |
| GB | 2265900 | 10/1993 |
| GB | 2310207 | 8/1997 |
| JP | 50030871 | 7/1973 |
| JP | 55033413 | 3/1980 |
| JP | 55035035 | 3/1980 |
| JP | 55035036 | 3/1980 |
| JP | 55035037 | 3/1980 |
| JP | 55035038 | 3/1980 |
| JP | 55035039 | 3/1980 |
| JP | 55047602 | 4/1980 |
| JP | 57007403 | 1/1982 |

(Continued)

OTHER PUBLICATIONS

Genin, et al.; Novel 1,5-Diphenylpyrazole Nonnucleoside HIV-1 Reverse Transcriptase Inhibitors with Enhanced Activity versus the Delavirdine-Resistant P236L Mutant: Lead Identification and SAR of 3- and 4-Substituted Derivatives; J. Med. Chem.; 43:1034-1040 (2000).

*Primary Examiner*—Kamal A. Saeed
(74) *Attorney, Agent, or Firm*—Keith D. Hutchinson; Bryan C. Zielinski

(57) ABSTRACT

This invention relates to the use of pyrazole derivatives of the formula

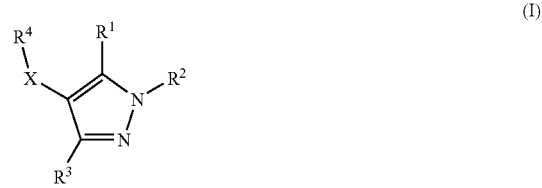

(I)

and pharmaceutically acceptable salts and solvates thereof, in the manufacture of a reverse transcriptase inhibitor or modulator, to certain novel such pyrazole derivatives and to processes for the preparation of and compositions containing such novel derivatives.

27 Claims, No Drawings

FOREIGN PATENT DOCUMENTS

| | | |
|---|---|---|
| JP | 58188858 | 4/1983 |
| JP | 59088470 | 5/1984 |
| JP | 59104362 | 6/1984 |
| JP | 59122472 | 7/1984 |
| JP | 59196869 | 11/1984 |
| JP | 60008204 | 1/1985 |
| JP | 60008207 | 1/1985 |
| JP | 60008208 | 1/1985 |
| JP | 60016974 | 1/1985 |
| JP | 60034902 | 2/1985 |
| JP | 60064903 | 4/1985 |
| JP | 60197605 | 10/1985 |
| JP | 60202803 | 10/1985 |
| JP | 61015802 | 1/1986 |
| JP | 61148105 | 7/1986 |
| JP | 62135401 | 6/1987 |
| JP | 62145003 | 6/1987 |
| JP | 63051304 | 3/1988 |
| JP | 6413072 | 1/1989 |
| JP | 1086464 | 3/1989 |
| JP | 1113304 | 5/1989 |
| JP | 1210003 | 8/1989 |
| JP | 1210084 | 8/1989 |
| JP | 2096472 | 4/1990 |
| JP | 3170374 | 7/1991 |
| JP | 5017470 | 1/1993 |
| JP | 5262741 | 10/1993 |
| JP | 6009317 | 1/1994 |
| JP | 6025177 | 2/1994 |
| JP | 6065237 | 3/1994 |
| JP | 6239864 | 8/1994 |
| JP | 7165724 | 6/1995 |
| JP | 7224041 | 8/1995 |
| JP | 7267931 | 10/1995 |
| JP | 8183787 | 1/1996 |
| JP | 8208620 | 8/1996 |
| JP | 9095482 | 4/1997 |
| JP | 11228312 | 8/1999 |
| JP | 00053649 | 2/2000 |
| NL | 7508706 | 6/1976 |
| RU | 657745 | 4/1979 |
| SU | 1545545 | 12/1993 |
| WO | 9211761 | 7/1992 |
| WO | 9313069 | 7/1993 |
| WO | 9317010 | 9/1993 |
| WO | 9413643 | 6/1994 |
| WO | 9413644 | 6/1994 |
| WO | 9413661 | 6/1994 |
| WO | 9422830 | 10/1994 |
| WO | 9531438 | 11/1995 |
| WO | 9531452 | 11/1995 |
| WO | 9533727 | 12/1995 |
| WO | 9640704 | 12/1996 |
| WO | 9721682 | 6/1997 |
| WO | 9726875 | 7/1997 |
| WO | 9840358 | 9/1998 |
| WO | 9850379 | 11/1998 |
| WO | 9852937 | 11/1998 |
| WO | 9856377 | 12/1998 |
| WO | 9923091 | 5/1999 |
| WO | 9932111 | 7/1999 |
| WO | 9951580 | 10/1999 |
| WO | 9957101 | 11/1999 |
| WO | 9958523 | 11/1999 |
| WO | 9962513 | 12/1999 |
| WO | 9964415 | 12/1999 |
| WO | 9967235 | 12/1999 |
| WO | 0007996 | 2/2000 |
| WO | 0066562 | 11/2000 |
| WO | 0069849 | 11/2000 |

PYRAZOLE DERIVATIVES

CROSS-REFERENCE TO RELATED APPLICATIONS

This application is a Divisional of prior application Ser. No. 09/899,322, filed Jul. 5, 2001 now U.S. Pat. No. 6,750,230, which claims the benefit of U.S. Provisional Application Ser. No. 60/220,087 filed Jul. 21, 2000, and U.K. Patent Application No. 0016787.4, filed Jul. 7, 2000, which are both hereby incorporated by reference in their entirety.

This invention relates to the use of pyrazole derivatives in the manufacture of a reverse transcriptase inhibitor or modulator, to certain novel such pyrazole derivatives and to processes for the preparation of and compositions containing such novel derivatives.

The present pyrazole derivatives bind to the enzyme reverse transcriptase and are modulators, especially inhibitors thereof. Reverse transcriptase is implicated in the infectious lifecycle of HIV, and compounds which interfere with the function of this enzyme have shown utility in the treatment of conditions including AIDS. There is a constant need to provide new and better modulators, especially inhibitors, of HIV reverse transcriptase since the virus is able to mutate, becoming resistant to their effects.

The present pyrazole derivatives are useful in the treatment of a variety of disorders including those in which reverse transcriptase is implicated. Disorders of interest include those caused by Human Immunodificiency Virus (HIV) and genetically related retroviruses, such as Acquired Immune Deficiency Syndrome (AIDS).

European Patent Application EP 0 786 455 A1 discloses a class of imidazole compounds which inhibit the growth of HIV. A class of N-phenylpyrazoles which act as reverse transcriptase inhibitors are disclosed in *J. Med. Chem.*, 2000, 43, 1034. Antiviral activity is ascribed to a class of N-(hydroxyethyl)pyrazole derivatives in U.S. Pat. No. 3,303,200.

According to the present invention there is provided the use of a compound of the formula

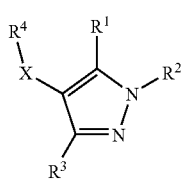

(I)

or a pharmaceutically acceptable salt or solvate thereof, wherein either (i) $R^1$ is H, $C_1$–$C_6$ alkyl, $C_3$–$C_7$ cycloalkyl, phenyl, benzyl, halo, —CN, —$OR^7$, —$OR^8$, —$CO_2R^5$, —$CONR^5R^5$, —$OCONR^5R^5$, —$NR^5CO_2R^7$, —$NR^5R^5$, —$NR^5COR^5$, —$NR^5CO$—($C_1$–$C_8$ alkylene)-$OR^5$, —$NR^5CONR^5R^5$, —$NR^5SO_2R^7$ or $R^6$, said $C_1$–$C_6$ alkyl $C_3$–$C_7$ cycloalkyl, phenyl and benzyl being optionally substituted by halo, —CN, —$OR^5$, —$OR^8$, —$CO_2R^5$, —$CONR^5R^5$, —$OCONR^5R^5$, —$NR^5CO_2R^7$, —$NR^5R^5$, —$NR^8R^9$, —$NR^5COR^5$, —$NR^5COR^6$, —$NR^5COR^8$, —$SO_2NR^5R^5$, —$NR^5CONR^5R^5$, —$NR^5SO_2R^7$ or $R^6$, and $R^2$ is H or —Y-Z, or, (ii) $R^1$ and $R^2$, when taken together, represent unbranched $C_3$–$C_4$ alkylene, optionally wherein one methylene group of said $C_3$–$C_4$ alkylene is replaced by an oxygen atom or a nitrogen atom, said nitrogen atom being optionally substituted by $R^5$ or $R^8$;

Y is a direct bond or $C_1$–$C_3$ alkylene;

Z is $R^{10}$ or, where Y is $C_1$–$C_3$ alkylene, Z is —$NR^5COR^{10}$, —$NR^5CONR^5R^{10}$, —$NR^5CONR^5COR^{10}$ or —$NR^5SO_2R^{10}$;

$R^3$ is H, $C_1$–$C_6$ alkyl, $C_3$–$C_7$ cycloalkyl, phenyl, benzyl, —CN, halo, —$OR^7$, —$CO_2R^5$, —$CONR^5R^5$, —$OCONR^5R^5$, —$NR^5CO_2R^7$, —$NR^5R^5$, —$NR^5COR^5$, —$NR^5CONR^5R^5$, —$NR^5SO_2R^7$ or $R^6$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, —$OCONR^5R^5$, —$NR^5CO_2R^7$, —$NR^5R^5$, —$NR^5COR^5$, —$SO_2NR^5R^5$, —$NR^5CONR^5R^5$, —$NR^5SO_2R^7$ or $R^6$;

$R^4$ is phenyl or pyridyl, each being optionally substituted by $R^6$, halo, —CN, $C_1$–$C_6$ alkyl, fluoro-($C_1$–$C_6$)-alkyl, $C_3$–$C_7$ cycloalkyl or $C_1$–$C_6$ alkoxy;

each $R^5$ is independently either H, $C_1$–$C_6$ alkyl, $C_3$–$C_7$ cycloalkyl, fluoro-($C_1$–$C_6$)-alkyl, phenyl or benzyl, or, when two such groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl and said piperazinyl and homopiperazinyl being optionally substituted on the nitrogen atom not taken together with the two $R^5$ groups to form the ring by —$COR^7$ or —$SO_2R^7$;

$R^6$ is a four to six-membered, aromatic, partially unsaturated or saturated heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by —$OR^5$, —$NR^5R^5$, —CN, oxo, $C_1$–$C_6$ alkyl, $C_3$–$C_7$ cycloalkyl, —$COR^7$ or halo;

$R^7$ is $C_1$–$C_6$ alkyl, $C_3$–$C_7$ cycloalkyl, fluoro-($C_1$–$C_6$)-alkyl, phenyl or benzyl;

$R^8$ is $C_1$–$C_6$ alkyl substituted by phenyl, phenoxy, pyridyl or pyrimidinyl, said phenyl, phenoxy, pyridyl and pyrimidinyl being optionally substituted by halo, —CN, —$CONR^5R^5$, —$SO_2NR^5R^5$, —$NR^5SO_2R^7$, —$NR^5R^5$, —($C_1$–$C_6$ alkylene)-$NR^5R^5$, $C_1$–$C_6$ alkyl, fluoro-($C_1$–$C_6$)-alkyl, $C_3$–$C_7$ cycloalkyl or $C_1$–$C_6$ alkoxy;

$R^9$ is H, $C_1$–$C_6$ alkyl or $C_3$–$C_7$ cycloalkyl, said $C_1$–$C_6$ alkyl and $C_3$–$C_7$ cycloalkyl being optionally substituted by —$OR^5$, —$NR^5R^5$, —$NR^5COR^5$, —$CONR^5R^5$ or $R^6$;

$R^{10}$ is $C_1$–$C_6$ alkyl, $C_3$–$C_6$ alkenyl, $C_3$–$C_6$ alkynyl, $C_3$–$C_7$ cycloalkyl, phenyl, benzyl or C-linked $R^6$, said $C_1$–$C_6$ alkyl, $C_3$–$C_7$ cycloalkyl, phenyl and benzyl being optionally substituted by halo, —$OR^5$, —$OR^{12}$, —CN, —$CO_2R^7$, —$CONR^5R^5$, —$OCONR^5R^5$, —C(=$NR^5$)$NR^5OR^5$, —$CONR^5NR^5R^5$, —$OCONR^5CO_2R^7$, —$NR^5R^5$, —$NR^5R^{12}$, —$NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$;

X is —$CH_2$—, —$CHR^{11}$—, —CO—, —S—, —SO— or —$SO_2$—;

$R^{11}$ is $C_1$–$C_6$ alkyl, $C_3$–$C_7$ cycloalkyl, fluoro-($C_1$–$C_6$)-alkyl or $C_1$–$C_6$ alkoxy; and $R^{12}$ is $C_1$–$C_6$ alkyl substituted by $R^6$, —$OR^5$, —$CONR^5R^5$, —$NR^5COR^5$ or —$NR^5R^5$;

in the manufacture of (a) a reverse transcriptase inhibitor or modulator or (b) a medicament for the treatment of a human immunodeficiency viral (HIV), or genetically related retroviral, infection or a resulting acquired immunodeficiency syndrome (AIDS).

The present invention also provides a novel compound of the formula

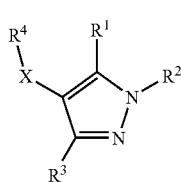

(Ib)

or a pharmaceutically acceptable salt or solvate thereof, wherein either (i) $R^1$ is H, $C_1$–$C_6$ alkyl, $C_3$–$C_7$ cycloalkyl, phenyl, benzyl, halo, —CN, —$OR^7$—$CO_2R^5$, —$CONR^5R^5$, —$OCONR^5R^5$, —$NR^5CO_2R^7$, —$NR^5R^5$, —$NR^5COR^5$, —$NR^5CO$—($C_1$–$C_6$ alkylene)-$OR^5$, —$NR^5CONR^5R^5$, —$NR^5SO_2R^7$ or $R^6$, said $C_1$–$C_6$ alkyl, $C_3$–$C_7$ cycloalkyl, phenyl and benzyl being optionally substituted by halo, —CN, —$OR^5$, —$OR^8$, —$CO_2R^5$, —$CONR^5R^5$, —$OCONR^5R^5$, —$NR^5CO_2R^7$, —$NR^5R^5$, —$NR^8R^9$, —$NR^5COR^5$, —$NR^5COR^6$, —$NR^5COR^8$, —$SO_2NR^5R^5$, —$NR^5CONR^5R^5$, —$NR^5SO_2R^7$ or $R^6$ and $R^2$ is —Y-Z, or, $R^1$ and $R^2$, when taken together, represent unbranched $C_3$–$C_4$ alkylene, optionally wherein one methylene group of said $C_3$–$C_4$ alkylene is replaced by an oxygen atom or a nitrogen atom, said nitrogen atom being optionally substituted by $R^5$ or $R^8$, and $R^3$ is H, $C_1$–$C_6$ alkyl, $C_3$–$C_7$ cycloalkyl, phenyl, benzyl, —CN, halo, —$OR^7$, —$CO_2R^5$, —$CONR^5R^5$, —$OCONR^5R^5$, —$NR^5CO_2R^7$, —$NR^5R^5$, —$NR^5COR^5$, —$NR^5CONR^5R^5$, —$NR^5SO_2R^7$ or $R^6$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, —$OCONR^5R^5$, —$NR^5CO_2R^7$, —$NR^5R^5$, —$NR^5COR^5$, —$SO_2NR^5R^5$, —$NR^5CONR^5R^5$, —$NR^5SO_2R^7$ or $R^6$, or (ii) $R^1$ and $R^3$ are each independently $C_1$–$C_6$ alkyl, $C_3$–$C_7$ cycloalkyl or halo-($C_1$–$C_6$ alkyl), and $R^2$ is H, provided that
(a) for definition (i), $R^1$ and $R^3$ are not both H,
(b) for definition (i), $R^1$ and $R^3$ are not both optionally substituted phenyl, as defined therein,
(c) for definition (i), when $R^1$ and $R^3$ are both methyl, $R^2$ is not phenyl or methyl, and
(d) for definition (ii), $R^1$ and $R^3$ are not both methyl;

Y is a direct bond or $C_1$–$C_3$ alkylene;

Z is $R^{10}$ or, where Y is $C_1$–$C_3$ alkylene, Z is —$NR^5COR^{10}$, —$NR^5CONR^5R^{10}$, —$NR^5CONR^5COR^{10}$ or —$NR^5SO_2R^{10}$;

$R^4$ is phenyl or pyridyl, each substituted by at least one substituent selected from halo, —CN, $C_1$–$C_6$ alkyl, fluoro-($C_1$–$C_6$)-alkyl, $C_3$–$C_7$ cycloalkyl and $C_1$–$C_6$ alkoxy;

each $R^5$ is independently either H, $C_1$–$C_6$ alkyl, $C_3$–$C_7$ cycloalkyl, fluoro-($C_1$–$C_6$)-alkyl, phenyl or benzyl, or, when two such groups are attached to the same nitrogen atom, those two groups taken together with the nitrogen atom to which they are attached represent azetidinyl, pyrrolidinyl, piperidinyl, homopiperdinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl and said piperazinyl and homopiperazinyl being optionally substituted on the nitrogen atom not taken together with the two $R^5$ groups to form the ring by —$COR^7$ or —$SO_2R^7$;

$R^6$ is a four to six-membered, aromatic, partially unsaturated or saturated heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by —$OR^5$, —$NR^5R^5$, —CN, oxo, $C_1$–$C_6$ alkyl, $C_3$–$C_7$ cycloalkyl, —$COR^7$ or halo;

$R^7$ is $C_1$–$C_6$ alkyl, $C_3$–$C_7$ cycloalkyl, fluoro-($C_1$–$C_6$)-alkyl, phenyl or benzyl;

$R^8$ is $C_1$–$C_6$ alkyl substituted by phenyl, pyridyl or pyrimidinyl, said phenyl, pyridyl and pyrimidinyl being optionally substituted by halo, —CN, —$CONR^5R^5$, —$SO_2NR^5R^5$, —$NR^5SO_2R^7$, —$NR^5R^5$, —($C_1$–$C_6$ alkylene)-$NR^5R^5$, $C_1$–$C_6$ alkyl, fluoro-($C_1$–$C_6$)-alkyl, $C_3$–$C_7$ cycloalkyl or $C_1$–$C_6$ alkoxy;

$R^9$ is H, $C_1$–$C_6$ alkyl or $C_3$–$C_7$ cycloalkyl, said $C_1$–$C_6$ alkyl and $C_3$–$C_7$ cycloalkyl being optionally substituted by —$OR^5$, —$NR^5R^5$, —$NR^5COR^5$, —$CONR^5R^5$ or $R^6$;

$R^{10}$ is (a) benzyl or C-linked $R^6$, said benzyl being optionally substituted by halo, —$OR^5$, —$OR^{12}$, —CN, —$CO_2R^7$, —$CONR^5R^5$, —$OCONR^5R^5$, —$C(=NR^5)NR^5OR^5$, —$CONR^5NR^5R^5$, —$CONR^5CO_2R^7$, —$NR^5R^5$, $NR^5R^{12}$, $NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$, or
(b) when $R^1$ and $R^3$ are each independently $C_1$–$C_6$ alkyl, $C_3$–$C_7$ cycloalkyl or halo-($C_1$–$C_6$ alkyl), $R^{10}$ is phenyl, $C_1$–$C_6$ alkyl or $C_3$–$C_7$ cycloalkyl each being optionally substituted by halo, —$OR^5$, —$OR^{12}$, —CN, —$CO_2R^7$, —$CONR^5R^5$, —$OCONR^5R^5$, —$C(=NR^5)NR^5OR^5$, —$CONR^5NR^5R^5$, —$OCONR^5CO_2R^7$, —$NR^5R^5$, —$NR^5R^{12}$, —$NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$;

X is —$CH_2$—, —$CHR^{11}$—, —CO—, —S—, —SO— or —$SO_2$—;

$R^{11}$ is $C_1$–$C_6$ alkyl, $C_3$–$C_7$ cycloalkyl, fluoro-($C_1$–$C_6$)-alkyl or $C_1$–$C_6$ alkoxy; and $R^{12}$ is $C_1$–$C_6$ alkyl substituted by $R^6$, —$OR^5$, —$CONR^5R^5$, —$NR^5COR^5$ or —$NR^5R^5$.

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn-4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. 'C-linked' used in the definition of $R^{10}$ means that the $R^{10}$ substituent is attached through a ring carbon atom. Where $R^1$ and $R^2$ are taken together, they form, along with the nitrogen atom and the carbon atom of the pyrazole ring to which they are attached, a 5- or 6-membered ring.

The pharmaceutically acceptable salts of the compounds of the formula (I) and the compounds of the formula (Ib) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, para-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 66, 1–19, 1977.

The pharmaceutically acceptable solvates of the compounds of the formula (I) and the compounds of the formula (Ib), and the salts thereof, include the hydrates thereof.

Also included within the present scope of the compounds of the formula (I) and the compounds of the formula (Ib) are polymorphs thereof.

A compound of the formula (I) or a compound of the formula (Ib) may contain one or more asymmetric carbon atoms and therefore exist in two or more stereoisomeric forms. The present invention includes the individual stereoisomers of the compounds of the formula (I) and the compounds of the formula (Ib) together with, where appropriate, the individual tautomers thereof, and mixtures thereof.

Separation of diastereoisomers may be achieved by conventional techniques, e.g. by fractional crystallisation, chromatography or high performance liquid chromatography (HPLC) of a stereoisomeric mixture of a compound of the formula (I) or a compound of the formula (Ib) or a suitable salt or derivative thereof. An individual enantiomer of a compound of the formula (I) or a compound of the formula (Ib) may also be prepared from a corresponding optically pure intermediate or by resolution, such as by HPLC of the corresponding racemate using a suitable chiral support or by fractional crystallisation of the diastereoisomeric salts formed by reaction of the corresponding racemate with a suitable optically active acid or base, as appropriate.

Preferred individual compounds according to the invention include the Examples below.

Particularly preferred individual compounds according to the invention include

2-{4-[(3,5-dichlorophenyl)sulfanyl]-3,5-dimethyl-1H-pyrazol-1-yl}ethanol;

2-[4-[(3,5-dichlorophenyl)sulfanyl]-3-ethyl-5-(hydroxymethyl)-1H-pyrazol-1-yl]ethanol; and 2-{4-[(3,5-dichlorophenyl)sulfanyl]-3,5-diethyl-1H-pyrazol-1-yl}ethanol.

The following preferred features of the invention relate both to compounds of the formula (I) and compounds of the formula (Ib).

Preferably, $R^1$ is $C_1$–$C_6$ alkyl, —$OR^7$, —$CO_2R^5$, —$NR^5CO_2R^7$, —$NR^5R^5$, —$NR^5CO$—($C_1$–$C_6$ alkylene)-$OR^5$ or $R^6$, said $C_1$–$C_6$ alkyl being optionally substituted by halo, —CN, —$OR^5$, —$OR^8$, —$CO_2R^5$, —$CONR^5R^5$, —$OCONR^5R^5$, —$NR^5CO_2R^7$, —$NR^5R^5$, —$NR^8R^9$, —$NR^5COR^5$, —$NR^5COR^6$, —$NR^5COR^8$, —$SO_2NR^5R^5$, —$NR^5CONR^5R^5$, —$NR^5SO_2R^7$ or $R^6$.

Preferably, $R^1$ is $C_1$–$C_6$ alkyl, —$OR^7$, —$CO_2R^5$, —$NR^5CO_2R^7$, —$NR^5R^5$, —$NR^5CO$—($C_1$–$C_6$ alkylene)-$OR^5$ or $R^6$, said $C_1$–$C_6$ alkyl being optionally substituted by halo or —$OR^5$.

Preferably, $R^1$ is $C_1$–$C_3$ alkyl, —$OCH_3$, —$CO_2(C_1$–$C_2$ alkyl), —$NHCO_2(C_1$–$C_2$ alkyl), —$NH_2$, —$N(CH_3)_2$, —$NHCOCH_2OCH_3$ or furanyl, said $C_1$–$C_3$ alkyl being optionally substituted by fluoro or —OH.

Preferably, $R^1$ is methyl, ethyl, prop-2-yl, hydroxymethyl, trifluoromethyl, —$OCH_3$, —$CO_2CH_2CH_3$, —$NHCO_2CH_2CH_3$, —$NH_2$, —$N(CH_3)_2$, —$NHCOCH_2OCH_3$ or furan-2-yl.

Preferably, $R^1$ is ethyl.

Preferably, $R^1$ is methyl, ethyl, trifluoromethyl or —$CH_2NHCH_2$(4-cyanophenyl).

Preferably, $R^2$ is H, $C_1$–$C_6$ alkyl, —($C_1$–$C_3$ alkylene)-$NR^5CO$—($C_1$–$C_6$ alkyl), —($C_1$–$C_3$ alkylene)-$NR^5CONR^5$-($C_1$–$C_6$ alkyl), —($C_1$–$C_3$ alkylene)-$NR^5CONR^5CO$-(phenyl), —($C_1$–$C_3$ alkylene)-$NR^5SO_2$(C-linked $R^6$), —($C_1$–$C_3$ alkylene)-$NR^5CO$(C-linked $R^6$), —($C_1$–$C_3$ alkylene)-$NR^5CO$-(phenyl), each $C_1$–$C_6$ alkyl and phenyl being optionally substituted by halo, —$OR^5$, —$OR^{12}$, —CN, —$CO_2R^7$, —$CONR^5R^5$, —$OCONR^5R^5$, —C(=$NR^5$)$NR^5OR^5$, —$CONR^5NR^5R^5$, —$OCONR^5CO_2R^7$, —$NR^5R^5$, —$NR^5R^{12}$, —$NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$.

Preferably, $R^2$ is H, $C_1$–$C_6$ alkyl, —($C_1$–$C_3$ alkylene)-$NR^5CO$—($C_1$–$C_6$ alkyl), —($C_1$–$C_3$ alkylene)-$NR^5CONR^5$-($C_1$–$C_6$ alkyl), —($C_1$–$C_3$ alkylene)-$NR^5CONR^5CO$-(phenyl), —($C_1$–$C_3$ alkylene)-$NR^5SO_2R^6$, —($C_1$–$C_3$ alkylene)-$NR^5COR^6$, —($C_1$–$C_3$ alkylene)-$NR^5CO$-(phenyl), each $C_1$–$C_6$ alkyl and phenyl being optionally substituted by halo, —$OR^5$, —CN, —$CO_2R^7$, —$CONR^5R^5$, —$OCONR^5R^5$, —$OCONR^5CO_2R^7$, —$NR^5R^5$, —$NR^5CONR^5R^5$, —$NR^5COCONR^5R^5$ or $R^6$.

Preferably, $R^2$ is H, $C_1$–$C_3$ alkyl, —($C_1$–$C_2$ alkylene)-NHCO—($C_1$–$C_3$ alkyl), —($C_1$–$C_2$ alkylene)-NHCONH—($C_1$–$C_3$ alkyl), —($C_1$–$C_2$ alkylene)-NHCONHCO-(phenyl), —($C_1$–$C_2$ alkylene)-NHSO$_2R^6$, —($C_1$–$C_2$ alkylene)-NHCOR$^6$, —($C_1$–$C_2$ alkylene)-NHCO-(phenyl), each $C_1$–$C_3$ alkyl and phenyl being optionally substituted by fluoro, —OH, —O($C_1$–$C_6$ alkyl), —CN, —$CO_2(C_1$–$C_6$ alkyl), —$CONH_2$, —$OCONH_2$, —$OCONHCO_2Ph$, —$NH_2$, —$N(C_1$–$C_6$ alkyl)$_2$, —$NHCONH_2$, —$NHCOCONH_2$ or $R^6$.

Preferably, $R^2$ is H, —$CH_2OH$, —$CH_2CH_2OH$, —$CH_2CH_2CH_2OH$, —$CH_2OCONH_2$, —$CH_2CH_2OCONH_2$, —$CH_2OCONHCO_2Ph$, —$CH_2CO_2CH_2CH_3$, —$CH_2CH_2CO_2CH_3$, —$CH_2CH_2CO_2CH_2CH_3$, —$CH_2CH_2CONH_2$, —$CH_2CH_2NH_2$, —$CH_2CH_2CH_2NH_2$, —$CH_2CH_2NHCOCHF_2$, —$CH_2CH_2NHCOCH_2CN$, —$CH_2CH_2NHCOCH_2N(CH_3)_2$, —$CH_2CH_2NHCOCH_2OCH_3$, —$CH_2CH_2NHCOCH_2OH$, —$CH_2CH_2NHCOCH_2OCH_2CH_3$, —$CH_2CH_2NHCOCH_2NHCONH_2$, —$CH_2CH_2NHCOCONH_2$, —$CH_2CH_2NHCONHCH_2CH_3$, —$CH_2CH_2NHCONHCOPh$, —$CH_2CH_2NHCONHCO$(2,6-difluorophenyl), —$CH_2CH_2NHSO_2$(2,4-dihydroxypyrimidin-5-yl), —$CH_2CH_2NHSO_2$(1-methylimidazol-4-yl), —$CH_2CH_2NHCO$(tetrahydrofuran-2-yl), —$CH_2CH_2NHCO$(1,5-dimethylpyrazol-3-yl), —$CH_2CH_2NHCOCH_2$(tetrazol-1-yl), —$CH_2CH_2NHCOPh$, —$CH_2CH_2NHCO$(pyridin-2-yl), —$CH_2CH_2NHCO$(pyrimidin-2-yl), —$CH_2CH_2NHCO$(2-fluorophenyl), —$CH_2CH_2NHCO$(3-hydroxyphenyl), —$CH_2CH_2NHCO$(3- hydroxypyridazin-6-yl), —CH$_2$CH$_2$NHCO(2-hydroxypyridin-6-yl), —CH$_2$CH$_2$NHCO(2-oxo-2H-pyran-5-yl) or —CH$_2$CH$_2$NHCO(1,2,3-thiadiazol-4-yl).

Preferably, R$^2$ is H, methyl, —CH$_2$CH$_2$OH, —CH$_2$CH$_2$CH$_2$OH, —CH$_2$CH$_2$NH$_2$, —CH$_2$CH$_2$CH$_2$NH$_2$, —CH$_2$CN, —CH$_2$CH$_2$OCH$_3$, —CH$_2$CONH$_2$, —CH$_2$CH$_2$NHCOCH$_2$OCH$_3$ or azetidin-3-yl.

Preferably, R$^2$ is —CH$_2$CH$_2$OH, —CH$_2$CH$_2$NH$_2$, —CH$_2$CN or azetidin-3-yl.

Preferably, R$^3$ is C$_1$–C$_6$ alkyl, —CO$_2$R$^5$, —CONR$^5$R$^5$, —NR$^5$CO$_2$R$^7$ or —NR$^5$R$^5$, said C$_1$–C$_6$ alkyl being optionally substituted by halo, —CN, —OR$^5$, —CO$_2$R$^5$, —CONR$^5$R$^5$, —OCONR$^5$R$^5$, —NR$^5$CO$_2$R$^7$, —NR$^5$R$^5$, —NR$^5$COR$^5$, —SO$_2$NR$^5$R$^5$, —NR$^5$CONR$^5$R$^5$, —NR$^5$SO$_2$R$^7$ or R$^6$.

Preferably, R$^3$ is C$_1$–C$_6$ alkyl, —CO$_2$R$^5$, —CONR$^5$R$^5$, —NR$^5$CO$_2$R$^5$ or —NR$^5$R$^5$, said C$_1$–C$_6$ alkyl being optionally substituted by halo, —CN or —OR$^5$.

Preferably, R$^3$ is C$_1$–C$_3$ alkyl, —CO$_2$(C$_1$–C$_2$ alkyl), —CONH$_2$, —NHCO$_2$(C$_1$–C$_4$ alkyl), —N(CH$_3$)$_2$ or —NH$_2$, said C$_1$–C$_3$ alkyl being optionally substituted by halo, —CN or —OH.

Preferably, R$^3$ is methyl, ethyl, prop-2-yl, hydroxymethyl, cyanomethyl, trifluoromethyl, —CO$_2$CH$_2$CH$_3$, —CONH$_2$, —NHCO$_2$C(CH$_3$)$_3$, —N(CH$_3$)$_2$ or —NH$_2$.

Preferably, R$^3$ is methyl, ethyl, prop-2-yl or trifluoromethyl.

Preferably, R$^3$ is ethyl.

Preferably, X is —CH$_2$—, —CHR$^{11}$—, —CO—, —S— or —SO$_2$—.

Preferably, X is —CH$_2$—, —CH(OCH$_3$)—, —CO—, —S— or —SO$_2$—.

Preferably, X is —CH$_2$— or —S—.

Preferably, R$^6$ is azetidinyl, tetrahydropyrrolyl, piperidinyl, azepinyl, oxetanyl, tetrahydrofuranyl, tetrahydropyranyl, oxepinyl, morphoninyl, piperazinyl, diazepinyl, pyrrolyl, furanyl, thienyl, imidazolyl, pyrazolyl, oxazolyl, isoxazolyl, thiazolyl, isothiazolyl, triazolyl, oxadiazolyl, thiadiazolyl, tetrazolyl, pyridinyl, pyranyl, pyridazinyl, pyrimidinyl or pyrazinyl each being optionally substituted by —OR$^5$, —NR$^5$R$^5$, —CN, oxo, C$_1$–C$_6$ alkyl, C$_3$–C$_7$ cycloalkyl, —COR$^7$ or halo.

Preferably, R$^6$ is furan-2-yl, 2,4-dihydroxypyrimidinyl, 1-methylimidazolyl, tetrahydrofuranyl, 1,5-dimethylpyrazolyl, tetrazolyl, pyridinyl, pyrimidinyl, 3-hydroxypyridazinyl, 2-hydroxypyridinyl, 2-oxo-2H-pyranyl or 1,2,3-thiadiazolyl.

Preferably, R$^6$ is 2,4-dihydroxypyrimidinyl, 1-methylimidazolyl, tetrahydrofuranyl, 1,5-dimethylpyrazolyl, tetrazolyl, pyridinyl, pyrimidinyl, 3-hydroxypyridazinyl, 2-hydroxypyridinyl, 2-oxo-2H-pyranyl or 1,2,3-thiadiazolyl.

Preferably, R$^{10}$ is C$_1$–C$_6$ alkyl, phenyl, or C-linked R$^6$, said C$_1$–C$_6$ alkyl and phenyl being optionally substituted by halo, —OR$^5$, —OR$^{12}$, —CN, —CO$_2$R$^7$, —CONR$^5$R$^5$, —OCONR$^5$R$^5$, —C(=NR$^5$)NR$^5$OR$^5$, —CONR$^5$NR$^5$R$^5$, —OCONR$^5$CO$_2$R$^7$, —NR$^5$R$^5$, —NR$^5$R$^{12}$—NR$^5$COR$^5$, —NR$^5$CO$_2$R$^7$, —NR$^5$CONR$^5$R$^5$, —NR$^5$COCONR$^5$R$^5$, —NR$^5$SO$_2$R$^7$, —SO$_2$NR$^5$R$^5$, or R$^6$.

Preferably, R$^{10}$ is C$_1$–C$_6$ alkyl, phenyl, or C-linked R$^6$, said C$_1$–C$_6$ alkyl and phenyl being optionally substituted by halo, —OR$^5$, —CN, —CO$_2$R$^7$, —CONR$^5$R$^5$, —OCONR$^5$R$^5$, —OCONR$^5$CO$_2$R$^7$, —NR$^5$R$^5$, —NR$^5$CONR$^5$R$^5$, —NR$^5$COCONR$^5$R$^5$ or R$^6$.

Preferably, R$^{10}$ is C$_1$–C$_3$ alkyl, phenyl, or R$^6$, said C$_1$–C$_3$ alkyl and phenyl being optionally substituted by fluoro, —OH, —O(C$_1$–C$_6$ alkyl), —CN, —CO$_2$(C$_1$–C$_6$ alkyl), —CONH$_2$, —OCONH$_2$, —OCONHCO$_2$Ph, —NH$_2$, —N(C$_1$–C$_6$ alkyl)$_2$, —NHCONH$_2$, —NHCOCONH$_2$ or R$^6$.

Preferably, R$^{10}$ is —CH$_2$OH, —CH$_2$CH$_2$OH, —CH$_2$CH$_2$CH$_2$OH, —CH$_2$OCONH$_2$, —H$_2$CH$_2$OCONH$_2$, —CH$_2$OCONHCO$_2$Ph, —CH$_2$CO$_2$CH$_3$, —CH$_2$CH$_2$CO$_2$CH$_3$, —CH$_2$CH$_2$CO$_2$CH$_2$CH$_3$, —CH$_2$CH$_2$CONH$_2$, —CH$_2$CH$_2$NH$_2$, —CH$_2$CH$_2$CH$_2$NH$_2$, —CHF$_2$, —CH$_2$CN, —$_2$N(CH$_3$)$_2$, —CH$_2$OCH$_3$, —CH$_2$OH, —CH$_2$OCH$_2$CH$_3$, CH$_2$NHCONH$_2$, —CH$_2$CH$_2$NHCOCONH$_2$, —CH$_2$CH$_2$CH$_3$, phenyl, 2,6-difluorophenyl, 2,4-dihydroxypyrimidin-5-yl, 1-methylimidazol-4-yl, tetrahydrofuran-2-yl, 1,5-dimethylpyrazol-3-yl, —CH$_2$(tetrazol-1-yl), pyridin-2-yl, pyrimidin-2-yl, 2-fluorophenyl, 3-hydroxyphenyl, 3-hydroxypyridazin-6-yl, 2-hydroxypyridin-6-yl, 2-oxo-2H-pyran-5-yl or 1,2,3-thiadiazol-4-yl.

Preferably, R$^{10}$ is methyl, —CH$_2$CH$_2$OH, —CH$_2$CH$_2$CH$_2$OH, —CH$_2$CH$_2$NH$_2$, —CH$_2$CH$_2$CH$_2$NH$_2$, —CH$_2$CN, —CH$_2$CH$_2$OCH$_3$, —CH$_2$CONH$_2$, —CH$_2$CH$_2$NHCOCH$_2$OCH$_3$ or azetidin-3-yl.

The following preferred features of the invention relate to compounds of the formula I).

Preferably, R$^4$ is phenyl optionally substituted by R$^6$, halo, —CN, C$_1$–C$_6$ alkyl, fluoro-(C$_1$–C$_6$)-alkyl, C$_3$–C$_7$ cycloalkyl or C$_1$–C$_6$ alkoxy.

Preferably, R$^4$ is phenyl substituted by halo, —CN or C$_1$–C$_3$ alkyl.

Preferably, R$^4$ is phenyl substituted by fluoro, chloro, bromo, —CN, or methyl.

Preferably, R$^4$ is 3-chlorophenyl, 4-chlorophenyl, 3-fluorophenyl, 3,5-dichlorophenyl, 2,6-difluorophenyl 3,5-difluorophenyl, 3,5-dicyanophenyl, 3,5-dibromophenyl or 3,5-dimethylphenyl.

Preferably, R$^4$ is (i) phenyl substituted at the 3 position by fluoro, chloro, methyl or cyano or (ii) phenyl substituted at the 3 and 5 positions by two substituents independently chosen from fluoro, chloro, methyl and cyano.

The following preferred features of the invention relate to compounds of the formula (Ib).

Preferably, R$^4$ is phenyl substituted by at least one substituent selected from halo, —CN, C$_1$–C$_6$ alkyl, fluoro-(C$_1$–C$_6$)-alkyl, C$_3$–C$_7$ cycloalkyl and C$_1$–C$_6$ alkoxy.

Preferably, R$^4$ is phenyl substituted by at least one substituent selected from halo, —CN and C$_1$–C$_3$ alkyl.

Preferably, R$^4$ is phenyl substituted by at least one substituent selected from fluoro, chloro, bromo, —CN and methyl.

Preferably, R$^4$ is 3-chlorophenyl, 4-chlorophenyl, 3-fluorophenyl, 3,5-dichlorophenyl, 2,6-difluorophenyl, 3,5-difluorophenyl, 3,5-dicyanophenyl, 3,5-dibromophenyl or 3,5-dimethylphenyl.

Preferably, R$^4$ is (i) phenyl substituted at the 3 position by fluoro, chloro, methyl or cyano or (ii) phenyl substituted at the 3 and 5 positions by two substituents independently chosen from fluoro, chloro, methyl and cyano.

All of the compounds of the formula (I) and the compounds of the formula (Ib) can be prepared by conventional routes such as by the procedures described in the general methods presented below or by the specific methods described in the Examples section, or by similar methods thereto. The present invention also encompasses any one or more of these processes for preparing the compounds of formula (Ib).

In the following general methods, R$^1$, R$^2$, R$^3$, R$^4$ and X are as previously defined for a compound of the formula (Ib) or a compound of the formula (I) unless otherwise stated.

Compounds of the formula (Ib) and compounds of the formula (I) in which $R^1$ and $R^3$ are each either H, $C_1$–$C_6$ alkyl, $C_3$–$C_7$ cycloalkyl, phenyl, benzyl, —$CO_2R^5$, —$CONR^5R^5$, or C-linked $R^6$, optionally substituted where allowed, may be prepared by the reaction of a compound of the formula

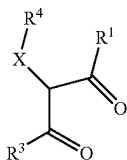

(II)

with a compound of the formula

 $H_2NNHR^2$ (III), or a salt or hydrate thereof, optionally in the presence of an acid or a base, the base preferably being a tertiary amine base such as triethylamine and the acid preferably being acetic acid. In a typical procedure, a solution of the compound of the formula (II) in a suitable solvent, such as ethanol, is treated with the compound of the formula (III), or the salt or hydrate thereof, and, if used, the appropriate acid or base, at a temperature of from room temperature to the reflux temperature of the solvent. In a preferred procedure, the reaction mixture is heated under reflux.

Functional equivalents of compounds of the formula (II) may also be used in this reaction. These include compounds of the formula (IV) or (V), in which $L^1$ and $L^2$, respectively, are each suitable leaving groups, preferably —$N(C_1$–$C_6$ alkyl$)_2$, most preferably —$N(CH_3)_2$.

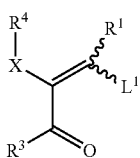

(IV)

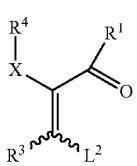

(V)

Thus, a compound of the formula (Ib) or a compound of the formula (I) may be prepared by the condensation of a compound of the formula (IV) or (V) with a compound of the formula (III), or a salt or hydrate thereof, optionally in the presence of an acid or a base, the base preferably being a tertiary amine base such as triethylamine and the acid preferably being acetic acid. In a typical procedure, a solution of the compound of the formula (IV) or (V) in a suitable solvent, such as acetic acid, is treated with the compound of the formula (III), or the salt or hydrate thereof, and, if used, the appropriate acid or base, at a temperature of from room temperature to the reflux temperature of the solvent. In a preferred procedure, the reaction mixture is heated under reflux. Compounds of the formula (IV) or (V) are particularly suitable for the synthesis of compounds of the formula (Ib) or compounds of the formula (I) in which $R^1$ or $R^3$, respectively, is H.

Compounds of the formula (IV) in which $R^1$ is H and $L^1$ is dimethylamino may be prepared by the reaction of a compound of the formula (VI) with dimethylformamide dimethylacetal at an elevated temperature, preferably at about 100° C. Compounds of the formula (V) in which $R^3$ is H and $L^2$ is dimethylamino may be prepared by the reaction of a compound of the formula (VII) under the same conditions. Other compounds of the formula (IV) or (V) in which $L^1$ or $L^2$ is dimethylamino may be prepared analogously.

Compounds of the formula (VI) are either commercially available or may be prepared

(VI)

(VII)

by methods well know in the art. For example, where X is S, compounds of the formula (VI) may be prepared by the reaction of a compound of the formula

 $R^3COCH_2Br$ (VIII)

with a compound of the formula

 $R^4SH$ (IX).

In a typical procedure a solution of a compound of the formula (VIII) in a suitable solvent, such as acetone, is treated with a compound of the formula (IX), optionally treated with a base, such as potassium carbonate and optionally treated with a catalyst such as sodium iodide or tetrabutylammonium iodide. The reaction is preferably performed at room temperature.

Compounds of the formula (VII) are either commercially available or may be prepared from a compound of the formula

 $R^1COCH_2Br$ (X)

and a compound of the formula (IX) in the same way that a compound of the formula (VI) may be prepared from a compound of the formula (VIII).

Compounds of the formula (II) may be prepared using the route shown in Scheme 1 in which $L^3$ is a suitable leaving group, preferably chloro.

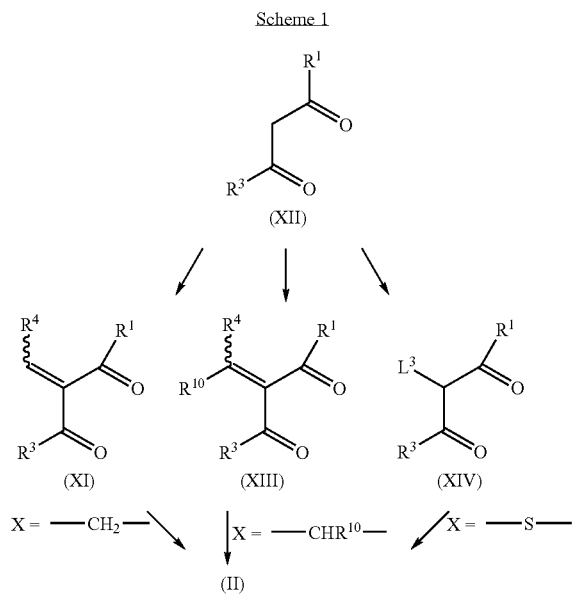

In Scheme 1, compounds of the formula (II) in which X is —$CH_2$— may be prepared by the reduction of a compound of the formula (XI) with a suitable reducing agent such as (a) hydrogen in the presence of a palladium catalyst, (b) diphenylsilane in the presence of a palladium catalyst and a zinc salt or (c) triethylsilane in the presence of an acid such as trifluoroacetic acid. In a typical procedure, a solution of the compound of the formula (XI) in a suitable solvent, such as ethanol or a mixture of ethanol and ethyl acetate, under a hydrogen atmosphere, is treated with 5% w/w palladium on barium sulphate. In another typical procedure, a solution of the compound of the formula (XI) in a suitable solvent, such as dichloromethane, is treated with diphenylsilane, tetrakis(triphenylphosphine)palladium (0) and zinc chloride. In a further typical example, a solution of the compound of the formula (XI) in a suitable solvent, such as dichloromethane, is treated with triethylsilane and trifluoroacetic acid.

Compounds of the formula (XI) may be prepared by the condensation of a compound of the formula (XII) with a compound of the formula $$R^4CHO \qquad (XV),$$

or a functional equivalent thereof, such as an acetal, optionally in the presence of a suitable catalyst, such as a mixture of acetic acid and piperidine. In a typical procedure, a solution of the compound of the formula (XII) in a suitable solvent such as toluene is treated with a compound of the formula (XV), acetic acid and piperidine and heated at a temperature of from room temperature to the reflux temperature of the solvent. Preferably, the reaction mixture is heated under reflux using a Dean-Stark apparatus. Compounds of the formula (XI), prepared in this way, in which $R^1$ and $R^3$ are different, are usually formed as a mixture of stereoisomers. Such a mixture may be used directly in subsequent transformations or separated into its individual stereoisomers which may then be used separately.

Alternatively, compounds of the formula (II) in which X is —$CH_2$— may be prepared by the reaction of a compound of the formula (XII) with a compound of the formula $$R^4CH_2L^6 \qquad (XXVIII)$$

in which $L^6$ is a suitable leaving group, preferably is chloro, bromo, iodo or para-toluenesulphonate, in the presence of a suitable base. In a typical procedure, a solution of the compound of the formula (XII) in a suitable solvent, such as 2-butanone, tetrahydrofuran, acetonitrile or diethyl-ether, is treated with a base, such as sodium ethoxide, sodium hydride or sodium carbonate, and the compound of the formula (XXVIII), optionally with heating. A preferred combination is 2-butanone as the solvent and sodium hydride as the base.

Compounds of the formula (XII) and compounds of the formula (XXVIII) are either commercially available or are easily prepared by methods well known to the skilled person.

Compounds of the formula (II) in which X is —$CHR^{10}$— (other than where $R^{10}$ is $C_1$–$C_6$ alkoxy—see below for the preparation of these compounds) may be prepared by the reduction of a compound of the formula (XIII) with a suitable reducing agent such as (a) hydrogen in the presence of a palladium catalyst, (b) diphenylsilane in the presence of a palladium catalyst and a zinc salt or (c) triethylsilane in the presence of an acid such as trifluoroacetic acid. In a typical procedure, a solution of the compound of the formula (XIII) in a suitable solvent, such as ethanol or a mixture of ethanol and ethyl acetate, under a hydrogen atmosphere, is treated with 5% w/w palladium on barium sulphate. In another typical procedure, a solution of the compound of the formula (XIII) in a suitable solvent, such as dichloromethane, is treated with diphenylsilane, tetrakis(triphenylphosphine) palladium (0) and zinc chloride. In a further typical example, a solution of the compound of the formula (XIII) in a suitable solvent, such as dichloromethane, is treated with triethylsilane and trifluoroacetic acid.

Compounds of the formula (XIII) may be prepared by the condensation of a compound of the formula (XII) with a compound of the formula $$R^4COR^{10} \qquad (XVI),$$

or a functional equivalent thereof, such as a ketal, optionally in the presence of a suitable catalyst, such as a mixture of acetic acid and piperidine. In a typical procedure, a solution of the compound of the formula (XII) in a suitable solvent such as toluene is treated with a compound of the formula (XVI), acetic acid and piperidine and heated at a temperature of from room temperature to the reflux temperature of the solvent. Preferably, the reaction mixture is heated under reflux using a Dean-Stark apparatus. Compounds of the formula (XIII), prepared in this way, in which $R^1$ and $R^3$ are different, are usually formed as a mixture of stereoisomers. Such a mixture may be used directly in subsequent transformations or separated into its individual stereoisomers which may then be used separately.

Compounds of the formula (II) in which X is —S— may be prepared by the reaction of a compound of the formula (XIV) with a compound of the formula (IX). In a typical procedure a solution of a compound of the formula (XIV) in a suitable solvent, such as acetone, is treated with a compound of the formula (IX), optionally treated with a base, such as potassium carbonate and optionally treated with a catalyst such as sodium iodide or tetrabutylammonium iodide. The reaction is preferably performed at room temperature.

Compounds of the formula (XIV) may be prepared by the reaction of a compound of the formula (XII) with a suitable activating agent, e.g. in the case where $L^3$ is chloro, with a chlorinating agent such as sulphuryl chloride. In a typical procedure, where $L^3$ is chloro, the compound of the formula (XII) is treated with sulphuryl chloride, optionally in the presence of a suitable solvent such as dichloromethane.

Compounds of the formula (Ib) and compounds of the formula (I) in which $R^1$ or $R^3$ is —$OR^7$ may be prepared using the route shown in Scheme 2 in which $R^a$ is $C_1$–$C_6$ alkyl and $L^4$ is a suitable leaving group, preferably trifluoromethanesulphonate.

Scheme 2

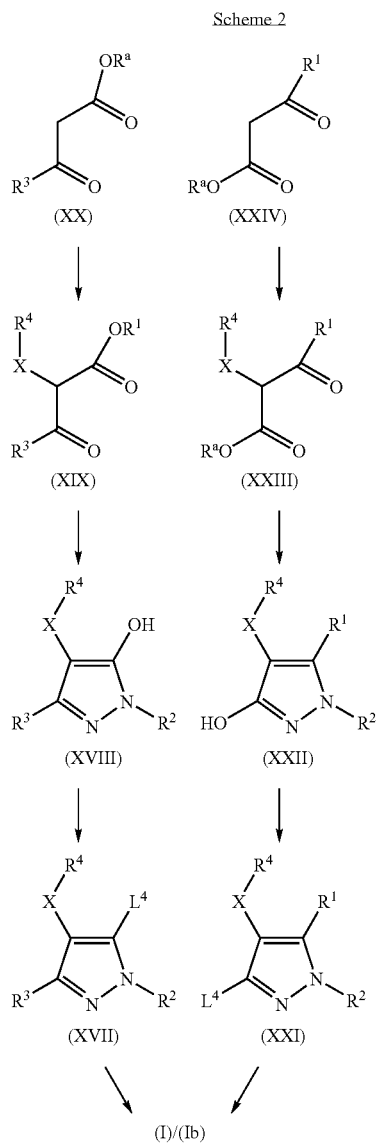

In Scheme 2, compounds of the formula (Ib) and compounds of the formula (1) in which $R^1$ is —$OR^7$ may be prepared by the reaction of a compound of the formula (XVII) with an alcohol of the formula

R⁷OH (XXV)

in the presence of a suitable catalyst, preferably a palladium catalyst, and carbon monoxide. In a typical procedure a mixture of the compound of the formula (XVII), a suitable palladium catalyst such as 1,1'-bis(diphenylphosphino)ferrocenepalladium(II)chloride, the alcohol of the formula (XXV) and, optionally, a suitable solvent such as N,N-dimethylformamide is heated, preferably to about 50° C., under an atmosphere of carbon monoxide, preferably at a pressure of 345 kPa.

Compounds of the formula (XVII) may be prepared by the derivatisation of a compound of the formula (XVIII). In the case where $L^4$ is trifluoromethanesulphonate a suitable derivatising agent is phenyltriflamide. In a typical procedure, where $L^4$ is trifluoromethanesulphonate, a solution of the compound of the formula (XVIII) and a suitable base, preferably a trialkylamine base such as triethylamine, in a suitable solvent such as dichloromethane is treated with phenyltriflamide.

Compounds of the formula (XVIII) may be prepared by the reaction of a compound of the formula (XIX) with a compound of the formula (III), or a salt or hydrate thereof, optionally in the presence of an acid or a base, the base preferably being a tertiary amine base such as triethylamine and the acid preferably being acetic acid. In a typical procedure, a solution of the compound of the formula (XIX) in a suitable solvent, such as ethanol, is treated with the compound of the formula (III), or the salt or hydrate thereof, and, if used, the appropriate acid or base, at a temperature of from room temperature to the reflux temperature of the solvent. In a preferred procedure, the reaction mixture is heated under reflux.

Compounds of the formula (XIX) may be prepared by the derivatisation of a compound of the formula (XX) in the same way that compounds of the formula (II) may be prepared by the derivatisation of a compound of the formula (XII) as described above.

Compounds of the formula (XX) are either commercially available or are readily prepared by methods well known to the skilled person.

In Scheme 2, compounds of the formula (Ib) and compounds of the formula (I) in which $R^3$ is —$OR^7$ may be prepared from a compound of the formula (XXIV) in the same way that a compound of the formula (I) or a compound of the formula (Ib) in which $R^1$ is —$OR^7$ is prepared from a compound of the formula (XX), as described above, mutatis mutandis.

The skilled man will appreciate that compounds of the formula (XVIII) and compounds of the formula (XXII) may exist in one of several tautomeric forms.

Alternatively, compounds of the formula (Ib) and compounds of the formula (I) in which $R^1$ or $R^3$ is —$OR^7$ may be prepared from compounds of the formula (XVIII) or (XXII), respectively, by reaction with a compound of the formula (XXV) under dehydrating conditions, e.g. using the Mitsunobu reaction. In a typical procedure, a solution of the compound of the formula (XVIII) or (XXII) in a suitable solvent, such as tetrahydrofuran is treated with a dialkylazodicarboxylate, preferably diethylazodicarboxylate, a triarylphosphine, preferably triphenylphosphine and a compound of the formula (XXV).

Alternatively, compounds of the formula (Ib) and compounds of the formula (I) in which $R^1$ or $R^3$ is —$OR^7$ may be prepared from compounds of the formula (XVIII) or (XXII), respectively, by reaction with a compound of the formula $R^7L^7$ (XXIX)

in which $L^7$ is a suitable leaving group, preferably halo, optionally in the presence of a suitable base. In a typical procedure, a solution of the compound of the formula (XVIII) or the compound of the formula (XXII) in a suitable solvent, such as tetrahydrofuran, dimethylformamide or ethanol, is treated with a base, such as sodium ethoxide or sodium carbonate, and the compound of the formula (XXIX), optionally with heating.

Compounds of the formula (Ib) and compounds of the formula (I) in which $R^1$ or $R^3$ is halo may be prepared by the reaction, respectively, of a compound of the formula (XVIII) or a compound of the formula (XXII) with a suitable halogenating agent. In a typical procedure, the compound of the formula (XVIII) or (XXII) is treated with POCl$_3$, optionally in the presence of a suitable solvent such as dimethylformamide, to give a compound of the formula (Ib) or a compound of the formula (I) in which $R^1$ or $R^3$, respectively, is chloro.

Compounds of the formula (Ib) and compounds of the formula (I) in which $R^1$ or $R^3$ is —OCONR$^5$R$^5$ may be prepared by the reaction, respectively, of a compound of the formula (XVIII) or a compound of the formula (XXII) with a compound of the formula

$$R^5R^5NCOL^5 \quad (XXVI)$$

in which $L^5$ is a suitable leaving group, preferably chloro, or, in the case where one of the $R^5$ groups is H, with a compound of the formula

$$R^5N=C=O \quad (XXVII).$$

Compounds of the formula (Ib) and compounds of the formula (I) in which $R^1$ or $R^3$ is —NH$_2$ may be prepared by the route shown in Scheme 3.

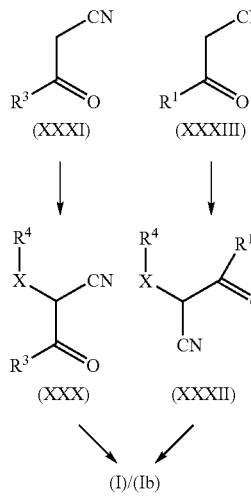

In Scheme 3, compounds of the formula (Ib) and compounds of the formula (I) in which $R^1$ is —NH$_2$ may be prepared by the reaction of a compound of the formula (XXX) with a compound of the formula (III), or a salt or hydrate thereof, optionally in the presence of an acid or a base, the base preferably being a tertiary amine base such as triethylamine and the acid preferably being acetic acid. In a typical procedure, a solution of the compound of the formula (XXX) in a suitable solvent, such as ethanol, is treated with the compound of the formula (III), or the salt or hydrate thereof, and, if used, the appropriate acid or base, at a temperature of from room temperature to the reflux temperature of the solvent. In a preferred procedure, the reaction mixture is heated under reflux.

Compounds of the formula (XXX) may be prepared from a compound of the formula (XXXI) in the same way that compounds of the formula (II) may be prepared from a compound of the formula (XII) as described above.

Compounds of the formula (XXXI) are either commercially available or readily prepared by methods well known to the skilled person.

In Scheme 3, compounds of the formula (Ib) and compounds of the formula (I) in which $R^3$ is —NH$_2$ may be prepared from a compound of the formula (XXXIII) in the same way that compounds of the formula (Ib) and compounds of the formula (I) in which $R^1$ is NH$_2$ may be prepared from compounds of the formula (XXXI), mutatis mutandis.

Compounds of the formula (Ib) and compounds of the formula (I) in which X is —CO— or —CHR$^{10}$— and $R^{10}$ is C$_1$–C$_6$ alkoxy may be prepared by the route shown in Scheme 4 in which R$^b$ is C$_1$–C$_6$ alkyl.

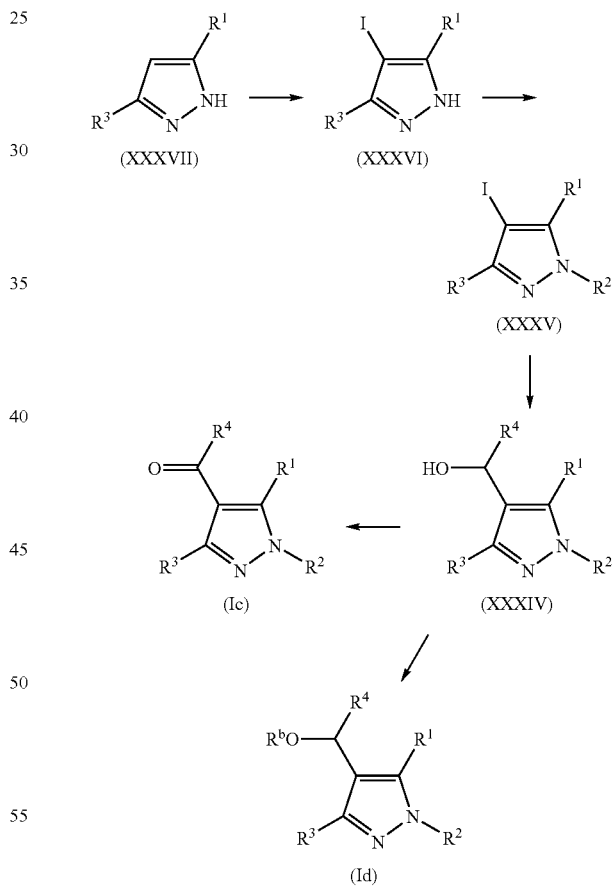

In Scheme 4, compounds of the formula (Ib) and compounds of the formula (I) in which X is —CO— (i.e. compounds of the formula (Ic)) may be prepared by the oxidation of a compound of the formula (XXXIV). In a typical procedure, a solution of a compound of the formula (XXXIV) in a suitable solvent, such as dichloromethane, is treated with N-methylmorpholine-N-oxide and tetra-n-propylammonium perruthenate$^{(VII)}$.

Compounds of the formula (Ib) and compounds of the formula (I) in which X is —CHR$^{10}$— and R$^{10}$ is C$_1$–C$_6$ alkoxy (i.e. compounds of the formula (Id)) may be prepared by the alkylation of a compound of the formula (XXXIV). In a typical procedure, a solution of a compound of the formula (XXXIV) in a suitable solvent, such as N,N-dimethylformamide, is treated with a base, such as sodium hydride, and a compound of the formula $$R^bL^8 \quad (XXXVIII)$$

wherein R$^b$ is C$_1$–C$_6$ alkyl and L$^8$ is a suitable leaving group, preferably chloro, bromo or iodo.

Compounds of the formula (XXXIV) may be prepared by the reaction of a compound of the formula (XXXV) with a suitable metal or organometallic reagent to form an organometallic intermediate which is reacted with a compound of the formula (XV). A preferred metal is magnesium. In a typical procedure, a solution of the compound of the formula (XXXV) in a suitable solvent, such as tetrahydrofuran, is treated with an alkylmagnesium chloride, e.g. iso-propylmagnesium chloride, preferably with cooling in an ice bath, and a compound of the formula (XV) is added.

Compounds of the formula (XXXV) may be prepared by the reaction of a compound of the formula (XXXVI) with a suitable base, preferably sodium hydride, and the addition of a compound of the formula $$R^2L^9 \quad (XXXIX)$$

wherein L$^9$ is a suitable leaving group, preferably a chloro, bromo, iodo or tosylate group. In a typical procedure, a solution of the compound of the formula (XXXVI) in a suitable solvent, such as N,N-dimethylformamide, is treated firstly with a suitable base, such as sodium hydride, and then with a compound of the formula (XXXIX). The reaction is then preferably heated, most preferably to 50° C. If R$^2$ contains a free —OH, —NH$_2$, or —NH— group then a protecting group is preferably employed to mask such functionality. Examples of suitable protecting groups will be apparent to the skilled person [see, for instance, 'Protecting groups in Organic Synthesis (Second Edition)' by Theodora W. Green and Peter G. M. Wuts, 1991, John Wiley and Sons]. The protecting group may be removed immediately or carried through subsequent steps, as described above, and removed as a final step (see below).

Compounds of the formula (XXXVI) may be prepared by the reaction of a compound of the formula (XXXVII) with a suitable iodinating agent. In a typical procedure, a solution of the compound of the formula (XXXVII) in a suitable solvent, such as dichloromethane, is treated with the iodinating agent which is preferably N-iodosuccinimide.

Compounds of the formula (XXXVII) are either commercially available or are readily prepared by methods well known to the skilled man. Such compounds may, for instance, be prepared by analogy with the methods presented above, for example by the reaction of a diketone (XII) with a compound of the formula (III), or a salt or solvate thereof.

It will be appreciated by those skilled in the art that, in many cases, compounds of the formula (Ib) and compounds of the formula (I) may be converted, respectively, into other compounds of the formula (Ib) or compounds of the formula (I) by functional group transformations. For instance:

(a) Compounds of the formula (Ib)/(I) in which R$^2$ is H may be converted into compounds of the formula (Ib)/(I) in which R$^2$ is optionally substituted C$_1$–C$_6$ alkyl by reaction with an appropriate alkylating agent. In a typical procedure, a solution of a compound of the formula (Ib)/(I) in which R$^2$ is H in a suitable solvent such as ethanol or N,N-dimethylformamide is treated with an alkyl bromide and a base such as sodium ethoxide or sodium hydride and heated at a temperature of from room temperature to the reflux temperature of the solvent. A preferred combination is N,N-dimethylformamide as the solvent, sodium hydride as the base and room temperature as the temperature. Examples of specific alkylating agents include bromoacetonitrile, ethyl 4-chloroacetoacetate, ethyl bromoacetate, methyl bromoacetate and chloroethylamine hydrochloride. The use of further specific alkylating agents is illustrated by the Examples below.

(b) Compounds of the formula (Ib)/(I) in which R$^2$ contains as ester functionality may be reduced with a suitable reducing agent, such as lithium aluminium hydride, to give corresponding compounds of the formula (Ib)/(I) in which R$^2$ contains a hydroxy group. In a typical procedure, a solution of the compound of the formula (Ib)/(I), in which R$^2$ contains an ester group, in a suitable solvent, such as diethyl ether, is treated with lithium aluminium hydride, preferably with cooling to a temperature of from −78° C. to 0° C.

(c) Compounds of the formula (Ib)/(I) in which R$^1$ or R$^3$ is —NH$_2$, may be converted into compounds of the formula (Ib)/(I) in which R$^1$ or R$^3$, respectively, is —NHR$^c$, where R$^c$ is C$_1$–C$_6$ alkyl, C$_3$–C$_8$ cycloalkyl or benzyl by a reductive amination with an appropriate aldehyde or ketone. In a typical reductive amination, the reaction will proceed in a suitable solvent such as dichloromethane, in the presence of a suitable reducing agent such as sodium triacetoxyborohydride and optionally in the presence of an acid such as acetic acid. A further reductive amination may be performed on a compound of the formula (Ib)/(I) in which R$^1$ or R$^3$ is —NHR$^c$ to give a compound of the formula (Ib)/(I) in which R$^1$ or R$^3$, respectively, is —NR$^c$R$^c$, where R$^c$ is as defined above and each R$^c$ may be the same or different.

(d) Compounds of the formula (Ib)/(I) in which R$^1$ or R$^3$ is —NHR$^5$, may be converted into compounds of the formula (Ib)/(I) in which, respectively, R$^1$ is —NR$^5$COR$^5$, —NR$^5$CONR$^5$R$^5$, —NR$^5$CO$_2$R$^7$ or —NR$^5$SO$_2$R$^7$ or R$^3$ is —NR$^5$COR$^5$, —NR$^5$CONR$^5$R$^5$, —NR$^5$CO$_2$R$^7$ or —NR$^5$SO$_2$R$^7$ by reaction with an appropriate acylating or sulphonylating agent in a suitable inert solvent, such as dichloromethane, optionally in the presence of a base, preferably a tertiary amine base such as triethylamine.

(e) compounds of the formula (Ib)/(I) in which R$^1$ or R$^3$ is —CO$_2$R$^5$, wherein R$^5$ is other than H, may be converted into compounds of the formula (Ib)/(I) in which R$^1$ or R$^3$, respectively, is —CO$_2$H by hydrolysis. Typically the reaction will be carried out in a suitable solvent, such as aqueous ethanol, or aqueous 1,4-dioxan and in the presence of a base such as sodium hydroxide. Such an acid may be converted to a primary amide by reaction with ammonia and a suitable coupling agent, such as a carbodiimide, e.g. dicyclohexylcarbodiimide. Such a primary amide may then be converted into a nitrile by dehydration with a suitable dehydrating agent, such as phosphoryl chloride.

(f) Compounds of the formula (Ib)/(I) in which R$^1$ or R$^3$ is —CO$_2$H, may be converted into compounds of the formula (Ib)/(I) in which R$^1$ or R$^3$, respectively, is —NH$_2$, by the Curtius rearrangement. In a typical procedure, the reaction is carried out in a suitable solvent, such as dichloromethane, in the presence of a reagent such as diphenylphosphoryl azide.

(g) Compounds of the formula (Ib)/(I) in which X is —S— may be converted into compounds of the formula (Ib)/(I) in which X is —SO— by reaction with a suitable oxidising agent, such as meta-chloroperoxybenzoic acid.

The reaction is carried out in the presence of a suitable solvent such as dichloromethane.

(h) Compounds of the formula (Ib)/(I) in which X is —S— may be converted into compounds of the formula (Ib)/(I) in which X is —SO$^2$— by reaction with a suitable oxidising agent such as Oxone (trade mark), meta-chloroperoxybenzoic acid or hydrogen peroxide. In a typical procedure, a solution of the compound of the formula (Ib)/(I) in which X is —S— in a suitable solvent, such as dichloromethane, is treated with meta-chloroperoxybenzoic acid.

(i) Compounds of the formula (Ib)/(I) in which R$^1$, R$^2$ or R$^3$ contain a heterocycle of the formula R$^6$ may be prepared by standard heterocycle-forming reactions well known to the skilled person (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11), either from another compound of the formula (Ib)/(I) or otherwise. For instance, compounds of the formula (Ib)/(I) in which R$^2$ is (2-amino-6-hydroxypyrimidin-4-yl)methyl may be prepared by the sequential reaction of a compound of the formula (Ib)/(I) in which R$^2$ is H with methyl 4-chloroacetoacetate and then guanidine hydrochloride.

(j) Compounds of the formula (Ib)/(I) in which either R$^1$ or R$^3$ is an N-linked heterocycle of the formula R$^6$ may be prepared from compounds of the formula (Ib)/(I) in which R$^1$ or R$^3$, respectively, is —NH$_2$, by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11).

Compounds of the formula (Ib)/(I) containing an —OH, —NH— or —NH$_2$ group may be prepared by the deprotection of the corresponding compound bearing an —OP$^1$, —NP$^1$— or —NHP$^1$ group, respectively, wherein the group P$^1$ is a suitable protecting group. Examples of suitable protecting groups will be apparent to the skilled person [see, for instance, 'Protecting groups in Organic Synthesis (Second Edition)' by Theodora W. Green and Peter G. M. Wuts, 1991, John Wiley and Sons]. Such compounds bearing an —OP$^1$, —NP$^1$ or —NHP$^1$ group may be prepared using the routes described above, mutatis mutandis.

The compounds of the formula (I) and the compounds of the formula (Ib) can be administered alone but will generally be administered in admixture with a suitable pharmaceutical excipient, diluent or carrier selected with regard to the intended route of administration and standard pharmaceutical practice.

For example, the compounds of the formula (I) and the compounds of the formula (Ib) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) and the compounds of the formula (Ib) may also be administered as fast-dispersing or fast-dissolving dosage forms or in the form of a high energy dispersion or as coated particles. Suitable formulations of the compounds of the formula (I) and the compounds of the formula (Ib) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain between about 0.01 mg and 500 mg of active compound whilst tablet fill weights may range from 50 mg to 1000 mg. An example of a formulation for a 10 mg tablet is illustrated below:

| Ingredient | % w/w |
| --- | --- |
| Compound of the formula (I)/(Ib) or salt | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) and the compounds of the formula (Ib) may be combined with various sweetening or flavouring agents, colouring matter or dyes, with emulsifying and/or suspending agents and with diluents such as water, ethanol, propylene glycol and glycerin, and combinations thereof.

The compounds of the formula (I) and the compounds of the formula (Ib) can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) and the compounds of the formula (Ib) will usually be from 0.01 to 30 mg/kg, preferably from 0.01 to 10 mg/kg (in single or divided doses).

Thus tablets or capsules of the compound of the formula (I) or the compound of the formula (Ib) may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the formula (I) and the compounds of the formula (Ib) may be taken as a single dose as needed or desired.

The compounds of formula (I) and the compounds of the formula (Ib) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) or a compound of the formula (Ib) and a suitable powder base such as lactose or starch.

Alternatively, the compounds of the formula (I) and the compounds of the formula (Ib) can be administered in the form of a suppository or pessary, or they may be applied topically in the form of a gel, hydrogel, lotion, solution, cream, ointment or dusting powder. The compounds of the formula (I) and the compounds of the formula (Ib) may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) and the compounds of the formula (Ib) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) and the compounds of the formula (Ib) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

Oral administration is preferred.

Included within the scope of the present invention are embodiments comprising the co-administration of a compound of the present invention with one or more additional therapeutic agents, and compositions containing a compound of the present invention along with one or more additional therapeutic agents. Such a combination therapy is especially useful for the treatment of infection by HIV and related retroviruses which may evolve rapidly into strains resistant to any monotherapy. Alternatively, additional therapeutic agents may be desirable to treat diseases and conditions which result from or accompany the disease being treated with the compound of the present invention. For example, in the treatment of an HIV or related retroviral infection, it may be desirable to additionally treat opportunistic infections, neoplasms and other conditions which occur as a result of the immuno-compromised state of the patient being treated.

Preferred combinations of the present invention include simultaneous or sequential treatment with a compound of the formula (I) or a compound of the formula (Ib), as defined above, or a pharmaceutically acceptable salt thereof, and:

(a) one or more reverse transcriptase inhibitors such as zidovudine, didanosine, zalcitabine, stavudine, lamivudine, abacavir, adefovir, combivir or trizivir;

(b) one or more non-nucleoside reverse transcriptase inhibitors such as nevirapine, delavirdine or efavirenz;

(c) one or more HIV protease inhibitors such as indanivir, ritonavir, saquinavir or nelfinavir;

(d) one or more CCR5 antagonists such as TAK-779 or SCH-351125;

(e) one or more CXCR4 antagonists such as AMD-3100;

(f) one or more integrase inhibitors;

(g) one or more inhibitors of viral fusion such as T-20 or T-1249;

(h) one or more investigational drugs such as KNI-272, amprenavir, GW-33908, FTC, PMPA, S-1153, MKC-442, MSC-204, MSH-372, DMP450, PNU-140690, ABT-378, KNI-764, DPC-083, TMC-120 or TMC-125; or (i) one or more antifungal or antibacterial agents such as fluconazole.

The activity of the compounds of the invention as reverse transcriptase inhibitors and as agents for treating HIV infections may be measured using the following assays.

A. Inhibition of HIV-1 Reverse Transcriptase Enzyme

The reverse transcriptase activity of the compounds of the invention may be assayed as following. Using the purified recombinant HIV-1 reverse transcriptase (RT, EC, 2.7.7.49) obtained by expression in *Escherichia Coli*, a 96-well plate assay system was established for assaying a large number of samples using either the Poly(rA)-oligo(dT) Reverse Transcriptase [3H]-SPA enzyme assay system (Amersham NK9020) or the [3H]-flashplate enzyme assay system (NEN-SMP 103) and following the manufacturer's recommendations. The compounds were dissolved in 100% DMSO and diluted with the appropriate buffer to a 5% final DMSO concentration. The inhibitory activity was expressed in percent inhibition relative to the DMSO control. The concentration at which the compound inhibited the reverse transcriptase by 50% was expressed as the $IC_{50}$ of the compound.

B. Anti-Human Immunodeficiency Virus (HIV-1) Cell Culture Assay

The anti-HIV activity of the compounds of the invention may be assayed by the following procedures.

1) SupT1 cells were cultured in an RPMI-1640 medium supplemented with 10% foetal calf serum and were split so that they were in growth phase on the day of use.

2) The compounds were dissolved in 100% DMSO and diluted with the above culture medium to predetermined concentrations and distributed in 20 μl aliquots into a 96-well microtiter plate (0.1% DMSO final concentration).

3) To prepare infected cells, 100 μl of RF viruses (TCID50 of $10^7$/ml) were added to $10^6$ cells and incubated for 1 hour at 37° C. The cells were then washed twice in PBS and resuspended in the culture medium at a density of $2.2 \times 10^5$ cells/ml. 180 μl of these infected cells was transferred to wells of the 96 well plate containing the compounds.

4) The plate was incubated in a $CO_2$ incubator at 37° C. for 4 days. The cell survival rates were measured following the manufacturer's recommendations (CellTiter 96® $AQ_{ueous}$ Non-Radioactive Assay—Promega (cat no: G5430)). The concentration at which the compound inhibited the cytotoxic effect of the virus by 50% was expressed as the $EC_{50}$.

Thus the invention provides:

(i) the use of a compound of the formula (I) or a compound of the formula (Ib) or a pharmaceutically acceptable salt or solvate of either in the manufacture of a reverse transcriptase inhibitor or modulator;

(ii) the use of a compound of the formula (I) or a compound of the formula (Ib), or a pharmaceutically acceptable salt or solvate of either in the manufacture of a medicament for the treatment of a human immunodeficiency viral (HIV), or genetically related retroviral, infection or a resulting acquired immunodeficiency syndrome (AIDS);

(iii) a compound of the formula (I) or a compound of the formula (Ib), or a pharmaceutically acceptable salt or solvate of either, for use as a reverse transcriptase inhibitor;

(iv) a compound of the formula (I) or a compound of the formula (Ib) or a pharmaceutically acceptable salt or solvate of either, for use in the treatment of a human immunodeficiency viral (HIV), or genetically related retroviral, infection or a resulting acquired immunodeficiency syndrome (AIDS);

(v) a method of treatment or prevention of a disorder treatable by the inhibition of reverse transcriptase, comprising the administration of an effective amount of a compound of the formula (I) or a compound of the formula (Ib), or a pharmaceutically acceptable salt or solvate of either, to a patient in need of such treatment;

(vi) a method of treatment of a human immunodeficiency viral (HIV), or genetically related retroviral, infection or a resulting acquired immunodeficiency syndrome (AIDS) comprising the administration of an effective amount of a compound of the formula (I) or a compound of the formula (Ib), or a pharmaceutically acceptable salt or solvate of either, to a patient in need of such treatment;

(vii) a compound of the formula (Ib) or a pharmaceutically acceptable salt or solvate thereof;

(viii) a process for the preparation of a compound of the formula (Ib) or a pharmaceutically acceptable salt or solvate thereof;

(ix) a pharmaceutical composition including a compound of the formula (Ib) or a pharmaceutically acceptable salt or solvate thereof, together with a pharmaceutically acceptable excipient, diluent or carrier;

(x) a compound of the formula (Ib) or a pharmaceutically acceptable salt, solvate or composition thereof, for use as a medicament;

The following Examples illustrate the preparation of the compounds of the formula (I) and the compounds of the formula (Ib). The synthesis of certain intermediates used therein are described in the Preparations section that follows the Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; h, hour: Et, ethyl; $CDCl_3$, deuterochloroform; $D_6$-DMSO, deuterodimethylsulphoxide; $CD_3OD$, deuteromethanol; THF, tetrahydrofuran. '0.880 Ammonia solution' means a concentrated aqueous solution of ammonia having a specific gravity of 0.88. Where thin layer chromatography (TLC) has been used it refers to silica gel TLC using silica gel 60 $F_{254}$ plates, $R_f$ is the distance travelled by a compound divided by the distance travelled by the solvent front on a TLC plate. In certain of the Examples there is the possibility of regioisomerism in the product. The structures of certain Examples, for instance Examples 7 and 13 have been proven by nOe experiments. The regiochemistry of other Examples has been assigned by comparing characteristic shifts in their NMR spectra with the corresponding shifts in the NMR spectra of Examples 7 and 13.

Example 1

2-[4-(3,5-Dichlorobenzyl)-3-isopropyl-5-methyl-1H-pyrazol-1-yl]ethanol

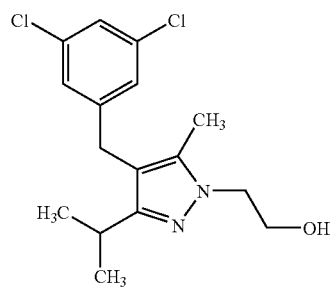

A solution of the ester of Example 7 (170 mg, 0.46 mmol) in dry ether (3.5 ml) was added to a suspension of lithium aluminium hydride (17.5 mg, 0.46 mmol) in dry ether (2 ml) cooled to −78° C. under nitrogen. After stirring at −78° C. for 1 hour and at 0° C. for 1 hour the reaction was quenched with water (5 ml) and then partitioned between ether (30 ml) and aqueous hydrochloric acid solution (pH=3, 30 ml) and the aqueous layer was further extracted with ether (2×30 ml). The combined organic layers were dried over magnesium sulphate and concentrated under reduced pressure. The crude product was purified by flash chromatography on silica gel eluting with pentane:ethyl acetate (2:1, by volume) to provide the title compound (116.3 mg) as a white solid, m.p. 77–78° C.

$^1$H-NMR (400 MHz, CDCl$_3$): δ=1.18 (d, 6H), 2.08 (s, 3H), 2.80 (heptet, 1H), 3.75 (s, 2H), 4.00 (m, 2H), 4.06 (m, 2H), 4.19 (t, 1H), 6.97 (s, 2H), 7.18 (s, 1H).

HRMS (electrospray): m/z [MH$^+$] 327.1026 (calculated 327.1026).

Examples 2 to 6

The compounds of the following tabulated examples of the general formula:

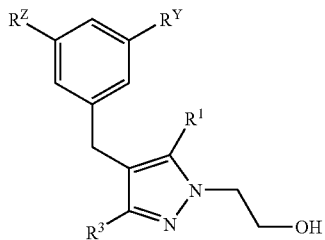

were prepared by a similar method to that of Example 1 using the appropriate esters.

Examples 7 and 8

Ethyl [4-(3,5-dichlorobenzyl)-3-isopropyl-5-methyl-1H-pyrazol-1-yl]acetate (Example 7)

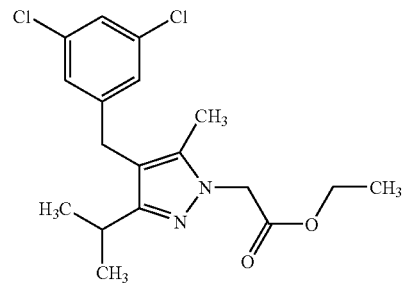

Method A:

A solution of 21% weight/volume sodium ethoxide in ethanol (227 μL, 0.7 mmol) was added dropwise to a stirred solution of the pyrazole of Example 17 (172.7 mg, 0.61 mmol) in dry ethanol (1 ml) at room temperature in a

| Example No. | R$^3$ | R$^1$ | R$^Z$ | R$^Y$ | LRMS m/z = | Analytical data, starting ester and variations in procedure. |
|---|---|---|---|---|---|---|
| 2 | CH$_3$CH$_2$— | CH$_3$CH$_2$— | Cl | Cl | (thermospray): 327 [MH$^+$] | $^1$H-NMR(300 MHz, CDCl$_3$): δ = 1.06(t, 3H), 1.18(t, 3H), 2.50(m, 4H), 3.72(s, 2H), 4.05(m, 2H), 4.12(m, 2H), 4.19(br. t, 1H), 6.99 (s, 2H), 7.19(s, 1H).<br>Contains ca. 10% monodechlorinated impurity as judged by LCMS (50 × 2 mm Magellen 3 micron C18 column, solvent gradient 0.1%, by volume aqueous formic acid: 0.1%, by volume formic acid in acetonitrile (95:5, by volume) to 0.1%, by volume aqueous formic acid: 0.1%, by volume formic acid in acetonitrile (5:95, by volume), electrospray MS).<br>Ester of Example 9.<br>Chromatography with a solvent gradient of toluene:ethyl acetate (1:1, by volume) then toluene:ethyl acetate (1:2, by volume). |
| 3 | CH$_3$CH(CH$_3$)— | CH$_3$— | Cl | H | (thermospray): 293 [MH$^+$] | $^1$H-NMR(400 MHz, CDCl$_3$): δ = 1.15(d, 6H), 2.06(s, 3H), 2.82(m, 1H), 3.73(s, 2H), 3.99(m, 2H), 4.06(m, 2H), 4.29(br. s, 1H), 6.96 (m, 1H), 7.05(s, 1H), 7.15(m, 2H).<br>Microanalysis: Found: C, 65.58; H, 7.30; N, 9.33. C$_{16}$H$_{21}$ClN$_2$O requires C, 65.63; H, 7.23; N, 9.57%.<br>Ester of Example 15.<br>Chromatography with a solvent gradient of pentane:ethyl acetate (2:1, by volume) then pentane:ethyl acetate (1:1, by volume). |
| 4 | CH$_3$CH(CH$_3$)— | CH$_3$— | F | F | (electrospray): 295 [MH$^+$] | $^1$H-NMR(400 MHz, CDCl$_3$): δ = 1.10(d, 6H), 2.10(s, 3H), 2.80 (heptet, 1H), 3.74(s, 2H), 4.00(m, 2H), 4.06(m, 2H), 4.20(t, 1H), 6.60(m, 3H).<br>Ester of Example 16.<br>Chromatography with a solvent gradient of pentane:ethyl acetate (2:1, by volume) then pentane:ethyl acetate (1:1, by volume). |
| 5 | CH$_3$CH(CH$_3$)— | CH$_3$— | F | H | (thermospray): 277 [MH$^+$] | $^1$H-NMR(400 MHz, CDCl$_3$): δ = 1.18(d, 6H), 2.08(s, 3H), 2.84 (heptet, 1H), 3.76(s, 2H), 3.98(m, 2H), 4.05(m, 2H), 4.23(t, 1H), 6.75(d, 1H), 6.86(m, 2H), 7.20(m, 1H).<br>Microanalysis: Found: C, 69.45; H, 7.71; N, 9.96. C$_{16}$H$_{21}$FN$_2$O requires C, 69.54; H, 7.66; N, 10.14%.<br>Ester of Example 10.<br>Chromatography with pentane:ethyl acetate (1:1, by volume). |
| 6 | CH$_3$— | CH$_3$CH(CH$_3$)— | Cl | Cl | (thermospray): 327 [MH$^+$] | $^1$H-NMR(400 MHz, CDCl$_3$): δ = 1.10(d, 6H), 2.06(s, 3H), 3.06 (heptet, 1H), 3.79(s, 2H), 4.00(m, 2H), 4.13(m, 2H), 6.95(s, 2H), 7.18(s, 1H).<br>HRMS(electrospray): m/z [MH$^+$] 327.1031(calculated 327.1026).<br>Ester of Example 8, using Method B<br>Chromatography with a solvent gradient of pentane:ethyl acetate (1:1, by volume) then ethyl acetate. |

Reacti-vial (Trade Mark) (a sealable reaction vessel; available from Pierce & Warriner (UK) Ltd). Ethyl bromoacetate (136 μL, 1.22 mmol) was added and the Reacti-vial (Trade Mark) was sealed and heated at 80° C. for 2 hours and then stirred at room temperature for 16 hours. Further sodium ethoxide in ethanol (227 μL, 0.7 mmol) and ethyl bromoacetate (136 μL, 1.22 mmol) were added and the sealed mixture was heated for a further 7 hours. After cooling to room temperature further sodium ethoxide in ethanol (227 μL, 0.7 mmol) and ethyl bromoacetate (136 μL, 1.22 mmol) were added and the sealed mixture was heated for a further 10 hours. After cooling to room temperature the mixture was concentrated under reduced pressure and the residue was partitioned between water (30 ml) and dichloromethane (30 ml) and the aqueous layer was further extracted with dichloromethane (2×30 ml). The combined organic layers were dried over magnesium sulphate and concentrated under reduced pressure and the crude product (321 mg) was purified by flash chromatography on silica gel eluting with pentane:ethyl acetate (7:1, by volume) to provide Example 7 (175.3 mg) as a white solid, m.p. 90–92° C.

$^1$H-NMR (400 MHz, CDCl$_3$): δ=1.18 (d, 6H), 1.27 (t, 3H), 2.06 (s, 3H), 2.81 (heptet, 1H), 3.74 (s, 2H), 4.22 (q, 2H), 4.83 (s, 2H), 6.96 (s, 2H), 7.17 (s, 1H). This structure was confirmed by nOe experiments.

HRMS (electrospray): m/z [MH$^+$] 369.1135 (calculated 369.1131).

Method B:

A solution of the β-diketone of Preparation 1 (245 mg, 0.85 mmol), ethyl hydrazinoacetate hydrochloride (132 mg, 0.85 mmol) and triethylamine (131 μL, 0.94 mmol) in ethanol (1 ml) was stirred and heated in a sealed Reacti-vial (Trade Mark) at 80° C. for 24 hours. After cooling the mixture was concentrated under reduced pressure and the residue purified by flash chromatography on silica gel eluting with a solvent gradient of pentane:ethyl acetate (10:1, by volume) then pentane:ethyl acetate (5:1, by volume) to provide Example 7 (28.6 mg) as a white solid, m.p. 94–95° C.

Further elution of the column afforded ethyl [4-(3,5-dichlorobenzyl)-5-isopropyl-3-methyl-1H-pyrazol-1-yl]acetate (Example 8) (228.8 mg) as a yellow oil.

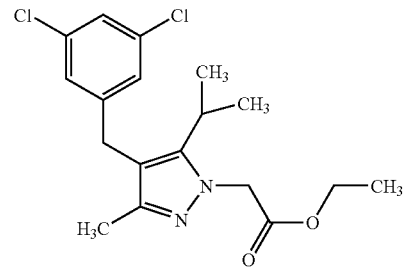

$^1$H-NMR (400 MHz, CDCl$_3$): δ=1.19 (d, 6H), 1.28 (t, 3H), 2.06 (s, 3H), 2.92 (heptet, 1H), 3.82 (s, 2H), 4.23 (q, 2H), 4.86 (s, 2H), 6.96 (s, 2H), 7.17 (s, 1H). This structure was confirmed by nOe experiments.

HRMS (electrospray): m/z [MH$^+$] 369.1134 (calculated 369.1131).

Examples 9 to 10

The compounds of the following tabulated Examples of the general formula:

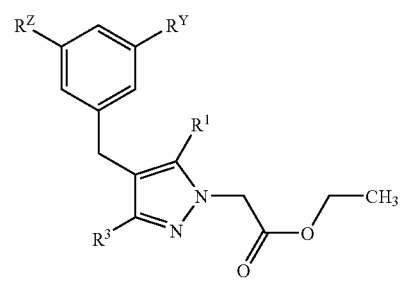

were prepared by a similar method to that of Example 7, Method A using the appropriate pyrazole.

| Example No. | R$^3$ | R$^1$ | R$^Z$ | R$^Y$ | LRMS m/z = | Analytical data, starting pyrazole and variations in procedure. |
|---|---|---|---|---|---|---|
| 9 | CH$_3$CH$_2$— | CH$_3$CH$_2$— | Cl | Cl | (thermospray): 369 [MH$^+$] | $^1$H-NMR(300 MHz, CDCl$_3$): δ = 1.14(t, 3H), 1.16(t, 3H), 1.28(t, 3H), 2.48(m, 4H), 3.75(s, 2H), 4.24(q, 2H), 4.84(s, 2H), 6.99(s, 2H), 7.19(s, 1H). Pyrazole of Example 11. Microanalysis: Found: C, 58.41; H, 5.95; N, 7.39. C$_{18}$H$_{22}$Cl$_2$N$_2$O$_2$ requires C, 58.54; H, 6.00; N, 7.59%. Contains ca. 10% monodechlorinated impurity as judged by LCMS. Chromatography with a solvent gradient of dichloromethane then dichloromethane:methanol (99:1, by volume). |
| 10 | CH$_3$CH(CH$_3$)— | CH$_3$— | F | H | (thermospray): 319 [MH$^+$] | $^1$H-NMR(400 MHz, CDCl$_3$): δ = 1.13(d, 6H), 1.23(t, 3H), 2.03(s, 3H), 2.80(heptet, 1H), 3.75(s, 2H), 4.20(q, 2H), 4.80(s, 2H), 6.71 (d, 1H), 6.85(m, 2H), 7.16(m, 1H). HRMS (electrospray): m/z [MH$^+$] 319.1814 (calculated 319.1817). Pyrazole of Example 19. Chromatography with pentane:ethyl acetate (5:1, by volume). |

Example 11

4-(3,5-Dichlorobenzyl)-3,5-diethyl-1H-pyrazole

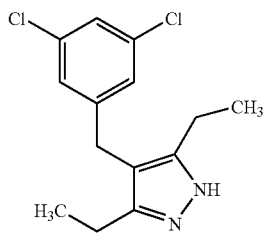

Hydrazine hydrate (187 µL, 3.85 mmol) was added to a stirred solution of the β-diketone of Preparation 5 (1.00 g, 3.5 mmol) in ethanol (2.5 ml) in a Reacti-vial (Trade Mark) at room temperature. The Reacti-vial (Trade Mark) was sealed and the mixture heated at 100° C. for 3 hours. After cooling to room temperature the mixture was concentrated under reduced pressure to leave an oily white solid (1 g) which was purified by flash chromatography on silica gel eluting with dichlormethane:methanol (98:2, by volume) to give the crude product which was recrystallised from diisopropylether (10 ml) to give the title compound (150 mg) as a white solid. LCMS analysis revealed a small amount (ca. 10%) of monodechlorinated impurity carried through of Preparation 5. This impurity could be removed by hplc (150×21.2 mm Phenomenonex Luna $C_{18}$ 5 micron column, solvent gradient 0.1%, by volume aqueous diethylamine:methanol (90:10, by volume) to 0.1%, by volume aqueous diethylamine:methanol (10:90, by volume)) to afford pure title compound.

$^1$H-NMR (300 MHz, CDCl$_3$): δ=1.20 (t, 6H), 2.55 (q, 4H), 3.73 (s, 2H), 6.99 (s, 2H), 7.19 (s, 1H).

LRMS (thermospray): m/z [MH$^+$] 283.

Microanalysis: Found: C, 59.53; H, 5.71; N, 9.82. C$_{14}$H$_{16}$Cl$_2$N$_2$ requires C, 59.38; H, 5.69; N, 9.89%.

Example 12

2-[4-(3,5-Dichlorobenzyl)-3,5-dimethyl-1H-pyrazol-1-yl]ethanol

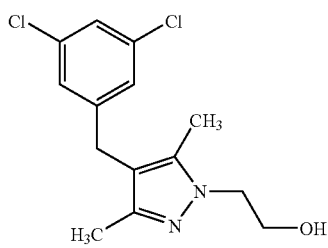

To a stirred suspension of the diketone of Preparation 4 (302 mg, 1.17 mmol) in ethanol (1 ml) was added 2-hydroxyethyl hydrazine (81 µL, 1.29 mmol) and the resulting mixture was heated at 100° C. in a sealed Reacti-vial (Trade Mark) for 6 hours. After cooling, the mixture was concentrated under reduced pressure and the residue was purified by flash chromatography on silica gel eluting with a solvent gradient of pentane:ethyl acetate (1:2, by volume) then pentane:ethyl acetate (1:5, by volume) to afford the title compound (351 mg) as a white powder.

$^1$H-NMR (400 MHz, CDCl$_3$): δ=2.08 (s, 3H), 2.11 (s, 3H), 3.62 (br. m, 1H), 3.66 (s, 2H), 4.00 (m, 2H), 4.07 (m, 2H), 6.95 (s, 2H), 7.16 (s, 1H).

LRMS (thermospray): m/z [MH$^+$] 299.

Microanalysis: Found: C, 56.15; H, 5.38; N, 9.27. C$_{14}$H$_{16}$Cl$_2$N$_2$O requires C, 56.20; H, 5.39; N, 9.36%.

LCMS analysis revealed a small amount (<10%) of dechlorinated impurities presumably arising from the reduction step in Preparation 4 but not detected at that stage. A portion of the product (190 mg) was recrystallised from ethanol:water (2:1, by volume) (3 ml) to afford a white solid (150 mg). LCMS analysis then revealed only a trace amount (<5%) of mono-chlorinated product. This over reduction could probably be avoided by using the alternative reduction procedure of Preparation 6.

Example 13

2-[4-(3,5-Dichlorobenzyl)-5-methyl-3-(trifluoromethyl)-1H-pyrazol-1-yl]ethanol

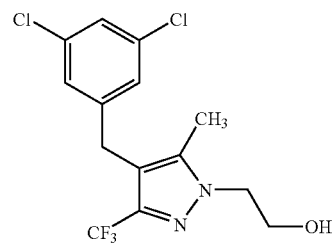

A solution of the diketone of Preparation 6 (76 mg, 0.243 mmol) in ethanol (2 ml) was added to 2-hydroxethyl hydrazine (18 µL, 0.267 mmol) and the resulting mixture was heated at 90° C. in a sealed Reacti-vial (Trade Mark) for 2 hours. After cooling the mixture was concentrated under reduced pressure and the residue was purified by flash chromatography on silica gel eluting with a solvent gradient of dichloromethane then dichloromethane:methanol (99:1, by volume) to afford the title compound (62 mg) as an off-white solid, m.p. 91–93° C.

$^1$H-NMR (400 MHz, CDCl$_3$): δ=2.13 (s, 3H), 2.61 (m, 1H), 3.80 (s, 2H), 4.05 (m, 2H), 4.17 (m, 2H), 6.92 (s, 2H), 7.16 (s, 1H). This structure was confirmed by nOe experiments.

LRMS (thermospray): m/z [MH$^+$] 353.

Microanalysis: Found: C, 47.66; H, 3.75; N, 7.78. C$_{14}$H$_{13}$Cl$_2$F$_3$N$_2$O requires C, 47.61; H, 3.71; N, 7.93%.

Example 14

2-{4-[(4-Chlorophenyl)sulfanyl]-3,5-dimethyl-1H-pyrazol-1-yl}ethanol

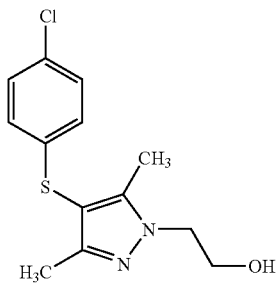

The title compound was prepared by a similar method to that of Example 13 using 3-(4-chlorophenylthio)pentane-2,4-dione except that the crude product was purified by recrystallisation from diisopropylether (ca. 25 ml) to give pale yellow crystals, m.p. 88.9–90.3° C.

$^1$H-NMR 300 MHz, CDCl$_3$): δ=2.20 (s, 3H), 2.29 (s, 3H), 4.04 (t, 2H), 4.12 (t, 2H), 6.90 (d, 2H), 7.18 (d, 2H).

LRMS (thermospray): m/z [MH$^+$] 282.

Microanalysis: Found: C, 54.92; H, 5.39; N, 9.91. C$_{13}$H$_{15}$ClN$_2$OS requires C, 55.22; H, 5.35; N, 9.91%.

Example 15

Ethyl [4-(3-chlorobenzyl)-3-isopropyl-5-methyl-1H-pyrazol-1-yl]acetate

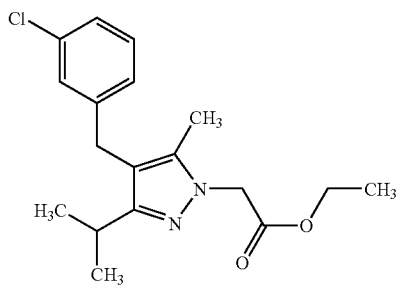

The title compound was prepared by a method similar to that of Example 7, Method A using the pyrazole of Example 20, and was purified by flash chromatography on silica gel eluting with pentane:ethyl acetate (5:1, by volume) and was obtained as a colourless oil.

$^1$H-NMR (400 MHz, CDCl$_3$): δ=1.13 (d, 6H), 1.26 (t, 3H), 2.03 (s, 3H), 2.79 (m, 1H), 3.72 (s, 2H), 4.19 (q, 2H), 4.81 (s, 2H), 6.93 (m, 1H), 7.03 (s, 1H), 7.11 (m, 2H).

LRMS (thermospray): m/z [MH$^+$] 335.

Example 16

Ethyl [4-(3,5-difluorobenzyl)-3-isopropyl-5-methyl-1H-pyrazol-1-yl]acetate

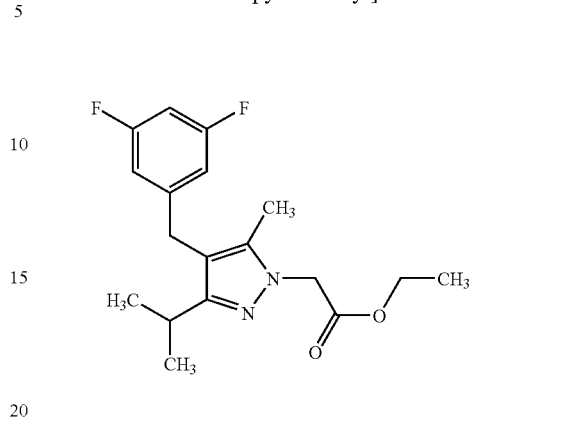

The title compound was prepared by a method similar to that of Example 7, Method A using the pyrazole of Example 18 and was obtained as a yellow oil.

$^1$H-NMR (400 MHz, CDCl$_3$): δ=1.16 (d, 6H), 1.27 (t, 3H), 2.06 (s, 3H), 2.82 (heptet, 1H), 3.76 (s, 2H), 4.23 (q, 2H), 4.84 (s, 2H), 6.60 (m, 3H).

HRMS (electrospray): m/z [MH$^+$] 337.1719 (calculated 337.1722).

Example 17

4-(3,5-Dichlorobenzyl)-3-isopropyl-5-methyl-1H-pyrazole

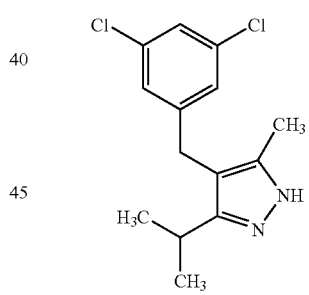

Hydrazine hydrate (50.1 mg, 1 mmol) was added dropwise to a stirred solution of the β-diketone of Preparation 1 (287.2 mg, 1 mmol) in dry ethanol (1 ml) in a Reacti-vial (Trade Mark) at RT. The Reacti-vial (Trade Mark) was sealed and the mixture heated at 80° C. for 24 hours. After cooling to room temperature the mixture was concentrated under reduced pressure and the residue purified by flash chromatography on silica gel eluting with a solvent gradient of pentane:ethyl acetate (3:1, by volume) then pentane:ethyl acetate (2:1, by volume) to afford the title compound (225.6 mg) as a yellow oil.

$^1$H-NMR (400 MHz, CDCl$_3$): δ=1.10 (d, 6H), 2.11 (s, 3H), 2.89 (heptet, 1H), 3.74 (s, 2H), 6.97 (s, 2H), 7.18 (s, 1H).

LRMS (electrospray): m/z [MH$^+$] 285.

Example 18

4-(3,5-Difluorobenzyl)-3-isopropyl-5-methyl-1H-pyrazole

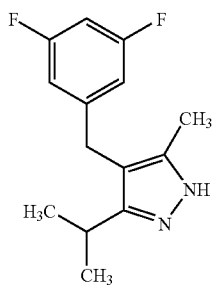

The title compound was prepared by a method similar to that of Example 17 using the β-diketone of Preparation 2 and was purified by flash chromatography on silica gel eluting with pentane:ethyl acetate (2:1, by volume) to afford the title compound as a yellow oil.

$^1$H-NMR (400 MHz, CDCl$_3$): δ=1.16 (d, 6H), 2.08 (s, 3H), 2.85 (heptet, 1H), 3.71 (s, 2H), 6.58 (m, 3H).

LRMS (thermospray): m/z [MH$^+$] 251.

Example 19

4-(3-Fluorobenzyl)-3-isopropyl-5-methyl-1H-pyrazole

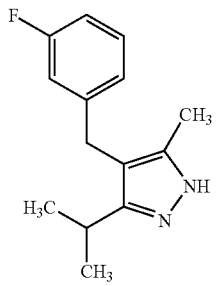

The title compound was prepared by a method similar to that of Example 17 using the β-diketone of Preparation 3 and was purified by flash chromatography on silica gel eluting with a solvent gradient of pentane:ethyl acetate (3:1, by volume) then pentane:ethyl acetate (2:1, by volume) to afford the title compound as a yellow oil.

$^1$H-NMR (400 MHz, CDCl$_3$): δ=1.22 (d, 6H), 2.11 (s, 3H), 2.90 (heptet, 1H), 3.77 (s, 2H), 6.77 (d, 1H), 6.89 (m, 2H), 7.20 (m, 1H).

LRMS (thermospray): m/z [MH$^+$] 233.

Example 20

4-(3-Chlorobenzyl)-3-isopropyl-5-methyl-1H-pyrazole

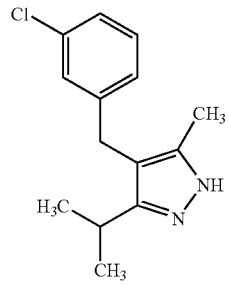

The title compound was prepared by a method similar to that of Example 11 using the β-diketone of Preparation 7 and was purified by flash chromatography on silica gel eluting with a solvent gradient of pentane:ethyl acetate (5:1, by volume) then pentane:ethyl acetate (3:1, by volume) to afford the title compound as a colourless oil.

$^1$H-NMR (400 MHz, CDCl$_3$): δ=1.19 (d, 6H), 2.10 (s, 3H), 2.84–2.97 (m, 1H), 3.74 (s, 2H), 6.94–6.99 (m, 1H), 7.06 (s, 1H), 7.11–7.21 (m, 2H).

LRMS (thermospray): m/z [MH$^+$] 249.

Example 21

2-{4-[(3,5-Dichlorophenyl)sulfanyl]-3,5-dimethyl-1H-pyrazol-1-yl}ethanol

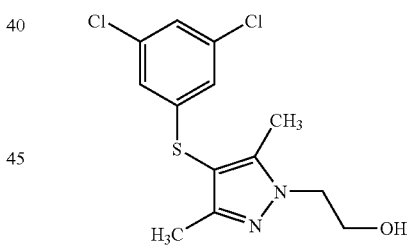

The β-diketone of Preparation 15 (750 mg, 2.71 mmol) was added to a stirred solution of 2-hydroxyethyl hydrazine (202 μL, 2.98 mmol) in ethanol (27 ml) at room temperature under nitrogen and the resulting yellow solution was heated under reflux for 22 hours. After cooling the mixture was concentrated under reduced pressure and the resulting pale yellow solid was purified by flash chromatography on silica gel eluting with methanol:dichloromethane (2:98, by volume) to provide the title compound (729 mg) as a white powder, m.p. 118–120° C.

$^1$H-NMR (400 MHz, CDCl$_3$): δ=2.18 (s, 3H), 2.24 (s, 3H), 3.19 (t, 1H), 4.01 (m, 2H), 4.12 (m, 2H), 6.78 (s, 2H), 7.02 (s, 1H).

LRMS (thermospray): m/z [MH$^+$] 317.

Microanalysis: Found: C, 49.13; H, 4.45; N, 8.59. $C_{13}H_{14}Cl_2N_2OS$ requires C, 49.22; H, 4.45; N, 8.83%.

Example 22

2-{4-[(3,5-Dichlorophenyl)sulfonyl]-3,5-dimethyl-1H-pyrazol-1-yl}ethanol

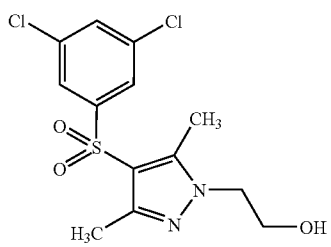

A solution of Oxone (Trade Mark) (581 mg, 0.946 mmol) in water was added to a stirred suspension of the sulphide of Example 21 (200 mg, 0.63 mmol) in methanol (2.5 ml) at 0° C. producing a viscous white suspension. The cooling bath was removed and further methanol (2.5 ml) was added to aid dissolution and stirring. The mixture was stirred at room temperature for 2½ hours and at 50° C. for 24 hours. After cooling the mixture was concentrated under reduced pressure and the residue was partitioned between dichloromethane (50 ml) and water (25 ml). The organic layer was washed with brine (25 ml), dried over magnesium sulphate, filtered and concentrated under reduced pressure to leave a white solid (195 mg). The crude product was pre-absorbed on silica gel and purified by flash chromatography on silica gel eluting with methanol:dichloromethane (2:98, by volume) to provide the title compound (175 mg) as a white solid, m.p. 199–200° C.

$^1$H-NMR (400 MHz, CDCl$_3$): δ=2.37 (s, 3H), 2.51 (s, 3H), 2.70 (s, 1H), 3.99 (m, 2H), 4.05 (m, 2H), 7.51 (s, 1H), 7.70 (s, 2H).

LRMS (thermospray): m/z [MH$^+$] 349.

Microanalysis: Found: C, 44.62; H, 4.03; N, 7.96. C$_{13}$H$_{14}$Cl$_2$N$_2$O$_3$S requires C, 44.71; H, 4.04; N, 8.02%.

Example 23

4-(3,5-Dichlorobenzyl)-3,5-dimethyl-1H-pyrazole

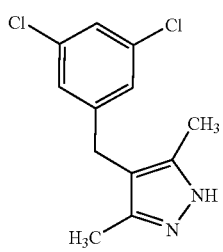

A stirred suspension of the β-diketone of Preparation 4 (1.01 g, 3.90 mmol) in ethanol (3 ml) was treated with hydrazine hydrate (208 μL, 4.29 mmol) and the resulting mixture was heated at 100° C. in a sealed Reacti-vial (Trade Mark) for 3 hours. After cooling, the mixture was concentrated under reduced pressure and the residue was purified by flash chromatography on silica gel eluting with methanol:dichloromethane (2:98, by volume) and then methanol:dichloromethane (5:95, by volume) to afford the title compound (485 mg) as a pale yellow solid, m.p. 133–134° C.

$^1$H-NMR (400 MHz, CDCl$_3$): δ=2.18 (s, 6H), 2.69 (s, 2H), 6.98 (s, 2H), 7.18 (s, 1H).

LRMS (electrospray): m/z [MH$^+$] 255.

Microanalysis: Found: C, 56.72; H, 4.79; N, 10.90. C$_{12}$H$_{12}$Cl$_2$N$_2$ requires C, 56.49; H, 4.74; N, 10.98%.

LCMS analysis of the product revealed a small amount (<20%) of dechlorinated impurities presumably arising from the reduction step in Preparation 4 but not detected at that stage. This over-reduction could be avoided by using the alternative reduction procedure of Preparation 6.

Example 24

2-[4-(3,5-Dichlorobenzyl)-3,5-dimethyl-1H-pyrazol-1-yl]ethanamine

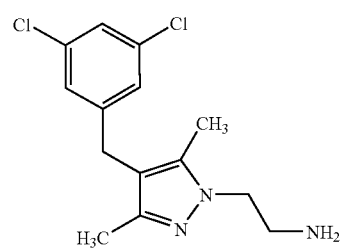

A stirred suspension of the pyrazole (200 mg, 0.78 mmol) of Example 23 and 2-chloroethylamine hydrochloride (136 mg, 1.18 mmol) in toluene (1 ml) was heated at 120° C. in a sealed Reacti-vial (Trade Mark) for 18 hours. After cooling, the mixture was diluted with dichloromethane (30 ml), washed with 2M aqueous sodium hydroxide solution (20 ml), dried over anhydrous magnesium sulphate, filtered and concentrated under reduced pressure. The crude product was purified by flash chromatography on silica gel eluting with methanol:dichloromethane:ammonia (5:95:0.5, by volume) to afford the title compound (45 mg) as white crystals, m.p. 70–72° C.

$^1$H-NMR (400 MHz, CDCl$_3$): δ=2.08 (s, 3H), 2.13 (s, 3H), 3.08 (t, 2H), 3.62 (s, 2H), 4.02 (t, 2H), 6.95 (s, 2H), 7.17 (s, 1H).

LRMS (electrospray): m/z [MH$^+$] 298.

Examples 25 and 26

2-[4-(3,5-Dichlorobenzyl)-5-ethyl-3-(trifluoromethyl)-1H-pyrazol-1-yl]ethanol (Example 25) and 2-[4-(3,5-Dichlorobenzyl)-3-ethyl-5-(trifluoromethyl)-1H-pyrazol-1-yl]ethanol (Example 26)

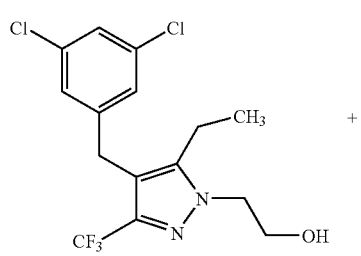

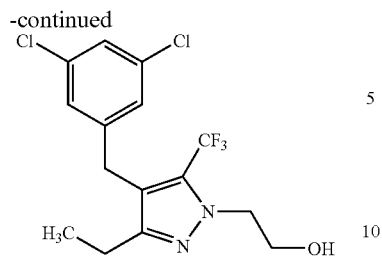

A solution of the β-diketone of Preparation 17 (180 mg, 0.55 mmol) in ethanol (5 ml) was treated with 2-hydroxyethyl hydrazine (41 μL, 0.61 mmol) and heated at 90° C. in a sealed Reacti-vial (Trade Mark) for 5 hours. After cooling, the mixture was concentrated under reduced pressure. The crude product was purified by flash chromatography on silica gel eluting with a solvent gradient of methanol:dichloromethane (0:100, by volume) then methanol:dichloromethane (0.5:99.5, by volume). The less polar product to elute from the column was 2-[4-(3,5-Dichlorobenzyl)-5-ethyl-3-(trifluoromethyl)-1H-pyrazol-1-yl]ethanol isolated as a colourless oil (40 mg), which solidified on standing, m.p. 70–72° C.

$^1$H-NMR (300 MHz, CDCl$_3$): δ=1.03 (t, 3H), 2.60 (q, 2H), 2.90 (t, 1H), 3.87 (s, 2H), 4.13 (m, 2H), 4.20 (m, 2H), 7.00 (s, 2H), 7.20 (s, 1H).

LRMS (thermospray): m/z [MH$^+$] 367.

Microanalysis: Found: C, 48.86; H, 4.07; N, 7.45. C$_{15}$H$_{15}$Cl$_2$F$_3$N$_2$O requires C, 49.07; H, 4.12; N, 7.43%.

The more polar product to elute from the column was further purified by flash chromatography on silica gel eluting with a solvent gradient of acetonitrile:dichloromethane (5:95, by volume) then acetonitrile:dichloromethane (10:90, by volume). 2-[4-(3,5-Dichlorobenzyl)-3-ethyl-5-(trifluoromethyl)-1H-pyrazol-1-yl]ethanol was isolated as a colourless oil (10 mg).

$^1$H-NMR (300 MHz, CDCl$_3$): δ=1.17 (t, 3H), 2.52 (q, 2H), 3.48 (brs, 1H), 3.87 (s, 2H), 4.10 (s, 2H), 4.32 (s, 2H), 6.94 (s, 2H), 7.20 (s, 1H).

LRMS (thermospray): m/z [MH$^+$] 367.

Examples 27 and 28

2-[4-(3,5-Dichlorobenzyl)-5-ethyl-3-methyl-1H-pyrazol-1-yl]ethanol (Example 27) and 2-[4-(3,5-Dichlorobenzyl)-3-ethyl-5-methyl-1H-pyrazol-1-yl]ethanol (Example 28)

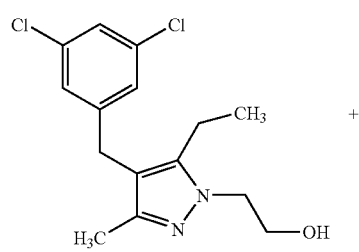

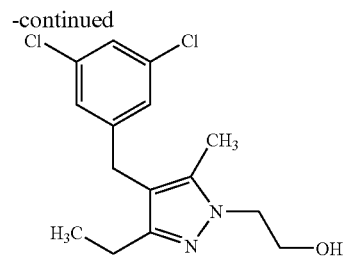

A solution of the β-diketone of Preparation 20 (300 mg, 1.10 mmol) in ethanol (5 ml) was treated with 2-hydroxyethyl hydrazine (81 μL, 1.20 mmol) and heated at 90° C. for 18 hours. After cooling, the mixture was concentrated under reduced pressure. The two isomers were separated by HPLC (Chiracel OD 25 cm×2 cm column; mobile phase, by volume: 80% hexane, 20% iso-propyl alcohol; flow rate: 10 ml/min). The major isomer was isolated as a white solid (60 mg, retention time 12.4 minutes), m.p. 106–107° C. and shown to be 2-[4-(3,5-dichlorobenzyl)-5-ethyl-3-methyl-1H-pyrazol-1-yl]ethanol by nOe experiments.

$^1$H-NMR (300 MHz, CDCl$_3$): δ=1.06 (t, 3H), 2.10 (s, 3H), 2.55 (q, 2H), 3.71 (s, 2H), 4.03 (s, 2H), 4.10 (s, 2H), 6.98 (s, 2H), 7.20 (s, 1H).

LRMS (thermospray): m/z [MH$^+$] 313.

The minor isomer was shown to be 2-[4-(3,5-Dichlorobenzyl)-3-ethyl-5-methyl-1H-pyrazol-1-yl]ethanol and isolated as a white solid (10 mg, retention time 10.0 minutes), m.p. 100–101° C.

$^1$H-NMR (300 MHz, CDCl$_3$): δ=1.16 (t, 3H), 2.16 (s, 3H), 2.52 (q, 2H), 3.74 (s, 2H), 4.03 (s, 2H), 4.13 (s, 2H), 6.98 (s, 2H), 7.20 (s, 1H).

LRMS (thermospray): m/z [MH$^+$] 313.

Example 29

2-[4-(3,5-Dichlorobenzyl)-3-(dimethylamino)-5-methyl-1H-pyrazol-1-yl]ethanol

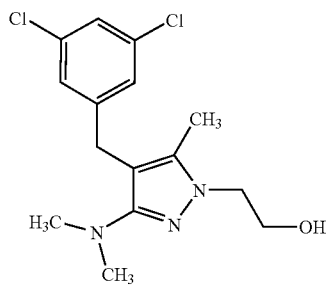

A solution of the amine of Example 87 (18 mg, 0.06 mmol) in dichloromethane (0.3 ml) was treated with triethylamine (8.0 μL, 0.06 mmol) followed by paraformaldehyde (4.0 mg, 0.13 mmol) and stirred at room temperature for 1 hour. Acetic acid was added (3.5 μL, 0.06 mmol) and after a further hour sodium triacteoxyborohydride (19 mg, 0.09 mmol) was added and the reaction mixture was stirred at room temperature for 18 hours. Further paraformaldehyde (2.2 eq) and sodium triacteoxyborohydride (1.5 eq) were added and the reaction mixture was stirred at room temperature for 20 hours. The reaction mixture was diluted with dichloromethane (10 ml) and washed with 10% aqueous potassium carbonate solution (10 ml). The organic extract was concentrated under reduced pressure. The crude material was purified by flash chromatography on silica gel eluting with dichloromethane:methanol:ammonia (98:2:0.5) to afford the title compound as a colourless oil (4.5 mg).

$^1$H-NMR (300 MHz, CDCl$_3$): δ=2.08 (s, 3H), 2.70 (s, 6H), 3.78 (s, 2H), 4.00 (s, 4H), 4.19 (m, 1H), 7.02 (s, 2H), 7.20 (s, 1H).

LRMS (thermospray): m/z [MNH$_4^+$] 346.

Example 30

2-[4-(3,5-Dimethylbenzyl)-3,5-diethyl-1H-pyrazol-1-yl]ethanol

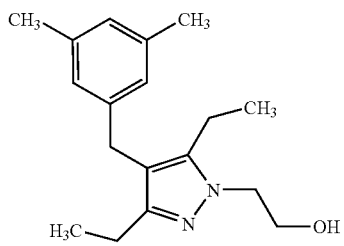

The title compound was prepared by a method similar to that of Example 25, using the β-diketone of Preparation 24. The crude material was purified by flash chromatography on silica gel eluting with methanol:dichloromethane (2:98, by volume) to afford the title compound as a yellow oil, which solidified on standing, m.p. 49.5–51.5° C.

$^1$H-NMR (300 MHz, CDCl$_3$): δ=1.03 (t, 3H), 1.16 (t, 3H), 2.29 (s, 6H), 2.55 (m, 4H), 3.71 (s, 2H), 4.03 (m, 2H), 4.13 (m, 2H), 4.35 (brs, 1H), 6.77 (s, 2H), 6.84 (s, 1H).

LRMS (thermospray): m/z [MH$^+$] 287.

Example 31

2-[4-(3,5-Dichlorobenzyl)-5-methoxy-3-methyl-1H-pyrazol-1-yl]ethanol

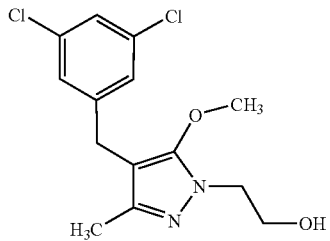

A solution of the ester of Example 88 (42 mg, 0.12 mmol) in tetrahydrofuran (2 ml) at 0° C. was treated dropwise with a solution of lithiumaluminiumhydride (1M in THF) and the resulting mixture was allowed to warm to room temperature and was stirred at this temperature for a further 30 minutes. The reaction mixture was diluted with ethyl acetate and washed with 1M aqueous sodium hydroxide solution and brine. The organic layer was dried over anhydrous magnesium sulphate, filtered and evaporated under reduced pressure to afford the title compound (34 mg) as a white solid.

$^1$H-NMR (400 MHz, CDCl$_3$): δ=2.07 (s, 3H), 3.45 (brs, 1H), 3.72 (s, 2H), 3.79 (s, 3H), 3.95 (m, 2H), 4.03 (m, 2H), 7.02 (s, 2H), 7.20 (s, 1H).

LRMS (thermospray): m/z [MH$^+$] 315.

Example 32

2-[4-(3,5-Dichlorobenzyl)-5-(2-furyl)-3-methyl-1H-pyrazol-1-yl]ethanol

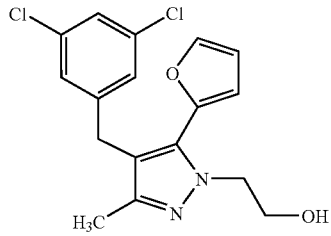

A solution of the β-diketone of Preparation 27 (1.0 g, 3.20 mmol) in ethanol (38 ml) was treated with 2-hydroxyethyl hydrazine (239 μL, 3.53 mmol) and heated under reflux for 18 hours. After cooling, the reaction mixture was concentrated under reduced pressure. The crude material was purified by flash chromatography on silica gel eluting with pentane:ethyl acetate (2:1, by volume) to afford the title compound as a yellow oil, which solidified on standing (703 mg).

$^1$H-NMR (400 MHz, CDCl$_3$): δ=2.16 (s, 3H), 3.58 (t, 1H), 3.80 (s, 2H), 4.01 (m, 2H), 4.28 (m, 2H), 6.37 (d, 1H), 6.49 (m, 1H), 6.99 (s, 2H), 7.18 (s, 1H), 7.36 (s, 1H).

LRMS (thermospray): m/z [MH$^+$] 351.

Microanalysis: Found: C, 58.12; H, 4.63; N, 7.84. $C_{17}H_{16}Cl_2N_2O_2$ requires C, 58.13; H, 4.59; N, 7.98%.

Example 33

(3,5-Dichlorophenyl)[3,5-diethyl-1-(2-hydroxyethyl)-1H-pyrazol-4-yl]methanone

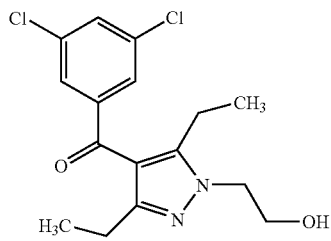

A solution of the protected alcohol of Preparation 32 (70 mg, 0.15 mmol) in tetrahydrofuran (1 ml) was treated with tetrabutylammonium fluoride (1M in THF) (300 μL, 0.30 mmol), at room temperature, under a nitrogen atmosphere. After the reaction mixture had been stirred for 18 hours the solution was concentrated under reduced pressure. The crude material was purified by flash chromatography on silica gel eluting with cyclohexane:ethyl acetate (5:1, by volume) to afford the title compound (30 mg) as a white solid, m.p. 133.5–134.4° C.

¹H-NMR (300 MHz, CDCl₃): δ=1.13 (m, 6H), 2.52 (q, 2H), 2.74 (q, 2H), 3.65 (t, 1H), 4.10 (m, 2H), 4.19 (m, 2H), 7.61 (m, 3H).

LRMS (thermospray): m/z [MH⁺] 341.

Microanalysis: Found: C, 56.03; H, 5.28; N, 8.13. $C_{16}H_{15}Cl_2N_2O_2$ requires C, 56.32; H, 5.32; N, 8.21%.

Example 34

(±)-2-{4-[(3,5-Dichlorophenyl)(methoxy)methyl]-3,5-diethyl-1H-pyrazol-1-yl}ethanol

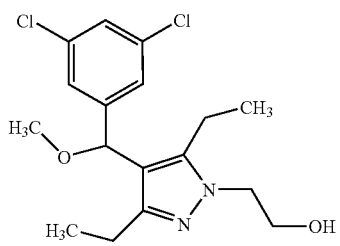

The title compound was prepared by a similar method to that of Example 33 using the protected alcohol of Preparation 33. The crude material was purified by flash chromatography on silica gel eluting with a solvent gradient of cyclohexane:ethyl acetate (5:1, by volume) gradually changing to cyclohexane:ethyl actetate (1:2, by volume) to afford the title compound as a colourless oil.

¹H-NMR (300 MHz, CDCl₃): δ=1.00 (t, 3H), 1.20 (t, 3H), 2.55 (m, 4H), 3.39 (s, 3H), 4.06 (m, 4H), 5.23 (s, 1H), 7.26 (m, 3H).

LRMS (thermospray): m/z [MH⁺] 357.

Example 35

2-[4-(2,6-Difluorobenzyl)-3,5-diethyl-1H-pyrazol-1-yl]ethanol

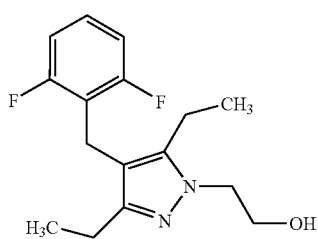

A mixture of the β-diketone of Preparation 35 (89 mg, 0.35 mmol), 2-hydroxyethyl hydrazine (24 μL, 0.35 mmol) and ethanol (350 μL) was heated at 80° C. in a sealed Reacti-vial (Trade Mark) for 18 hours. After cooling, the solution was concentrated under reduced pressure. The crude material was purified by flash chromatography on silica gel eluting with pentane:ethyl acetate (2:1, by volume) to afford the title compound (67 mg) as a white solid, m.p. 70–71° C.

¹H-NMR (400 MHz, CDCl₃): δ=1.00 (t, 3H), 1.15 (t, 3H), 2.55 (q, 2H), 2.62 (q, 2H), 3.73 (s, 2H), 3.97 (m, 2H), 4.00 (m, 2H), 4.26 (t, 1H), 6.84 (t, 2H), 7.15 (m, 1H).

LRMS (electrospray): m/z [MH⁺] 295.

Microanalysis: Found: C, 65.20; H, 6.87; N, 9.48. $C_{16}H_{20}F_2N_2O$ requires C, 65.29; H, 6.85; N, 9.52%.

Example 36

2-[4-(3,5-Dichlorobenzyl)-3,5-diethyl-1H-pyrazol-1-yl]ethyl carbamate

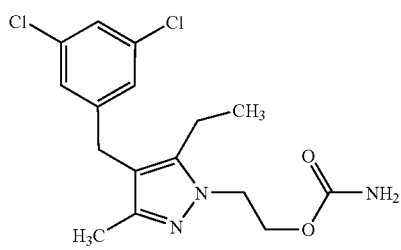

A solution of the alcohol of Example 2 (50 mg, 0.15 mmol) in dichloromethane (1.5 ml) was cooled to 0° C. and treated dropwise with trichloroacetyl isocyanate (22 μL, 0.18 mmol) under a nitrogen atmosphere. After stirring at 0° C. for 1.5 hours the solution was concentrated under reduced pressure. The residue was dissolved in methanol (1 ml) and water (0.5 ml) and cooled to 0° C. Potassium carbonate (64 mg, 0.46 mmol) was added and the resulting mixture was stirred at this temperature for 1 hour. The reaction mixture was allowed to warm to room temperature and stirred for 18 hours. The solution was concentrated under reduced pressure. The residue was partitioned between dichloromethane and water. The organic extract was dried over anhydrous magnesium sulphate, filtered and concentrated under reduced pressure. The crude material was purified by flash chromatography on silica gel eluting with dichloromethane:methanol (98:2, by volume) to afford the title compound (42 mg) as a white solid, m.p. 145–147° C.

¹H-NMR (400 MHz, CDCl₃): δ=1.02 (t, 3H), 1.10 (t, 3H), 2.42 (m, 2H), 2.50 (m, 2H), 3.68 (s, 2H), 4.21 (t, 2H), 4.42 (t, 2H), 4.55 (brs, 2H), 6.94 (s, 2H), 7.15 (s, 1H).

LRMS (thermospray): m/z [MH⁺] 370.

Microanalysis: Found: C, 54.95; H, 5.65; N, 11.20. $C_{17}H_{21}Cl_2N_3O_2$ requires C, 55.14; H, 5.72; N, 11.35%.

Examples 37 and 38

Methyl 3-[4-(3,5-dichlorobenzyl)-3,5-diethyl-1H-pyrazol-1-yl]propanoate (Example 37)

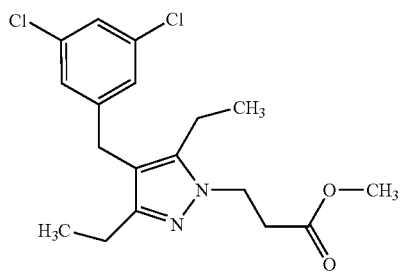

A solution of the pyrazole of Example 11 (198 mg, 0.70 mmol) in ethanol (1 ml) was treated with sodium ethoxide (21% w/v in EtOH) (261 μL, 0.81 mmol) and then methyl- 3-bromopropionate (153 μL, 1.40 mmol) and heated at 70° C. in a sealed Reacti-vial (Trade Mark) for 18 hours. Over a period of 3 days more sodium ethoxide (2.65 eq) and methyl-3-bromopropionate (6.0 eq) were added and the reaction was maintained under the same conditions. After cooling, the solution was concentrated under reduced pressure. The residue was partitioned between dichloromethane and water. The organic phase was dried over anhydrous magnesium sulphate, filtered and concentrated under reduced pressure. The crude material was purified by flash chromatography on silica gel eluting with pentane:ethyl acetate (5:1, by volume) to afford two products.

The first compound eluted off the column was ethyl 3-[4-(3,5-dichlorobenzyl)-3,5-diethyl-1H-pyrazol-1-yl]propanoate (Example 38) isolated as a pale yellow oil (150 mg).

$^1$H-NMR (300 MHz, CDCl$_3$): δ=1.06 (t, 3H), 1.13 (t, 3H), 1.26 (t, 3H), 2.47 (q, 2H), 2.56 (q, 2H), 2.94 (t, 2H), 3.71 (s, 2H), 4.15 (q, 2H), 4.29 (t, 2H), 6.98 (s, 2H), 7.20 (s, 1H).

LRMS (thermospray): m/z [MH$^+$] 383.

Accurate Mass: Found: 383.1284 [MH$^+$]; C$_{19}$H$_{24}$Cl$_2$N$_2$O$_2$ requires 383.1288 [MH$^+$].

The second compound eluted was Example 37 (21 mg) isolated as a colourless oil.

$^1$H-NMR (300 MHz, CDCl$_3$): δ=1.06 (t, 3H), 1.15 (t, 3H), 2.47 (q, 2H), 2.56 (q, 2H), 2.97 (t, 2H), 3.71 (s, 5H), 4.31 (t, 2H), 6.97 (s, 2H), 7.20 (s, 1H).

LRMS (thermospray): m/z [MH$^+$] 369.

Accurate Mass: Found: 369.1128 [MH$^+$]; C$_{18}$H$_{22}$Cl$_2$N$_2$O$_2$ requires 369.1131 [MH$^+$].

Example 39

3-[4-(3,5-Dichlorobenzyl)-3,5-diethyl-1H-pyrazol-1-yl]propanamide

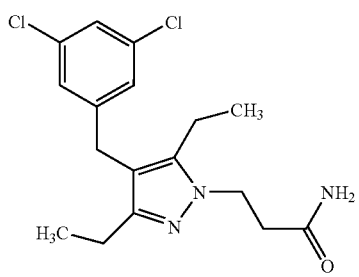

A solution of the ethyl ester of Example 38 (60 mg, 0.16 mmol) in a saturated solution of ammonia in methanol (1.2 ml) was heated at 90° C. in a sealed Reacti-vial (Trade Mark) for 18 hours. Further saturated ammonia in methanol (1.0 ml) was added and the reaction mixture was stirred at 90° C. for 3 days. After cooling, the solution was concentrated under reduced pressure. The crude material was purified by flash chromatography on silica gel eluting with ethyl acetate to afford the title compound (50 mg) as a white solid, m.p. 140–142° C.

$^1$H-NMR (400 MHz, CDCl$_3$): δ=1.00 (t, 3H), 1.08 (t, 3H), 2.40 (q, 2H), 2.52 (q, 2H), 2.80 (t, 2H), 3.66 (s, 2H), 4.26 (t, 2H), 5.26 (brs, 1H), 6.29 (brs, 1H), 6.92 (s, 2H), 7.15 (s, 1H).

LRMS (electrospray): m/z [MH$^+$] 354.

Microanalysis: Found: C, 57.51; H, 6.01; N, 11.57. C$_{17}$H$_{21}$Cl$_2$N$_3$O requires C, 57.63; H, 5.97; N, 11.86%.

Example 40

3-[4-(3,5-Dichlorobenzyl)-3,5-diethyl-1H-pyrazol-1-yl]-1-propanol

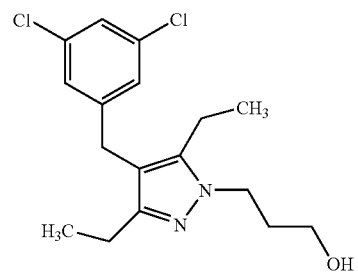

A solution of the ethyl ester of Example 38 (60 mg, 0.16 mmol) in diethyl ether (2 ml) was cooled to −78° C., treated dropwise with lithium aluminium hydride (1M in THF) (170 μL, 0.17 mmol) and stirred at −78° C., under a nitrogen atmosphere for 30 minutes. The reaction mixture was allowed to warm to 0° C. and stirred at this temperature for 1 hour. The reaction was quenched with a few drops of water. The reaction mixture was partitioned between diethyl ether and dilute aqueous hydrochloric acid. The organic phase was dried over anhydrous magnesium sulphate, filtered and concentrated under reduced pressure. The crude material was purified by flash chromatography on silica gel eluting with pentane:ethyl acetate (1:1, by volume) to afford the title compound (39 mg) as a white solid, m.p. 56–59° C.

$^1$H-NMR (300 MHz, CDCl$_3$): δ=1.05 (t, 3H), 1.16 (t, 3H), 2.02 (m, 2H), 2.47 (q, 2H), 2.53 (q, 2H), 3.69 (m, 4H), 4.06 (brs, 1H), 4.20 (t, 2H), 6.97 (s, 2H), 7.20 (s, 1H).

LRMS (thermospray): m/z [MH$^+$] 341.

Microanalysis: Found: C, 59.86; H, 6.54; N, 8.14. C$_{17}$H$_{22}$Cl$_2$N$_2$O requires C, 59.83; H, 6.50; N, 8.21%.

Example 41

[4-(3,5-Dichlorobenzyl)-3,5-diethyl-1H-pyrazol-1-yl]methanol

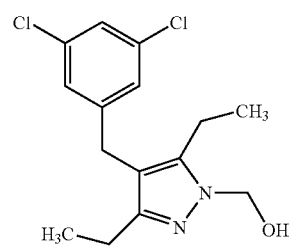

A solution of the pyrazole of Example 11 (283 mg, 1.00 mmol) in water (1 ml) and ethanol (0.5 ml) was treated with 37% W/w aqueous formaldehyde solution (112 μL, 1.50 mmol) and the resulting mixture was stirred at room temperature for 18 hours. The reaction was then stirred under reflux for 2 hours. The reaction mixture was diluted with water and extracted with dichloromethane. The organic extract was dried over anhydrous magnesium sulphate, filtered and concentrated under reduced pressure. The crude material was purified by flash chromatography on silica gel eluting with pentane:ethyl acetate (2:1, by volume) to afford the title compound (231 mg) as a white solid, m.p. 117–118° C.

$^1$H-NMR (300 MHz, CDCl$_3$): δ=1.16 (m, 6H), 2.48 (q, 2H), 2.65 (q, 2H), 3.73 (s, 2H), 5.50 (s, 2H), 5.80 (brs, 1H), 7.00 (s, 2H), 7.20 (s, 1H).

Microanalysis: Found: C, 57.48; H, 5.78; N, 8.87. C$_{15}$H$_{11}$Cl$_2$N$_2$O requires C, 57.52; H, 5.79; N, 8.94%.

Example 42

[4-(3,5-Dichlorobenzyl)-3,5-diethyl-1H-pyrazol-1-yl]methyl carbamate

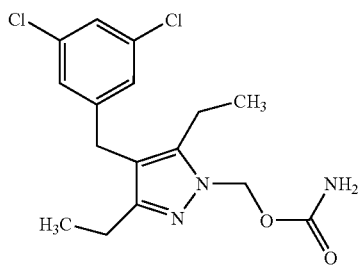

A solution of the alcohol of Example 41 (280 mg, 0.90 mmol) in dichloromethane (5 ml) was cooled to 0° C., treated with trichloroacetyl isocyanate (128 μl, 1.1 mmol) and stirred at 0° C. for 30 minutes. The solution was soaked into a pad of alumina (neutral, activity II, Brockmann), washed with dichloromethane and then extracted with ethyl acetate. The organic extract was concentrated under reduced pressure. The crude material was purified by flash chromatography on silica gel eluting with a solvent gradient of cyclohexane:ethyl acetate (2:1, by volume) gradually changing to cyclohexane:ethyl acetate (1:1, by volume) to afford the title compound (238 mg) as a solid, m.p. 153–155° C.

$^1$H-NMR (400 MHz, CDCl$_3$): δ=1.03 (t, 3H), 1.11 (t, 3H), 2.42 (q, 2H), 2.60 (q, 2H), 3.66 (s, 2H), 4.66 (brs, 2H), 5.94 (s, 2H), 6.92 (s, 2H), 7.13 (s, 1H).

LRMS (thermospray): m/z [MH$^+$] 356.

Microanalysis: Found: C, 54.04; H, 5.39; N, 11.65. C$_{16}$H$_{19}$Cl$_2$N$_3$O$_2$ requires C, 53.94; H, 5.38; N, 11.79%.

Example 43

2-[4-(3,5-Dichlorobenzyl)-3,5-diethyl-1H-pyrazol-1-yl]ethanamine

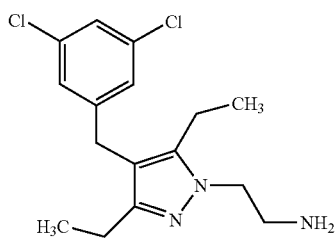

The pyrazole of Example 11 (5.47 g, 19.3 mmol) was mixed with 2-chloroethylamine hydrochloride (2.46 g, 21.3 mmol) and heated neat at 150° C. for 20 hours. After cooling, the solid was partitioned between dichloromethane and 10% aqueous potassium carbonate solution. The organic extract was concentrated under reduced pressure. The crude material was purified by flash chromatography on silica gel eluting with a solvent gradient of dichloromethane:methanol:ammonia (95:5:0, by volume) gradually changing to dichloromethane:methanol:ammonia (90:10:1, by volume) to afford the title compound (3.37 g) as a colourless oil.

$^1$H-NMR (400 MHz, CDCl$_3$): δ=1.03 (t, 3H), 1.15 (t, 3H), 2.45 (q, 2H), 2.52 (q, 2H), 3.16 (t, 2H), 3.71 (s, 2H), 4.06 (t, 2H), 6.97 (s, 2H), 7.18 (s, 1H).

LRMS (thermospray): m/z [MH$^+$] 326

Example 44

N-{2-[4-(3,5-Dichlorobenzyl)-3,5-diethyl-1H-pyrazol-1-yl]ethyl}benzamide

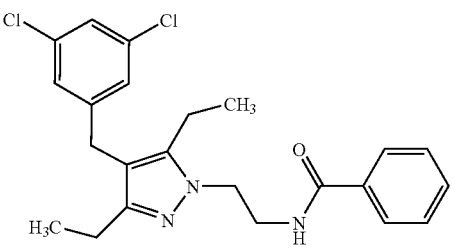

A solution of the amine of Example 43 (98 mg, 0.30 mmol) in dimethylformamide (3.75 ml) was treated with benzoic acid (41 mg, 0.33 mmol), 1-(3-dimethylaminopropyl)-3-ethylcarbodiimide hydrochloride (64 mg, 0.33 mmol) and 4-dimethylaminopyridine (81 mg, 0.66 mmol) and stirred at room temperature for 18 hours. The solution was concentrated under reduced pressure. The residue was partitioned between dichloromethane and saturated sodium hydrogencarbonate solution. The organic extract was dried over anhydrous magnesium sulphate, filtered and concentrated under reduced pressure. The crude material was purified by flash chromatography on silica gel eluting with dichloromethane:methanol (95:5, by volume) to afford the title compound (48 mg) as a white solid, m.p. 115–117° C.

$^1$H-NMR (400 MHz, CDCl$_3$): δ=1.03 (t, 3H), 1.20 (t, 3H), 2.48 (q, 2H), 2.55 (q, 2H), 3.68 (s, 2H), 3.89 (m, 2H), 4.23 (t, 2H), 6.97 (s, 2H), 7.18 (s, 1H), 7.42 (m, 2H), 7.48 (m, 1H), 7.60 (brs, 1H), 7.80 (d, 2H).

LRMS (thermospray): m/z [MH$^+$] 430.

Example 45

N-{2-[4-(3,5-Dichlorobenzyl)-3,5-diethyl-1H-pyrazol-1-yl]ethyl}-1-methyl-1H-imidazole-4-sulfonamide

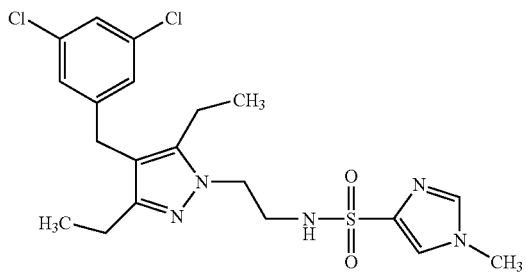

A solution of the amine of Example 43 (98 mg, 0.30 mmol) in dimethylformamide (3.75 ml) was treated with 1-methylimidazole-4-sulphonyl chloride (60 mg, 0.33 mmol) and triethylamine (46 μL, 0.33 mmol) and the resulting mixture was stirred at room temperature for 18 hours. The solution was concentrated under reduced pressure. The residue was partitioned between dichloromethane and saturated aqueous sodium hydrogencarbonate solution. The organic extract was dried over anhydrous magnesium sulphate, filtered and concentrated under reduced pressure. The crude material was purified by flash chromatography on silica gel eluting with dichloromethane:methanol (95:5, by volume) to afford the title compound (55 mg) as a white solid, m.p. 172–174° C.

$^1$H-NMR (400 MHz, CDCl$_3$): δ=1.00 (t, 3H), 1.08 (t, 3H), 2.40 (q, 2H), 2.50 (q, 2H), 3.52 (m, 2H), 3.66 (s, 2H), 3.71 (s, 3H), 4.15 (m, 2H), 6.06 (t, 1H), 6.95 (s, 2H), 7.16 (s, 1H).

LRMS (electrospray): m/z [MH$^+$] 470.

Examples 46 and 47

Ethyl 4-[(3,5-dichlorophenyl)sulfanyl]-5-ethyl-1-(2-hydroxyethyl)-1H-pyrazole-3-carboxylate (Example 46)

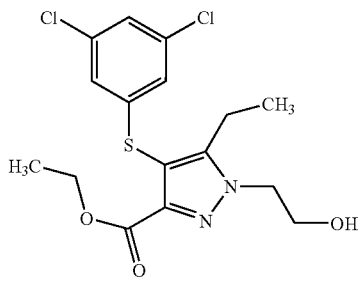

To a stirred suspension of the β-diketone of Preparation 36 (664 mg, 1.90 mmol) in ethanol (1.3 ml) was added 2-hydroxyethyl hydrazine (145 mg, 1.90 mmol) and the resulting mixture was heated at 80° C. in a sealed Reacti-vial (Trade Mark) for 3 hours. After cooling, the mixture was concentrated under reduced pressure and the residue was purified by flash chromatography on silica gel eluting with pentane:ethyl acetate (3:1, by volume) and then pentane:ethyl acetate (1:1, by volume) to afford two compounds.

The more polar material was Example 46 (587 mg) isolated as a pale yellow oil.

$^1$H-NMR (400 MHz, CDCl$_3$): δ=1.13 (t, 3H), 1.25 (t, 3H), 2.82 (q, 2H), 4.12 (q, 2H), 4.35 (m, 4H), 6.89 (s, 2H), 7.00 (s, 1H).

LRMS (electrospray): m/z [MNa$^+$] 411.

The less polar material was ethyl 4-[(3,5-dichlorophenyl)sulfanyl]-3-ethyl-1-(2-hydroxyethyl)-1H-pyrazole-5-carboxylate (Example 47) (40 mg) isolated as a colourless oil.

$^1$H-NMR (400 MHz, CDCl$_3$): δ=1.15 (m, 6H), 2.61 (q, 2H), 4.03 (m, 2H), 4.04 (q, 2H), 4.64 (t, 2H), 6.83 (s, 2H), 7.03 (s, 1H).

LRMS (electrospray): m/z [MH$^+$] 389.

Accurate Mass: Found 389.0481 [MH$^+$]; C$_{16}$H$_{18}$Cl$_2$N$_2$O$_3$S requires 389.0488 [MH$^+$].

Example 48

4-[(3,5-Dichlorophenyl)sulfanyl]-5-ethyl-1-(2-hydroxyethyl)-1H-pyrazole-3-carboxamide

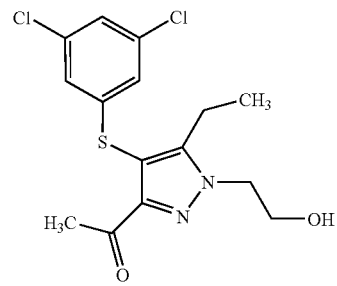

A mixture of Example 46 (407 mg, 1.05 mmol) and 0.880 ammonia solution was heated at 90° C. in a sealed Reacti-vial (Trade Mark) for 18 hours. The precipitate was filtered off and washed with water (5 ml) to afford the title compound (273 mg) as a white solid, m.p. 214–216° C.

$^1$H-NMR (300 MHz, CD$_3$OD): δ=1.13 (t, 3H), 2.82 (q, 2H), 4.01 (t, 2H), 4.32 (t, 2H), 6.99 (s, 2H), 7.19 (s, 1H).

LRMS (thermospray): m/z [MNa$^+$] 382.

Microanalysis: Found: C, 46.59; H, 4.10; N, 11.23. C$_{14}$H$_{15}$Cl$_2$N$_3$O$_2$S requires C, 46.68; H, 4.20; N, 11.66%.

Example 49

2-[4-[(3,5-Dichlorophenyl)sulfanyl]-5-ethyl-3-(hydroxymethyl)-1H-pyrazol-1-yl]ethanol

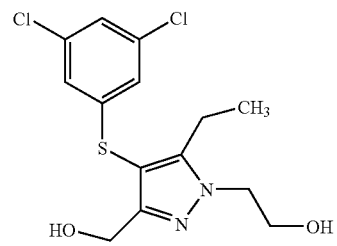

A solution of Example 46 (65 mg, 0.17 mmol) in tetrahydrofuran (2.5 ml) was cooled to −78° C. and treated with lithiumaluminium hydride (1M in THF) (170 μL, 0.17 mmol). After stirring at −78° C. for 2 hours the reaction mixture was allowed to warm to 0° C. for 1 hour and was then allowed to warm to room temperature. After stirring at this temperature for 18 hours, water (1 ml) was added. The reaction mixture was partitioned between ethyl acetate (25 ml) and water (25 ml). The organic phase was dried over anhydrous magnesium sulphate, filtered and concentrated under reduced pressure. The crude material was purified by flash chromatography on silica gel eluting with dichloromethane:methanol (95:5, by volume) to afford the title compound (42 mg) as a colourless oil, which solidified on standing, m.p. 89–90° C.

1H-NMR (400 MHz, CDCl3): δ=1.06 (t, 3H), 2.09 (brs, 1H), 2.67 (q, 2H), 3.13 (brs, 1H), 4.03 (m, 2H), 4.18 (t, 2H), 4.60 (m, 2H), 6.92 (s, 2H), 7.03 (s, 1H).

LRMS (electrospray): m/z [MNa$^+$] 369.

Accurate Mass: Found 347.0383 [MH$^+$]; $C_{14}H_{16}Cl_2N_2O_2S$ requires 347.0383 [MH$^+$].

Example 50

3-[4-(3,5-Dichlorobenzyl)-3,5-diethyl-1H-pyrazol-1-yl]-1-propanamine

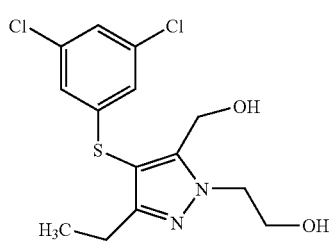

The pyrazole of Example 11 (200 mg, 0.71 mmol) was mixed with 3-chloropropylamine hydrochloride (138 mg, 1.06 mmol). The resulting mixture was heated neat at 150° C., for 24 hours, under a nitrogen atmosphere. After cooling, the reaction mixture was partitioned between dichloromethane (30 ml) and saturated aqueous sodium hydrogencarbonate solution (30 ml). The organic phase was dried over anhydrous magnesium sulphate, filtered and concentrated under reduced pressure. The crude material was purified by flash chromatography on silica gel eluting with a solvent gradient of dichloromethane:methanol:ammonia (90:10:0, by volume) gradually changing to dichloromethane:methanol:ammonia (90:10:1, by volume) to afford the title compound (203 mg) as a brown oil.

$^1$H-NMR (400 MHz, CDCl$_3$): δ=1.04 (t, 3H), 1.13 (t, 3H), 1.96 (m, 2H), 2.45 (q, 2H), 2.50 (q, 2H), 2.78 (t, 2H), 3.69 (s, 2H), 4.09 (t, 2H), 6.99 (s, 2H), 7.19 (s, 1H).

LRMS (electrospray): m/z [MH$^+$] 342.

Example 51

2-[4-[(3,5-Dichlorophenyl)sulfanyl]-3-ethyl-5-(hydroxymethyl)-1H-pyrazol-1-yl]ethanol

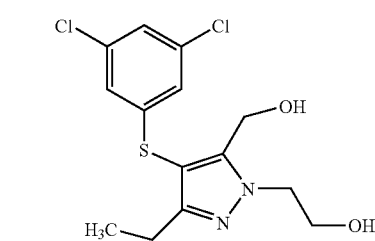

The title compound was prepared by a similar method to that of Example 49 using Example 47 except that the crude material was purified by flash chromatography on silica gel eluting with pentane:ethyl acetate (1:1, by volume) to afford the title compound as a white solid, m.p. 106–108° C.

$^1$H-NMR (300 MHz, CDCl$_3$): δ=1.20 (t, 3H), 2.61 (q, 2H), 2.78 (brs, 1H), 2.97 (brs, 1H), 4.09 (m, 2H), 4.39 (t, 2H), 4.69 (m, 2H), 6.84 (s, 2H), 7.08 (s, 1H).

LRMS (electrospray): m/z [MNa$^+$] 369.

Accurate Mass: Found 347.0394 [MH$^+$]; $C_{14}H_{16}Cl_2N_2O_2S$ requires 347.0383 [MH$^+$].

Example 52

N-{2-[4-(3,5-Dichlorobenzyl)-3,5-diethyl-1H-pyrazol-1-yl]ethyl}-2,2-difluoroacetamide

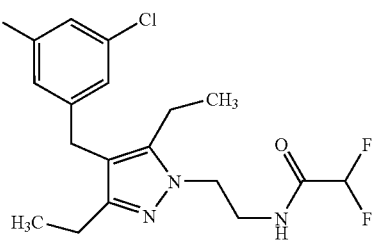

Standard solution: The amine of Example 43 (372 mg, 1.14 mmol), 1-(3-dimethylaminopropyl)-3-ethylcarbodiimide hydrochloride (437 mg, 2.28 mmol) and 4-dimethylaminopyridine (342 mg, 2.28 mmol) were dissolved in dimethylformamide (14.25 ml).

Difluoroacetic acid (2.5 μl, 40 μmol) was treated with the standard solution of amine (250 μL) in a 96 well plate and the mixture was shaken for 18 hours. The reaction mixture was filtered and the filtrate was purified by HPLC (Magellen $C_8$(2) 150×10 mm column; a gradient mobile phase was used, 5:95 (by volume)→95:5 (by volume) acetonitrile: (water, 95% by volume/trifluoroacetic acid, 0.1% by volume/acetonitrile 5%, by volume)).

Retention time: 6.05 minutes

LRMS (electrospray): m/z [MH$^+$] 404.

Examples 53–70

The compounds of the following tabulated Examples of the general formula:

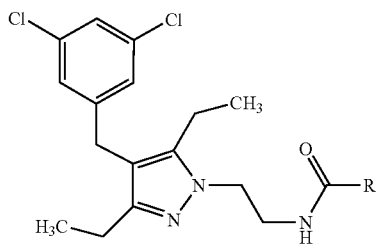

were prepared by a similar method to that of Example 52 using the appropriate acid.

| Example No. | R | HPLC retention time (minutes) | LRMS (electrospray) m/z [M+]= |
|---|---|---|---|
| 53 | 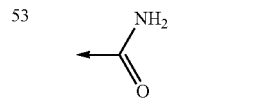 | 5.15 | 397 |
| 54 | 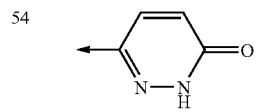 | 4.96 | 448 |
| 55 | 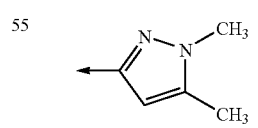 | 5.73 | 448 |
| 56 | 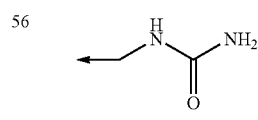 | 4.37 | 426 |
| 57 | 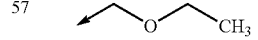 | 6.00 | 412 |
| 58 | 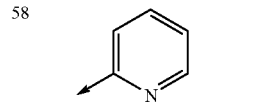 | 6.20 | 431 |
| 59 | 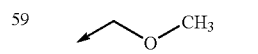 | 5.61 | 398 |
| 60 | 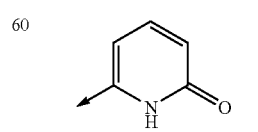 | 5.12 | 447 |
| 61 | 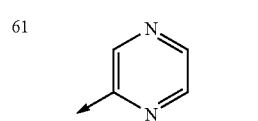 | 5.84 | 432 |
| 62 | | 5.96 | 448 |
| 63 | | 5.22 | 436 |
| 64 | | 5.82 | 424 |
| 65 | | 5.49 | 446 |
| 66 | | 4.96 | 384 |
| 67 | | 6.05 | 438 |
| 68 | | 3.85 | 411 |
| 69 | | 5.54 | 393 |
| 70 | | 6.46 | 448 |

Example 71

[4-(3,5-Dichlorobenzyl)-3,5-diethyl-1H-pyrazol-1-yl]methyl phenyl imidodicarbonate

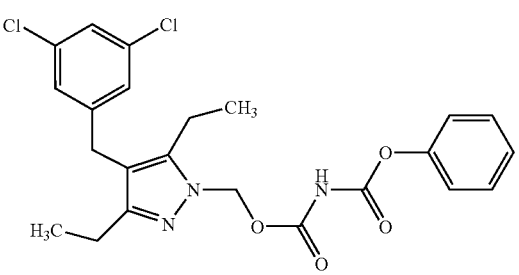

A solution of the alcohol of Example 41 (6.3 mg, 201 mol) in dimethylformamide (250 μL) was treated with phenyl isocyanatoformate (3.6 mg, 22 μmol) and the mixture was shaken for 1.5 hours. The reaction mixture was filtered and the filtrate was purified by HPLC (Hypersil Thermoquest Luna $C_8$ 150×10 mm column; a gradient mobile phase was used, 10:90 (by volume)→95:5 (by volume) acetonitrile:(water, 95% by volume/trifluoroacetic acid, 0.1% by volume/acetonitrile 5%, by volume)).

Retention time: 7.64 minutes

LRMS (electrospray): m/z [MH$^+$] 476.

Example 72

N-{2-[4-(3,5-Dichlorobenzyl)-3,5-diethyl-1H-pyrazol-1-yl]ethyl}-N'-(2,6-difluorobenzoyl)urea

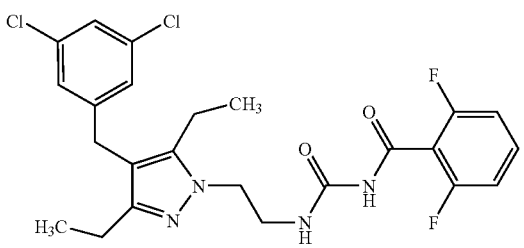

A solution of the amine of Example 43 (6.5 mg, 201 mol) in dimethylformamide (250 µL) was treated with 2,6-difluorobenzoylisocyanate (4.0 mg, 221 mol) and the mixture was shaken for 18 hours. The reaction mixture was filtered and the filtrate was purified by HPLC (Hypersil Thermoquest Luna C$_8$ 150×10 mm column; a gradient mobile phase was used, 10:90 (by volume)→95:5 (by volume) acetonitrile:(water, 95% by volume/trifluoroacetic acid, 0.1% by volume/acetonitrile 5%, by volume)).

Retention time: 6.8–7.4 minutes

LRMS (electrospray): m/z [MH$^+$] 509.

Examples 73–74

The compounds of the following tabulated Examples of the general formula:

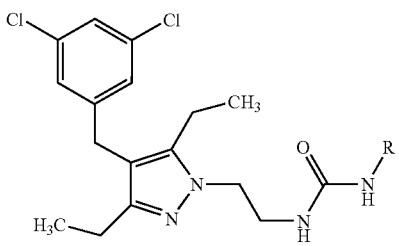

were prepared by a similar method to that of Example 72 using the appropriate isocyanate.

| Example No. | R | HPLC retention time (minutes) | LRMS (electrospray) m/z [M$^+$] = |
|---|---|---|---|
| 73 | ⌃⌄ | 6.23 | 411 |
| 74 | 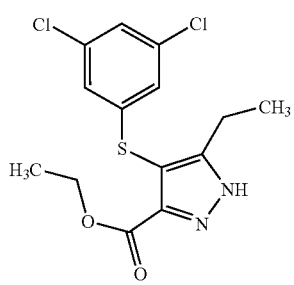 | 7.21 | 473 |

Example 75

N-{2-[4-(3,5-Dichlorobenzyl)-3,5-diethyl-1H-pyrazol-1-yl]ethyl}-2,4-dioxo-1,2,3,4-tetrahydro-5-pyrimidinesulfonamide

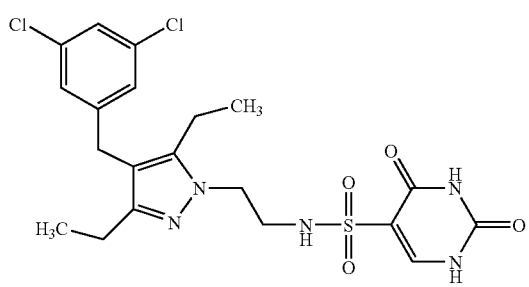

A solution of the amine of Example 43 (6.5 mg, 20 µmol) and triethylamine (6 µl, 40 µmol) in dimethylformamide (250 µL) was treated with 2,4-dioxo-1,2,3,4-tetrahydro-5-pyrimidinesulfonyl chloride (J. Am. Chem. Soc., 1956, 78, 401) (0.8 mg, 4.0 µmol) and the mixture was shaken for 18 hours. The reaction mixture was filtered and the filtrate was purified by HPLC (Hypersil Thermoquest Luna C$_8$ 150×10 mm column; a gradient mobile phase was used, 10:90 (by volume)→95:5 (by volume) acetonitrile:(water, 95% by volume/trifluoroacetic acid, 0.1% by volume/acetonitrile 5%, by volume)).

Retention time: 6.00 minutes

LRMS (electrospray): m/z [MH$^+$] 500.

Example 76

Ethyl 4-[(3,5-dichlorophenyl)sulfanyl]-5-ethyl-1H-pyrazole-3-carboxylate

To a stirred solution of the β-diketone of Preparation 36 (2.00 g, 5.73 mmol) in ethanol (3 ml) was added hydrazine monohydrate (278 μl, 5.73 mmol) and the resulting mixture was heated at 80° C. in a sealed Reacti-vial (Trade Mark) for 2 hours. After cooling, the mixture was dissolved in water and the resulting solution was extracted with dichloromethane and followed by ethyl acetate. The combined organic phases were washed with brine and concentrated under reduced pressure. The residue was purified by flash chromatography on silica gel eluting with cyclohexane:ethyl acetate (5:1, by volume) and then cyclohexane:ethyl acetate (3:1, by volume) to afford the product as an oily white solid. This material was washed with pentane and the white solid was collected by filtration and air dried to give a pure sample of the title compound (450 mg), m.p. 138–139° C.

$^1$H-NMR (400 MHz, CDCl$_3$): δ=1.21 (m, 6H), 2.72 (q, 2H), 4.32 (q, 2H), 6.84 (s, 2H), 7.04 (s, 1H).

LRMS (electrospray): m/z [M–H$^+$] 343.

Microanalysis: Found: C, 48.53; H, 3.95; N, 8.00. C$_{14}$H$_{14}$Cl$_2$N$_2$O$_2$S requires C, 48.71; H, 4.09; N, 8.11%.

Example 77

[4-[(3,5-Dichlorophenyl)sulfanyl]-5-ethyl-1-(2-hydroxyethyl)-1H-pyrazol-3-yl]acetonitrile

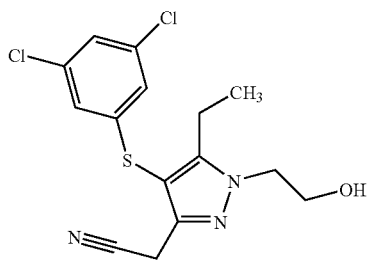

A solution of the protected alcohol of Preparation 39 (70 mg, 0.15 mmol) in tetrahydrofuran (1 ml) was treated with tetrabutylammonium fluoride (1M in THF) (300 μL, 0.30 mmol), at room temperature. After the reaction mixture had stirred for 3 hours the solution was concentrated under reduced pressure. The crude product was purified by flash chromatography on silica gel eluting with cyclohexane:ethyl acetate (3:1, by volume) to afford the title compound (30 mg) as a white solid, m.p. 84–85° C.

$^1$H-NMR (400 MHz, CDCl$_3$): δ=1.15 (m, 3H), 2.75 (q, 2H), 2.83 (t, 1H), 3.63 (s, 2H), 4.12 (m, 2H), 4.22 (m, 2H), 6.82 (s, 2H), 7.10 (s, 1H).

LRMS (electrospray): m/z [M–H$^+$] 354.

Microanalysis: Found: C, 50.86; H, 4.28; N, 11.70. C$_{15}$H$_{15}$Cl$_2$N$_3$OS requires C, 50.57; H, 4.24; N, 11.79%.

Example 78

[4-[(3,5-Dichlorophenyl)sulfonyl]-5-ethyl-1-(2-hydroxyethyl)-1H-pyrazol-3-yl]acetonitrile

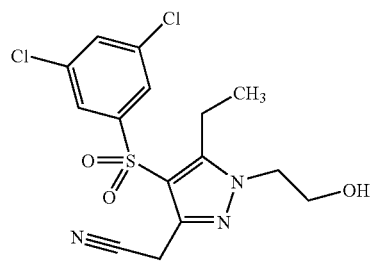

To a stirred solution of the pyrazole (68 mg, 0.14 mmol) of Preparation 39 in methanol (2 ml) was added dichloromethane (3 ml), followed by meta-chloroperoxybenzoic acid (60% w/w) (125 mg, 0.43 mmol). After 18 hours the mixture was partitioned between dichloromethane and water. The aqueous component was separated and further extracted with dichloromethane. The combined organic phases were dried over anhydrous magnesium sulphate, filtered and evaporated under reduced pressure to give a white solid. To a stirred solution of this material in THF (2 ml) was added water (2 ml) followed by acetic acid (2 ml). After 18 hours at room temperature the mixture was partitioned between water and dichloromethane and the aqueous component was separated and further extracted with dichloromethane. The combined organic phases were washed with aqueous sodium bicarbonate solution, dried over anhydrous magnesium sulphate, filtered and evaporated under reduced pressure. The crude product was purified by flash chromatography on silica gel eluting with cyclohexane:ethyl acetate (2:1, by volume) followed by cyclohexane:ethyl actetate (1:1, by volume) to afford the title compound (45 mg) as a white solid, m.p. 117–118° C.

$^1$H-NMR (400 MHz, CDCl$_3$): δ=1.11 (t, 3H), 2.41 (t, 1H), 2.89 (q, 2H), 4.02 (s, 2H), 4.05 (m, 4H), 7.57 (s, 2H), 7.79 (s, 1H).

LRMS (electrospray): m/z [MH$^+$] 388.

Microanalysis: Found: C, 46.39; H, 3.89; N, 10.53. C$_{15}$H$_{15}$Cl$_2$N$_3$O$_3$S requires C, 46.40; H, 3.89; N, 10.82%.

Example 79

2-{4-[(3,5-Dichlorophenyl)sulfanyl]-3,5-diethyl-1H-pyrazol-1-yl}ethanol

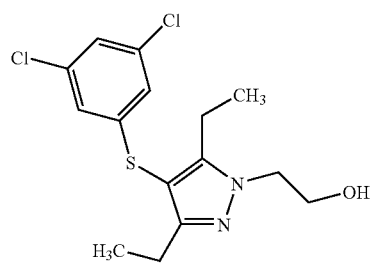

To a stirred solution of the diketone (500 mg, 1.64 mmol) of Preparation 41 in ethanol (1 ml) was added 2-hydroxyethylhydrazine (113 μl, 1.80 mmol). The reaction mixture was heated at 80° C. in a sealed Reacti-vial (Trade Mark) for 4 hours. After cooling, the mixture was concentrated under reduced pressure. The crude product was purified by flash column chromatography on silica gel eluting with pentane: ethyl acetate (3:1, by volume) to afford the title compound as a yellow solid (349 mg), 77–79° C.

$^1$H-NMR (400 MHz, CDCl$_3$): δ=1.04 (t, 3H), 1.18 (t, 3H), 2.52 (q, 2H), 2.62 (q, 2H), 3.64 (s, 1H), 4.03 (m, 2H), 4.17 (m, 2H), 6.79 (s, 2H), 7.02 (s, 1H).

LRMS (electrospray): m/z [MH$^+$] 345.

Microanalysis: Found: C, 51.88; H, 5.20; N, 8.03. C$_{15}$H$_{18}$Cl$_2$N$_2$OS requires C, 52.18; H, 5.25; N, 8.11%.

Example 80

4-(3,5-Dichlorobenzyl)-3-ethyl-1H-pyrazol-5-amine

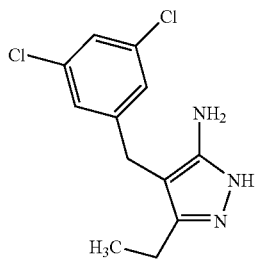

To a stirred solution of the nitrile (500 mg, 1.95 mmol) of Preparation 43 in ethanol (50 ml) was added hydrazine monohydrate (100 mg, 1.95 mmol) and the mixture was heated under reflux. After 15 hours the reaction mixture was cooled and the solvent was removed under reduced pressure. The crude product was purified by flash column chromatography on silica gel eluting with dichloromethane:methanol:ammonia (95:5:0.5, by volume) to afford the title compound as a yellow oil (250 mg).

$^1$H-NMR (400 MHz, CD$_3$OD): δ=1.05 (t, 3H), 2.43 (q, 2H), 3.66 (s, 2H), 7.09 (s, 2H), 7.19 (s, 1H).

LRMS (thermospray): m/z [MH$^+$] 345.

Example 81

Ethyl 4-(3,5-dichlorobenzyl)-3-ethyl-1-(2-hydroxyethyl)-1H-pyrazol-5-ylcarbamate

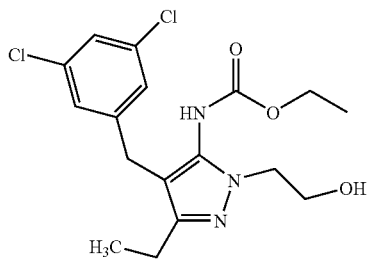

To a stirred solution of the pyrazole (150 mg, 0.35 mmol) of Preparation 44 and triethylamine (70 μl, 0.53 mmol) in dichloromethane (6 ml) was added ethyl chloroformate (40 μl, 0.39 mmol) and the mixture was heated under reflux. After 15 hours the solution was concentrated under reduced pressure. To a solution of the residue in pyridine (2 ml) was added ethyl chloroformate (40 μl, 0.39 mmol). After 7 days at room temperature the solvent was removed under reduced pressure and the residue was filtered through silica, eluting with dichloromethane:methanol:ammonia (98:2:0.2, by volume). The resulting solution was concentrated under reduced pressure and the residue was dissolved in a mixture of tetrahydrofuran (2 ml), acetic acid (2 ml) and water (1 ml). After stirring at room temperature for 15 hours the reaction mixture was partitioned between water and dichloromethane. The aqueous phase was separated and further extracted with dichloromethane. The combined organic phases were washed with brine, dried over anhydrous magnesium sulphate, filtered and evaporated under reduced pressure. The crude product was purified by flash chromatography on silica gel eluting with dichloromethane followed by dichloromethane:methanol:ammonia (95:5:0.5, by volume) to afford the title compound (18 mg) as a colourless oil.

$^1$H-NMR (300 MHz, CDCl$_3$): δ=1.20 (m, 6H), 2.49 (m, 2H), 3.71 (s, 2H), 3.99 (m, 2H), 4.10 (m, 4H), 6.30 (m, 1H), 7.03 (s, 2H), 7.20 (s, 1H).

LRMS (electrospray): m/z [M–H$^+$] 384.

Example 82

N-[4-(3,5-Dichlorobenzyl)-3-ethyl-1-(2-hydroxyethyl)-1H-pyrazol-5-yl]-2-methoxyacetamide

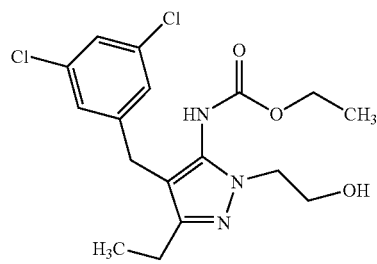

To a stirred mixture of the pyrazole (200 mg, 0.47 mmol) of Preparation 44 and methoxyacetyl chloride (56 mg, 0.52 mmol) in dichloromethane (10 ml) was added triethylamine (72 μl, 0.52 mmol). After 15 hours at room temperature the solvent was removed under reduced pressure and the resulting orange oil was partitioned between dichloromethane and water. The organic phase was separated, washed with brine, dried over anhydrous magnesium sulphate, filtered and evaporated under reduced pressure. To a stirred solution of the residue in acetic acid (2 ml) was added water (1 ml). After 3 days at room temperature the mixture was heated at 60° C. After 4 hours the solution was cooled to room temperature and partitioned between aqueous sodium carbonate solution and dichloromethane. The organic phase was separated and twice washed with water, twice washed with brine, dried over anhydrous magnesium sulphate, filtered and evaporated under reduced pressure. The title compound was isolated as a white solid (100 mg) which was used without further purification, m.p. 142–144° C.

$^1$H-NMR (400 MHz, CF$_3$CO$_2$D): δ=1.38 (t, 3H), 2.90 (q, 2H), 3.52 (s, 3H), 3.88 (s, 2H), 4.16 (s, 2H), 4.21 (m, 2H), 4.58 (m, 2H), 7.03 (s, 2H), 7.30 (s, 1H).

LRMS (thermospray): m/z [MH$^+$] 386.

Example 83

2-[4-(3,5-Dichlorobenzyl)-5-(dimethylamino)-3-ethyl-1H-pyrazol-1-yl]ethanol

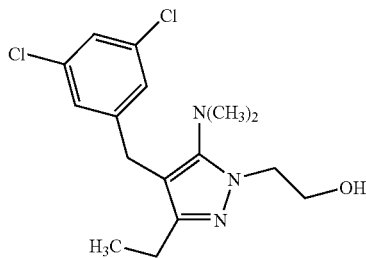

A stirred solution of the pyrazole (300 mg, 0.07 mmol) of Preparation 44 and paraformaldehyde (46 mg, 1.54 mmol) in formic acid (2 ml) was heated under reflux. After 15 hours the mixture was cooled and the solvent was removed under reduced pressure. The crude product was purified by flash chromatography on silica gel eluting with dichloromethane followed by dichloromethane:methanol (99:1, by volume) to afford the title compound (50 mg) as a colourless oil.

$^1$H-NMR (400 MHz, CDCl$_3$): δ=1.09 (t, 3H), 2.38 (q, 2H), 2.62 (s, 6H), 3.77 (s, 2H), 3.91 (m, 2H), 4.04 (m, 2H), 4.23 (t, 1H), 6.95 (s, 2H), 7.17 (s, 1H).

LRMS (thermospray): m/z [MH$^+$] 342.

Examples 84 and 85

Ethyl 4-(3,5-dichlorobenzyl)-1-(2-hydroxyethyl)-5-methyl-1H-pyrazole-3-carboxylate (Examples 84) and ethyl 4-(3,5-dichlorobenzyl)-1-(2-hydroxyethyl)-3-methyl-1H-pyrazole-5-carboxylate (Example 85)

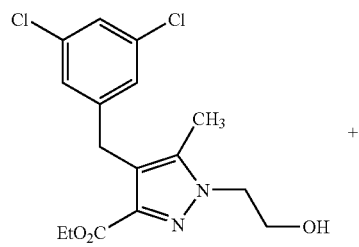

+

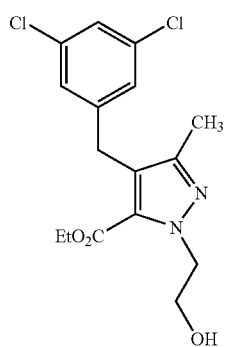

The title compounds were prepared by a similar method to that of Examples 27 and 28 using the β-diketone of Preparation 22. The crude product was purified by flash chromatography on silica gel eluting with pentane:ethyl acetate (1:1, by volume) to afford the two isomers.

Less Polar Isomer (Example 85):

Shown to be ethyl 4-(3,5-dichlorobenzyl)-1-(2-hydroxyethyl)-3-methyl-1H-pyrazole-5-carboxylate by nOe experiments. Isolated as a white solid, m.p. 105.8–107.5° C.

$^1$H-NMR (300 MHz, CDCl$_3$): δ=1.35 (t, 3H), 2.20 (s, 3H), 3.10 (t, 1H), 4.00 (s, 2H), 4.01 (m, 2H), 4.30 (q, 2H), 4.67 (m, 2H), 6.98 (s, 2H), 7.20 (s, 1H).

LRMS (thermospray): m/z [MH$^+$] 357.

Microanalysis: Found: C, 53.81; H, 5.02; N, 7.59. $C_{16}H_{18}N_2O_3$ requires C, 53.80; H, 5.08; N, 7.84%.

More Polar Isomer (Example 84):

Ethyl 4-(3,5-dichlorobenzyl)-1-(2-hydroxyethyl)-5-methyl-1H-pyrazole-3-carboxylate was isolated as a white solid, 110.7–112.4° C.

$^1$H-NMR (300 MHz, CDCl$_3$): δ=1.35 (t, 3H), 2.21 (s, 3H), 2.70 (brs, 1H), 4.01 (m, 4H), 4.22 (m, 2H), 4.33 (q, 2H), 7.00 (s, 2H), 7.19 (s, 1H).

LRMS (thermospray): m/z [MH$^+$] 357.

Microanalysis: Found: C, 53.53; H, 5.06; N, 7.59. $C_{16}H_{18}N_2O_3$ requires C, 53.80; H, 5.08; N, 7.84%.

Example 86 tert-Butyl 4-(3,5-dichlorobenzyl)-1-(2-hydroxyethyl)-5-methyl-1H-pyrazol-3-ylcarbamate

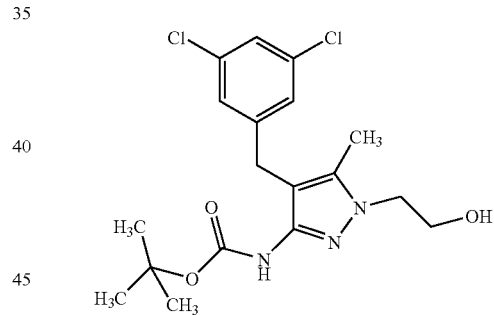

A suspension of the carboxylic acid of Preparation 23 (550 mg, 1.67 mmol) in tert-butanol (8.35 ml) was treated with triethylamine (244 μL, 1.84 mmol) and diphenylphosphoryl azide (396 μL, 1.84 mmol) and the reaction mixture was stirred under reflux for 18 hours, under a nitrogen atmosphere. After cooling, the solution was concentrated under reduced pressure. The residue was diluted with water and extracted with ethyl acetate (×3). The combined organic extracts were dried over anhydrous magnesium sulphate, filtered and evaporated under reduced pressure. The crude product was purified by flash chromatography on silica gel eluting with pentane:ethyl acetate (1:2, by volume) followed by dichloromethane:methanol:ammonia (95:5:0.5, by volume) to afford the title compound (160 mg).

$^1$H-NMR (300 MHz, CDCl$_3$): δ=1.44 (s, 9H), 2.17 (s, 3H), 3.42 (s, 1H), 3.77 (s, 2H), 3.92 (m, 2H), 4.02 (m, 2H), 6.43 (s, 1H), 6.99 (s, 2H), 7.18 (s, 1H).

LRMS (thermospray): m/z [MH$^+$] 400.

Example 87

2-[3-Amino-4-(3,5-dichlorobenzyl)-5-methyl-1H-pyrazol-1-yl]ethanol

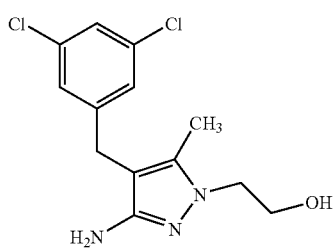

A solution of the protected amine of Example 86 (50 mg, 0.13 mmol) in 1,4-dioxan was treated with 4M hydrogen chloride in 1,4-dioxan (320 µL, 1.25 mmol) and stirred at room temperature for 2 days. The solution was concentrated under reduced pressure. The residue was diluted with water (15 ml) and extracted with ethyl acetate (3×10 ml). The combined organic phases were dried over anhydrous magnesium sulphate, filtered and evaporated under reduced pressure to afford the title compound as a white solid and as the hydrochloride salt (19.5 mg).

$^1$H-NMR (300 MHz, $d_6$-DMSO): δ=2.13 (s, 3H), 3.59 (m, 2H), 3.69 (s, 2H), 3.89 (m, 2H), 7.09 (s, 2H), 7.25 (s, 1H).
LRMS (thermospray): m/z [MH$^+$] 300.

Example 88

Ethyl [4-(3,5-dichlorobenzyl)-5-methoxy-3-methyl-1H-pyrazol-1-yl]acetate

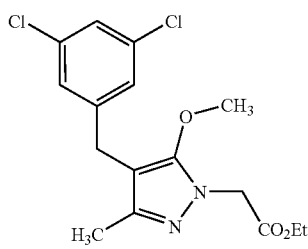

A suspension of the ester of Preparation 26 (100 mg, 0.29 mmol) in toluene (4 ml) was treated with triphenylphosphine (115 mg, 0.44 mmol), followed by methanol (15 µL, 0.30 mmol) then diethyl azodicarboxylate (69 µL, 0.44 mmol) and the resulting mixture was stirred at room temperature, under a nitrogen atmosphere for 18 hours. The reaction mixture was diluted with ethyl acetate and washed with 10% aqueous sodium carbonate solution. The organic phase was dried over anhydrous magnesium sulphate, filtered and evaporated under reduced pressure. The resulting oil was purified by flash chromatography on silica gel eluting with cyclohexane:ethyl actetate (3:1, by volume) to afford the title compound (73 mg) as a colourless oil, which solidified under reduced pressure.

$^1$H-NMR (300 MHz, CDCl$_3$): δ=1.31 (t, 3H), 2.08 (s, 3H), 3.78 (s, 2H), 3.81 (s, 3H), 4.27 (q, 2H), 4.73 (s, 2H), 7.03 (s, 2H), 7.20 (s, 1H).
LRMS (thermospray): m/z [MH$^+$] 357.

Microanalysis: Found: C, 53.66; H, 5.08; N, 7.84. $C_{16}H_{18}Cl_2N_2O_3$ requires C, 53.80; H, 5.08; N, 7.84%.

Example 89

2-[5-Amino-4-(3,5-dichlorobenzyl)-3-ethyl-1H-pyrazol-1-yl]ethanol

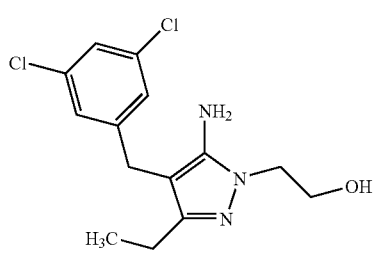

To a stirred solution of the nitrile (500 mg, 1.95 mmol) of Preparation 43 in ethanol (50 ml) was added 2-hydroxyethylhydrazine (153 mg, 1.95 mmol) and the mixture was heated under reflux. After 15 hours the mixture was concentrated under reduced pressure. The crude product was purified by flash chromatography on silica gel eluting with dichloromethane:methanol:ammonia (95:5:0.5, by volume) to afford the title compound (450 mg) as a white solid, m.p. 135° C.

$^1$H-NMR (400 MHz, DMSO): δ=0.90 (t, 3H), 2.19 (q, 2H), 3.58 (m, 4H), 3.82 (t, 2H), 4.82 (t, 1H), 4.90 (s, 2H), 7.07 (s, 2H), 7.30 (s, 1H).
LRMS (thermospray): m/z [MH$^+$] 314.
Microanalysis: Found: C, 53.33; H, 5.50; N, 13.20. $C_{14}H_{17}Cl_2N_3O$ requires C, 53.52; H, 5.45; N, 13.37%.

Example 90

5-{[3,5-Diethyl-1-(2-hydroxyethyl)-1H-pyrazol-4-yl]methyl}isophthalonitrile

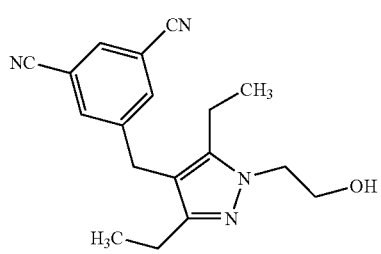

2-Hydroxyethylhydrazine (34 mg, 0.44 mmol) was added to a stirred solution of the diketone (105 mg, 0.4 mmol) of Preparation 45 in glacial acetic acid (3 ml) at room temperature under nitrogen. After stirring for 3 days the acetic acid was evaporated under reduced pressure and the residue was partitioned between 10% aqueous potassium carbonate solution (40 ml) and dichloromethane (40 ml). The organic phase was separated, dried over anhydrous magnesium sulphate, filtered and evaporated under reduced pressure. The crude product was purified by flash chromatography on silica gel eluting with dichloromethane:methanol (98:2, by volume) to give the title compound as a white solid (76 mg) m.p. 115–117° C.

$^1$H-NMR (400 MHz, CDCl$_3$): δ=1.0 (3H, t), 1.1 (3H, t), 1.55 (1H, br. s), 2.37 (2H, q), 2.48 (2H, q), 3.79 (2H, s), 4.02 (2H, m), 4.08 (2H, m), 7.55 (2H, s), 7.71 (1H, s).

LRMS (thermospray): m/z [MH$^+$] 309.

Microanalysis: Found: C, 69.64; H, 6.54; N, 18.06. C$_{16}$H$_{16}$N$_2$O$_2$ requires C, 70.11; H, 6.54; N, 18.17%.

Example 91

5-[(3,5-Diethyl-1H-pyrazol-4-yl)methyl]isophthalonitrile

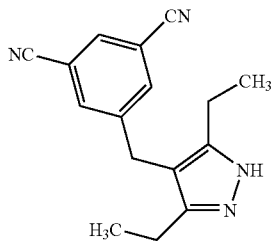

Hydrazine hydrate (49 μL, 1 mmol) was added to a stirred solution of the diketone (237 mg, 0.9 mmol) of Preparation 45 in glacial acetic acid (3 ml) at room temperature under nitrogen. After stirring for 3 days the acetic acid was evaporated under reduced pressure and the residue was partitioned between 10% aqueous potassium carbonate solution (40 ml) and dichloromethane (40 ml). The organic phase was separated, dried over anhydrous magnesium sulphate, filtered and evaporated under reduced pressure. The crude product was purified by flash chromatography on silica gel eluting with dichloromethane:methanol (98:2, by volume) to give the title compound as a white solid (188 mg) m.p. 141–143° C.

$^1$H-NMR (400 MHz, CDCl$_3$): δ=1.15 (6H, t), 2.47 (4H, q), 3.82 (2H, s), 7.58 (2H, s), 7.73 (1H, s).

LRMS (thermospray): m/z [MH$^+$] 265.

Example 92

5-{[1-(2-Aminoethyl)-3,5-diethyl-1H-pyrazol-4-yl]methyl}isophthalonitrile

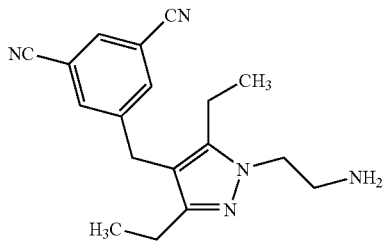

A stirred mixture of the pyrazole (106 mg, 0.4 mmol) of Example 91 and 2-chloroethylamine hydrochloride (70 mg, 0.6 mmol) was heated at 150° C. under nitrogen for 18 hours. After cooling the mixture was partitioned between 10% aqueous potassium carbonate (40 ml) and dichloromethane (40 ml) and the organic layer was dried over magnesium sulphate, filtered and evaporated under reduced pressure. The crude product was purified by flash chromatography on silica gel eluting with a solvent gradient of dichloromethane:methanol (98:2, by volume) and then dichloromethane:methanol:0.880 ammonia (95:5:0.5, by volume) to give the title compound as a white solid (51 mg) m.p. 100–105° C.

$^1$H-NMR (400 MHz, CDCl$_3$): δ=1.02 (3H, t), 1.09 (3H, t), 1.49 (2H, br. s), 2.38 (2H, q), 2.52 (2H, q), 3.13 (2H, t), 3.78 (2H, s), 4.04 (2H, t), 7.58 (2H, s), 7.74 (1H, s).

LRMS (electrospray): m/z [MH$^+$] 308.

Example 93

2-{4-[(3,5-Dibromophenyl)sulfanyl]-3,5-diethyl-1H-pyrazol-1-yl}ethanol

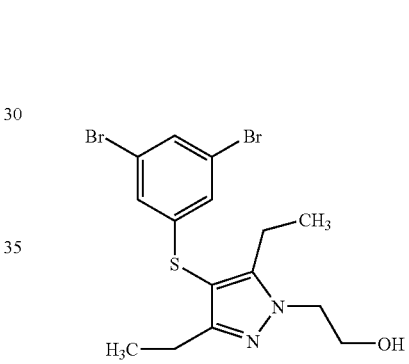

2-Hydroxyethylhydrazine (0.43 mL, 6.3 mmol) was added to a suspension of the diketone (2.5 g, 6.3 mmol) from Preparation 49 in glacial acetic acid (2 ml) and the mixture was stirred for three days. 2-Hydroxyethylhydrazine (0.5 mL, 7.3 mmol) was added and the mixture was stirred for 16 hours. The mixture was concentrated under reduced pressure and the residue was partitioned between ethyl acetate (100 ml) and water (150 ml). The aqueous layer was extracted with ethyl acetate (100 ml) and the combined organic layers were washed with brine (100 ml), dried over magnesium sulphate, filtered and concentrated under reduced pressure. The crude product was purified by flash chromatography on silica gel eluting with dichloromethane gradually changing to dichloromethane:ethyl acetate (17:3, by volume) to provide the title compound (1.3 g) as a colourless oil.

$^1$H-NMR (300 MHz, CDCl$_3$): δ=1.11 (t, 3H), 1.20 (t, 3H), 2.6 (q, 2H), 2.7 (q, 2H), 4.10 (m, 2H), 4.18 (m, 2H), 7.02 (s, 2H), 7.37 (s, 1H).

LRMS (thermospray): m/z [MH$^+$] 435.

Microanalysis: Found: C, 41.29; H, 4.17; N, 6.36. C$_{15}$H$_{18}$Br$_2$N$_2$OS requires C, 41.49; H, 4.18; N, 6.45%.

Example 94

5-{[3,5-Diethyl-1-(2-hydroxyethyl)-1H-pyrazol-4-yl]sulfanyl}isophthalonitrile

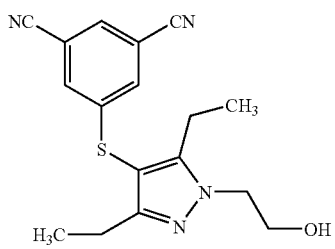

5-{[1-(2-{[tert-Butyl(dimethyl)silyl]oxy}ethyl)-3,5-diethyl-1H-pyrazol-4-yl]sulfanyl}isophthalonitrile (180 mg, 0.4 mmol) (Preparation 51) was treated with tetrabutylammonium fluoride (1M solution in tetrahydrofuran, 0.8 ml, 0.8 mmol) and the resulting solution was stirred for 2½ hours. The mixture was concentrated under reduced pressure to give a brown oil. The crude product was purified by flash chromatography on silica gel eluting with ethyl acetate: dichloromethane (1:4, by volume) to provide the title compound (70 mg) as a yellow oil.

$^1$H-NMR (300 MHz, CDCl$_3$): δ=1.11 (t, 3H), 1.19 (t, 3H), 2.56 (q, 2H), 2.69 (q, 2H), 3.50 (br. s, 1H), 4.12 (m, 2H), 4.22 (m, 2H), 7.41 (s, 2H), 7.61 (s, 1H).

LRMS (electrospray): m/z [MH$^+$] 327.

The following Preparations describe the preparation of certain intermediates used in the preceding Examples.

Preparation 1

3-(3,5-Dichlorobenzyl)-5-methyl-2,4-hexanedione

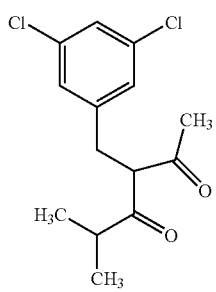

Method A:

5% Palladium on barium sulphate (10 mg) was added to a stirred solution of the more polar alkene isomer of Preparation 8 (100 mg) in ethanol (2.5 ml) and the resulting mixture was stirred under an atmosphere of hydrogen (103.4 kPa, 15 psi) for 3 hours. The mixture was filtered through a filter aid (Arbocel (Trade Mark)) (caution—fire hazard) and the filtrate was concentrated under reduced pressure. The residue was purified by flash chromatography on silica gel eluting with pentane:ethyl acetate (10:1, by volume) to give the title compound (72 mg) as a 43:57 mixture with its enol tautomer as estimated by $^1$H-NMR and as a yellow oil.

$^1$H-NMR (400 MHz, CDCl$_3$): δ=1.03 (d, 6H, diketone and enol), 2.02 (s, 3H, enol), 2.11 (s, 3H, diketone), 2.52 (heptet, 1H, diketone), 2.61 (heptet, 1H, d, enol), 3.00 (dd, 1H, diketone), 3.06 (dd, 1H, diketone), 3.60 (s, 2H, enol), 4.00 (t, 1H, diketone), 6.98 and 7.00 (2s, 2×2H, diketone and enol), 7.18 (s, 1H, diketone and enol).

LRMS (thermospray): m/z [MH$^+$] 304.

Method B:

The less polar alkene isomer of Preparation 8 was reduced in the same way as for the more polar isomer in Method A above but stirring the mixture for 9 hours and flash chromatography on silica gel eluting with a solvent gradient of pentane:ether (20:1, by volume) then pentane:ether (10:1, by volume) to give the title compound as a yellow oil.

Preparation 2

3-(3,5-Difluorobenzyl)-5-methyl-2,4-hexanedione

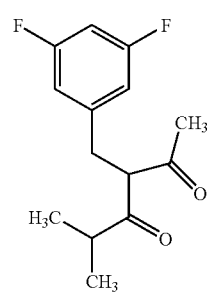

Method A:

5% Palladium on barium sulphate (56 mg) was added to a stirred solution of the more polar alkene isomer of Preparation 11 (560 mg) in ethanol (16 ml) and the resulting mixture was stirred under an atmosphere of hydrogen (103.4 kPa, 15 psi) for 4 hours. The mixture was filtered through a filter aid (Arbocel (Trade Mark)) (caution—fire hazard) and the filtrate was concentrated under reduced pressure. The residue was purified by flash chromatography on silica gel eluting with pentane:ether (10:1, by volume) to give the title compound (513.1 mg) as a 35:65 mixture with its enol tautomer as estimated by $^1$H-NMR as a yellow oil.

$^1$H-NMR (400 MHz, CDCl$_3$): δ=1.03 (d, 6H, diketone and enol), 2.03 (s, 3H, enol), 2.13 (s, 3H, diketone), 2.55 (heptet, 1H, diketone), 2.65 (heptet, 1H, enol), 3.03 (dd, 1H, diketone), 3.11 (dd, 1H, diketone), 3.65 (s, 2H, enol), 4.03 (t, 1H, diketone), 6.65 (m, 3H, diketone and enol).

LRMS (electrospray): m/z [MNa$^+$] 277.

Method B:

The less polar alkene isomer of Preparation 11 was reduced in the same way as for the more polar isomer in Method A above but stirring the mixture for 25 hours to give the title compound as a yellow oil.

Preparation 3

3-(3-Fluorobenzyl)-5-methyl-2,4-hexanedione

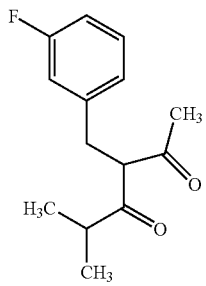

The title compound was prepared by a method similar to that of Preparation 2 using the alkene isomers of Preparation 12 to give the title compound as a 38:62 mixture with its enol tautomer as estimated by $^1$H-NMR as a yellow oil.

$^1$H-NMR (400 MHz, CDCl$_3$): δ=1.06 (d, 6H, diketone and enol), 2.06 (s, 3H, enol), 2.16 (s, 3H, diketone), 2.55 (heptet, 1H, diketone), 2.73 (heptet, 1H, enol), 3.08 (dd, 1H, diketone), 3.16 (dd, 1H, diketone), 3.68 (s, 2H, enol), 4.10 (t, 1H, diketone), 6.89 (m, 3H, diketone and enol), 7.27 (m, 1H, diketone and enol).

LRMS (electrospray): m/z [MNa$^+$] 259.

Preparation 4

3-(3,5-Dichlorobenzyl)-2,4-pentanedione

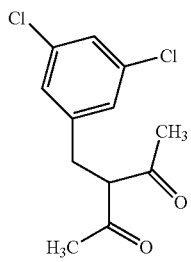

To a solution of the alkene of Preparation 9 (6.4 g, 24.9 mmol) in ethanol (100 ml) and ethyl acetate (40 ml) was added 5% palladium on barium sulphate (640 mg) and the resulting mixture was stirred under an atmosphere of hydrogen (103.4 kPa, 15 psi) for 18 hours. The mixture was filtered through a filter aid (Arbocel (Trade Mark)) (caution—fire hazard) under nitrogen and the filtrate was concentrated under reduced pressure. The residue was purified by flash chromatography on silica gel eluting with a solvent gradient of pentane:ethyl acetate (10:1, by volume) and then pentane:ethyl acetate (7:1, by volume) to give the title compound (5.3 g) as a mixture with its enol tautomer as shown by $^1$H-NMR as a yellow powder, m.p. 85–87° C.

$^1$H-NMR (400 MHz, CDCl$_3$): δ=2.02 (s, 6H, enol), 2.15 (s, 6H, diketone), 3.06 (d, 2H, diketone), 3.60 (s, 2H, enol), 3.93 (t, 1H, diketone), 7.00 (s, 2H, enol), 7.03 (s, 2H, diketone), 7.21 (s, 1H, diketone and enol), 16.78 (s, 1H, enol).

LRMS (electrospray): m/z [M–H$^+$] 257.
Microanalysis: Found: C, 55.91; H, 4.72. C$_{12}$H$_{12}$Cl$_2$O$_2$ requires C, 55.62; H, 4.67.

Preparation 5

4-(3,5-Dichlorobenzyl)-3,5-heptanedione

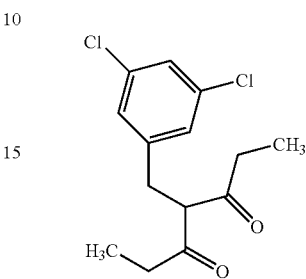

The title compound was prepared by a method similar to that of Preparation 1, Method B using the alkene of Preparation 14 and purified by flash chromatography on silica gel eluting with a solvent gradient of pentane:ethyl acetate (20:1, by volume) and then pentane:ethyl acetate (10:1, by volume) to give the title compound as a mixture with its enol tautomer as estimated by $^1$H-NMR and as an orange oil. A small amount (ca. 10%) of dechlorinated impurities presumably arising from over reduction were detected by $^1$H-NMR. This over reduction could probably be avoided by using the alternative reduction procedure of Preparation 6.

$^1$H-NMR (400 MHz, CDCl$_3$): δ=1.00 (m, 6H, diketone and enol), 2.40 (m, 4H, diketone and enol), 3.11 (d, 2H, diketone), 3.64 (d, 2H, enol), 3.97 (t, 1H, diketone), 7.03 (d, 2H), 7.22 (s, 1H), 17.02 (s, 1H, enol).

Preparation 6

3-(3,5-Dichlorobenzyl)-1,1,1-trifluoro-2,4-pentanedione

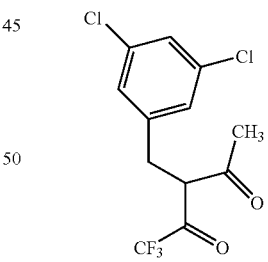

To a solution of a mixture of the alkenes of Preparation 13 (100 mg, 0.321 mmol) in dichloromethane (3 ml) was added diphenylsilane (88.6 mg, 0.481 mmol), tetrakis(triphenylphospine)palladium(0) and zinc chloride (8 mg, 0.06 mmol) and the resulting mixture was stirred under nitrogen at room temperature for 3 days. The mixture was applied directly to a silca gel column and purified by flash chromatography eluting with a solvent gradient of dichloromethane:pentane (1:3, by volume) and then dichloromethane:pentane (1:2, by volume) to give the title compound (78 mg) as a mixture with its enol tautomer as shown by $^1$H-NMR and as a pale yellow oil.

$^1$H-NMR (300 MHz, CDCl$_3$): δ=(enol only, signals for diketone not assigned) 2.14 (s, 3H), 3.78 (s, 2H), 7.02 (2, 2H), 7.09 (m, 1H), 16.29 (br. s, 1H).

LRMS (electrospray): m/z [M−H$^+$] 311.

Preparation 7

3-(3-Chlorobenzyl)-5-methyl-2,4-hexanedione

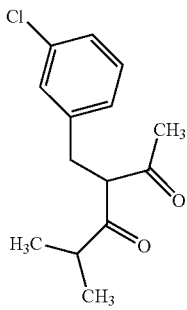

The title compound was prepared by a similar method to that of Preparation 6 using a mixture of the alkenes of Preparation 10, being purified by flash chromatography eluting with pentane:ethyl acetate (3:1, by volume) and being obtained as a mixture with its enol tautomer as shown by $^1$H-NMR as a yellow oil.

$^1$H-NMR (300 MHz, CDCl$_3$): δ=0.97–1.01 (m, 6H, diketone and enol), 2.02 and 2.10 (2s, 2×3H, diketone and enol), 2.53 and 2.66 (2m, 2×1H, diketone and enol), 3.07 (m, 2H, diketone), 3.61 (s, 2H, enol), 4.05 (m, 1H, diketone), 7.08 (m, 4H, diketone and enol).

Preparation 8

(3E)-3-(3,5-Dichlorobenzylidene)-5-methyl-2,4-hexanedione and (3Z)-3-(3,5-dichlorobenzylidene)-5-methyl-2,4-hexanedione

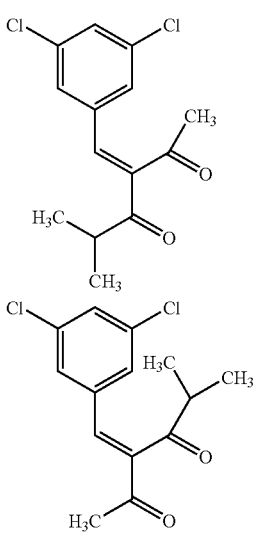

A mixture of 5-methyl-2,4-hexanedione (*J. Am. Chem. Soc.*, 1980, 2095–6.) (1.84 g, 14.33 mmol), 3,5-dichlorobenzaldehyde (2.5 g, 14.33 mmol), glacial acetic acid (214 μL, 3.73 mmol), piperidine (29 μL, 0.29 mmol), dry toluene (10.2 ml) and powdered 3 Å molecular sieves (100 mg) was heated under reflux under nitrogen for 24 hours. A Dean-Stark trap was attached to the reaction and heating under reflux was continued for 3 hours, during which time the toluene evaporated from the reaction. The residue was diluted with dichloromethane (80 ml) and filtered to remove molecular sieves. The filtrate was washed with water (80 ml), dried over magnesium sulphate and concentrated under reduced pressure. The residue was purified by flash chromatography on silica gel eluting with pentane:ether (10:1, by volume) to give the less polar title compound (510.6 mg) as a yellow oil.

$^1$H-NMR (400 MHz, CDCl$_3$): δ=1.19 (d, 6H), 2.29 (s, 3H), 3.19 (heptet, 1H), 7.24 (s, 2H), 7.34 (s, 1H), 7.40 (s, 1H).

LRMS (thermospray): m/z [MNH$_4^+$] 302.

Further eluton of the same column gave the more polar title compound (993.3 mg) as a yellow oil.

$^1$H-NMR (400 MHz, CDCl$_3$): δ=1.05 (d, 6H), 2.40 (s, 3H), 2.58 (heptet, 1H), 7.24 (s, 2H), 7.39 (s, 1H), 7.45 (s, 1H).

LRMS (thermospray): m/z [MNH$_4^+$] 302.

Preparation 9

3-(3,5-Dichlorobenzylidene)-2,4-pentanedione

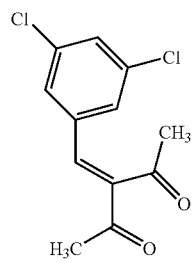

Glacial acetic acid (0.49 ml, 8.6 mmol) and piperidine (57 μL, 0.6 mmol) were added to a stirred solution of 2,4-pentanedione (2.86 g, 28.6 mmol) and 3,5-dichlorobenzaldehyde (5.00 g, 28.6 mmol) in toluene (25 ml) and the mixture was heated under reflux using a Dean-Stark trap for 18 hours. After cooling, the mixture was concentrated under reduced pressure and the residue was purified by flash chromatography on silica gel eluting with pentane:ethyl acetate (10:1, by volume) to give the title compound (6.5 g) as a red/brown solid, m.p. 85–87° C.

$^1$H-NMR (400 MHz, CDCl$_3$): δ=2.22 (s, 3H), 2.39 (s, 3H), 7.21 (s, 2H), 7.26 (s, 1H), 7.35 (s, 1H).

LRMS (thermospray): m/z [MNH$_4^+$] 274.

Microanalysis: Found: C, 55.93; H, 3.81. C$_{12}$H$_{10}$Cl$_2$O$_2$ requires C, 56.06; H, 3.92.

Preparation 10

(3E)-3-(3–Chlorobenzylidene)-5-methyl-2,4-hexanedione and (3Z)-3-(3-chlorobenzylidene)-5-methyl-2,4-hexanedione

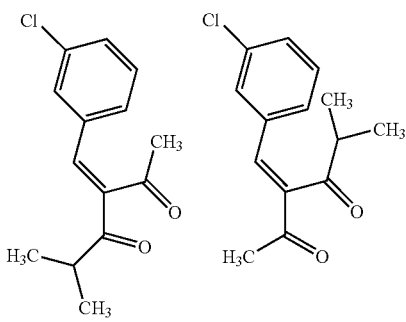

The title compounds were prepared by a similar method to that of Preparation 9 using 5-methyl-2,4-hexanedione (*J. Am. Chem. Soc.*, 1980, 2095–6) and 3-chlorobenzaldehyde and were obtained as yellow oils.

Less Polar Isomer:
$^1$H-NMR (400 MHz, CDCl$_3$): δ=1.16 (d, 6H), 2.24 (s, 3H), 3.18 (m, 1H), 7.30 (m, 6H).
LRMS (thermospray): m/z [MNH$_4^+$] 268.

More Polar Isomer:
$^1$H-NMR (400 MHz, CDCl$_3$): δ=1.02 (d, 6H), 2.39 (s, 3H), 2.55 (m, 1H), 7.31 (m, 5H), 7.50 (s, 1H).
LRMS (thermospray): m/z [MNH$_4^+$] 268.

Preparation 11

(3E)-3-(3,5-Difluorobenzylidene)-5-methyl-2,4-hexanedione and (3Z)-3-(3,5-difluorobenzylidene)-5-methyl-2,4-hexanedione

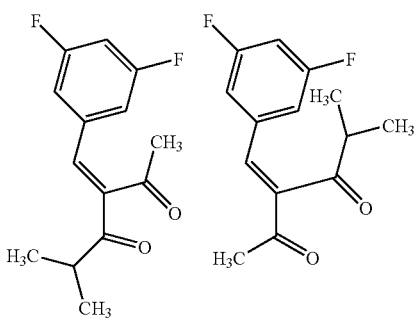

The title compounds were prepared by a similar method to that of Preparation 9 using 5-methyl-2,4-hexanedione (*J. Am. Chem. Soc.*, 1980, 2095–6) and 3,5-difluorobenzaldehyde and purified by flash chromatography on silica gel eluting with a solvent gradient of pentane:ether (20:1, by volume) and then pentane:ethyl acetate (10:1, by volume) to give the less polar title compound as a yellow oil.

Less Polar Isomer:
$^1$H-NMR (400 MHz, CDCl$_3$): δ=1.15 (d, 6H), 2.27 (s, 3H), 3.19 (heptet, 1H), 6.92 (m, 3H), 7.32 (s, 1H).
LRMS (electrospray): m/z [MNH$_4^+$] 253.

Further elution of the same column gave the more polar title compound as a yellow oil.

More Polar Isomer:
$^1$H-NMR (400 MHz, CDCl$_3$): δ=1.03 (d, 6H), 2.40 (s, 3H), 2.56 (heptet, 1H), 6.96 (m, 3H), 7.44 (s, 1H).
LRMS (electrospray): m/z [MNH$_4^+$] 253.

Preparation 12

(3E)-3-(3-Fluorobenzylidene)-5-methyl-2,4-hexanedione and (3Z)-3-(3-fluorobenzylidene)-5-methyl-2,4-hexanedione

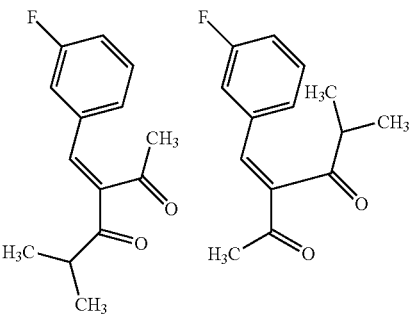

The title compounds were prepared by a similar method to that of Preparation 9 using 5-methyl-2,4-hexanedione (*J. Am. Chem. Soc.*, 1980, 2095–6) and 3-fluorobenzaldehyde and purified by flash chromatography on silica gel eluting with a solvent gradient of pentane:ether (20:1, by volume) and then pentane:ethyl acetate (10:1, by volume) to give the less polar title compound as a yellow oil.

Less Polar Isomer:
$^1$H-NMR (300 MHz, CDCl$_3$): δ=1.23 (d, 6H), 2.29 (s, 3H), 3.24 (heptet, 1H), 7.13 (m, 3H), 7.39 (m, 1H), 7.44 (s, 1H).
LRMS (thermospray): m/z [MNH$_4^+$] 235.

Further elution of the same column gave the more polar title compound as a yellow oil.

More Polar Isomer:
$^1$H-NMR (300 MHz, CDCl$_3$): δ=1.06 (d, 6H), 2.42 (s, 3H), 2.60 (heptet, 1H), 7.11 (m, 3H), 7.35 (m, 1H), 7.55 (s, 1H).
LRMS (thermospray): m/z [MNH$_4^+$] 235.

Preparation 13

(3E)-3-(3,5-Dichlorobenzylidene)-1,1,1-trifluoro-2,4-pentanedione and (3Z)-3-(3,5-dichlorobenzylidene)-1,1,1-trifluoro-2,4-pentanedione

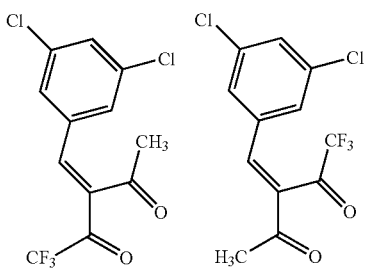

Glacial acetic acid (0.425 ml, 7.423 mmol) and piperidine (57 µL, 0.571 mmol) were added to a stirred solution of 1,1,1-trifluoro-2,4-pentanedione (4.40 g, 28.55 mmol) and 3,5-dichlorobenzaldehyde (5.0 g, 28.55 mmol) in toluene (20 ml) and the mixture was heated under reflux using a Dean-Stark trap for 16 h. After cooling the mixture was washed with brine (30 ml), dried over magnesium sulphate and concentrated under reduced pressure to give a dark brown oil (9.1 g) which was purified by flash chromatography on silica gel eluting with a solvent gradient of pentane:ether (10:1, by volume), pentane:ether (5:1, by volume) and then dichloromethane:pentane (1:1, by volume) to give the crude products (4.2 g) as a brown oil. The crude products were further purified by flash chromatography on silica gel eluting with a solvent gradient of dichloromethane:pentane (1:4, by volume) and then dichloromethane:pentane (1:3, by volume) to give a mixture of the title compounds (683 mg) as shown by thin layer chromatography using dichloromethane:pentane (1:1, by volume), major isomer $R_f$ 0.54, minor isomer $R_f$ 0.17, and as a pale yellow oil.

$^1$H-NMR (300 MHz, CDCl$_3$): δ=2.49 (s, 3H), 7.23 (s, 2H), 7.46 (s, 1H), 7.66 (s, 1H).

LRMS (electrospray): m/z [MH$^+$] 328.

Preparation 14

4-(3,5-Dichlorobenzylidene)-3,5-heptanedione

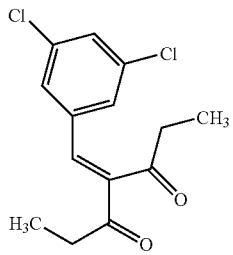

The title compound was prepared by a method similar to that of Preparation 13 using 3,5-heptanedione and was purified by chromatography on silica gel eluting with pentane:ether (10:1, by volume) to give a product which was triturated with pentane to give the title compound as a white solid, m.p. 80–82° C.

$^1$H-NMR (300 MHz, CDCl$_3$): δ=1.16 (m, 6H), 2.50 (q, 2H), 2.73 (q, 2H), 7.22 (s, 2H), 7.37 (m, 2H).

LRMS (thermospray): m/z [MH$^+$] 285.

Microanalysis: Found: C, 58.97; H, 4.95. C$_{14}$H$_{14}$Cl$_2$O$_2$ requires C, 58.98; H, 4.93.

Preparation 15

3-[(3,5-Dichlorophenyl)sulfanyl]-2,4-pentanedione

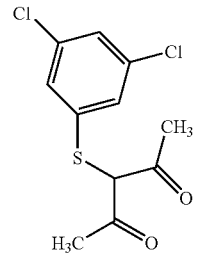

3-Chloro-2,4-pentanedione (723 µL, 6.07 mmol) and then sodium iodide (910 mg, 6.07 mmol) were added to a stirred suspension of 3,5-dichlorothiophenol (1.09 g, 6.07 mmol) and potassium carbonate (923 mg, 6.68 mmol) in acetone (30 ml), at room temperature, in a flask equipped with a calcium chloride drying tube. The mixture became yellow, then orange and finally red accompanied by a slight exotherm and was stirred for 23 hours at room temperature. The mixture was diluted with water (20 ml) and concentrated under reduced pressure in a fumehood (Caution: possible residual lachrymator) to remove acetone. The residue was diluted with 2M hydrochloric acid (20 ml) and extracted with dichloromethane (1×40 ml, 2×20 ml). The combined organic phases were washed with brine (20 ml), dried over anhydrous magnesium sulphate, filtered and evaporated under reduced pressure to leave an orange solid (1.66 g). The crude product was purified by flash chromatography on silica gel eluting with pentane:diethyl ether (99:1, by volume) to give the title compound (807 mg) as a yellow solid m.p. 79–81° C.

$^1$H-NMR (400 MHz, CDCl$_3$): δ=2.30 (2, 6H), 6.91 (s, 2H), 7.09 (s, 1H).

LRMS (thermospray): m/z [MNH$_4^+$] 294.

Microanalysis: Found: C, 47.45; H, 3.54; C$_{11}$H$_{10}$Cl$_2$O$_2$S requires C, 47.67; H, 3.64%.

Preparation 16

(3E and 3Z)-3-(3,5-Dichlorobenzylidene)-1,1,1-trifluoro-2,4-hexanedione

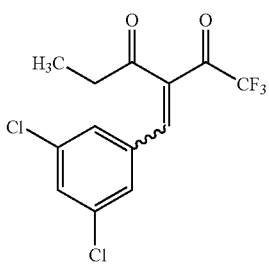

The title compound was prepared by a similar method to that of Preparation 9 using 1,1,1-trifluorohexane-2,4-dione and 3,5-dichlorobenzaldehyde. The crude product was purified by flash chromatography on silica gel eluting with a solvent gradient of pentane gradually changing to pentane:ethyl acetate (5:1, by volume). The product was further purified by flash chromatography eluting with dichloromethane:pentane (1:10, by volume) to afford a mixture of the title compounds (500 mg) as a yellow oil.

$^1$H-NMR (300 MHz, CDCl$_3$): δ=1.23 (t, 3H), 2.80 (q, 2H), 7.32 (s, 2H), 7.52 (s, 1H), 7.74 (s, 1H).

Preparation 17

3-(3,5-Dichlorobenzyl)-1,1,1-trifluoro-2,4-hexanedione

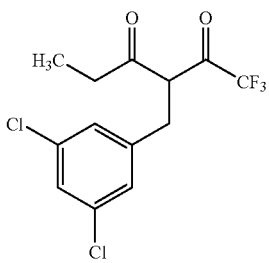

The title compound was prepared by a similar method to that of Preparation 6 using 3-(3,5-dichlorobenzylidene)-1,1,1-trifluoro-2,4-hexanedione of Preparation 16 and was obtained as an oily white solid (180 mg).

LRMS (thermospray): m/z [MH$^+$] 325.

Preparations 18 and 19

(3Z)-3-(3,5-Dichlorobenzylidene)-2,4-hexanedione and (3E)-3-(3,5-Dichlorobenzylidene)-2,4-hexanedione

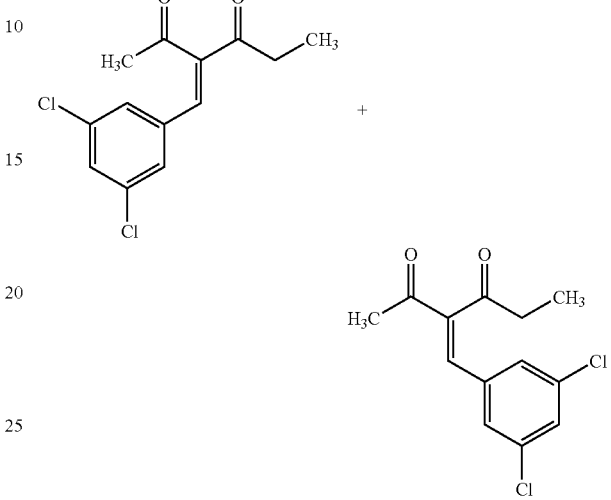

The title compounds were prepared by a similar method to that of Preparation 9 using 2,4-hexanedione and 3,5-dichlorobenzaldehyde. The crude products were purified by flash chromatography on silica gel eluting with a solvent gradient of pentane:ether (20:1, by volume) gradually changing to pentane:ether (10:1, by volume) to afford the title compounds as white solids.

Less Polar Isomer:
$^1$H-NMR (300 MHz, CDCl$_3$): δ=1.10 (t, 3H), 2.40 (s, 3H), 2.52 (q, 2H), 7.20 (s, 2H), 7.39 (s, 1H), 7.40 (s, 1H).
Microanalysis: Found: C, 57.07; H, 4.40. C$_{13}$H$_{12}$Cl$_2$O$_2$ requires C, 57.59; H, 4.46.

More Polar Isomer:
$^1$H-NMR (300 MHz, CDCl$_3$): δ=1.16 (t, 3H), 2.29 (s, 3H), 2.77 (q, 2H), 7.29 (s, 2H), 7.39 (s, 1H), 7.40 (s, 1H).
Microanalysis: Found: C, 57.21; H, 4.22. C$_{13}$H$_{12}$Cl$_2$O$_2$ requires C, 57.59; H, 4.46.

Preparation 20

3-(3,5-Dichlorobenzyl)-2,4-hexanedione

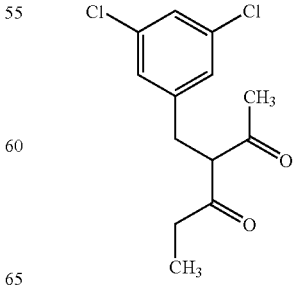

The title compound was prepared by a similar method to that of Preparation 6 using (3Z)-3-(3,5-dichlorobenzylidene)-2,4-hexanedione and (3E)-3-(3,5-dichlorobenzylidene)-2,4-hexanedione of Preparations 18 and 19 and was obtained as yellow oil (300 mg).

$^1$H-NMR (300 MHz, CDCl$_3$): (5:4 keto tautomer:enol tautomer) δ=1.00 (t, 3H, keto), 1.13 (t, 3H, enol), 2.06 (s, 3H, enol), 2.16 (s, 3H, keto), 2.35 and 2.52 (2×m, 2×2H, keto and enol), 3.13 (d, 2H, keto), 3.65 (s, 2H, enol), 3.96 (t, 1H, keto), 7.00 (m, 2×2H, keto and enol), 7.20 (s, 2×1H, keto and enol), 16.87 (s, 1H, enol).

LRMS (thermospray): m/z [MNa$^+$] 295.

Preparation 21

Ethyl(3E and 3Z)-3-acetyl-4-(3,5-dichlorophenyl)-2-oxo-3-butenoate

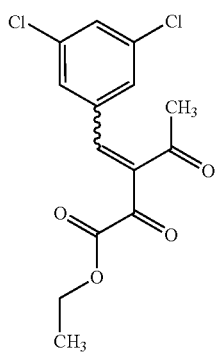

The title compounds were prepared by a similar method to that of Preparation 9 using ethyldioxovalerate and 3,5-dichlorobenzaldehyde and a mixture was obtained (2:3 ratio of isomers, stereochemistry unknown) as an orange oil.

$^1$H-NMR (300 MHz, CDCl$_3$): δ=1.25 (m, 3H), 1.29 (m, 3H), 2.37 (s, 3H), 2.44 (s, 3H), 4.21 (q, 2H), 4.30 (q, 2H), 7.21 (s, 2H), 7.22 (s, 2H), 7.40 (s, 1H), 7.41 (s, 1H), 7.68 (s, 2×1H).

LRMS (thermospray): m/z [MNH$_4^+$] 332.

Preparation 22

Ethyl 3-(3,5-dichlorobenzyl)-2,4-dioxopentanoate

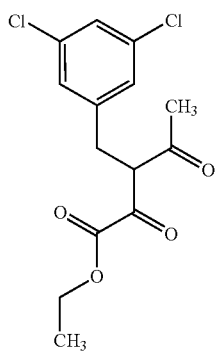

The title compound was prepared by a similar method to that of Preparation 6 using ethyl(3E and 3Z)-3-acetyl-4-(3,5-dichlorophenyl)-2-oxo-3-butenoate of Preparation 21 and was obtained as a yellow oil (8.2 g).

$^1$H-NMR (300 MHz, CDCl$_3$): δ=1.19 (m, 3H), 1.31 (m, 3H), 2.12 (s, 3H), 2.20 (s, 3H), 2.98 (dq, 1H, diketone), 3.74 (s, 2H, enol), 4.23 (m, 4H), 7.03 (s, 4H), 7.20 (s, 2H), 15.91 (s, 1H).

LRMS (thermospray): m/z [MH$^+$] 317.

Preparation 23

4-(3,5-Dichlorobenzyl)-1-(2-hydroxyethyl)-5-methyl-1H-pyrazole-3-carboxylic acid

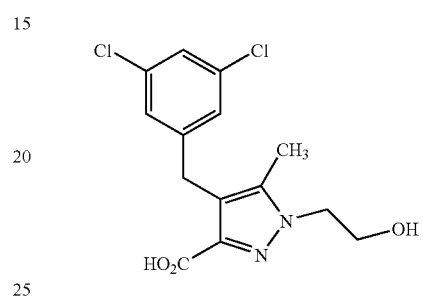

A solution of the ester of Example 84 (1.0 g, 2.8 mmol) in 1,4-dioxan (14 ml) was treated with 1M aqueous sodium hydroxide solution (7 ml) and the reaction mixture was stirred at room temperature for 4 hours. The solution was concentrated under reduced pressure. The residue was dissolved in water (25 ml) and 2M aqueous hydrochloric acid was added. A precipitate formed and was filtered off to afford the title compound as a white solid (613 mg), m.p. 241.2–242.4° C. Further product was obtained from the filtrate by adding methanol and concentrating the solvents under reduced pressure. The residue was dissolved in water and aqueous hydrochloric acid added. A precipitate formed and was filtered off to afford a white solid (108 mg).

$^1$H-NMR (300 MHz, d$_6$-DMSO): δ=2.20 (s, 3H), 3.69 (s, 2H), 4.01 (m, 2H), 4.13 (m, 2H), 7.19 (s, 2H), 7.38 (s, 1H).

LRMS (electrospray): m/z [MH$^+$] 327.

Preparation 24

4-(3,5-Dimethylbenzyl)-3,5-heptanedione

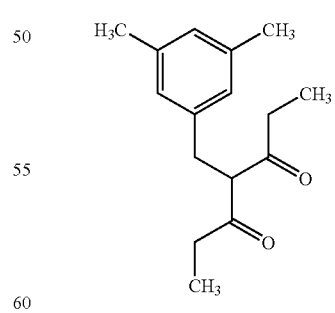

A solution of 3,5-heptanedione (1.24 ml, 9.13 mmol) in 2-butanone (40 ml) was treated with sodium hydride (60% dispersion in oil) (402 mg, 10.05 mmol) (added in portions) and stirred at room temperature for 10 minutes. Sodium iodide (1.5 g, 10.05 mmol) and then by 3,5-dimethylbenzyl bromide (2.0 g, 10.05 mmol) were added to the reaction

Preparation 26

Ethyl [4-(3,5-dichlorobenzyl)-3-methyl-5-oxo-2,5-dihydro-1H-pyrazol-1-yl]acetate

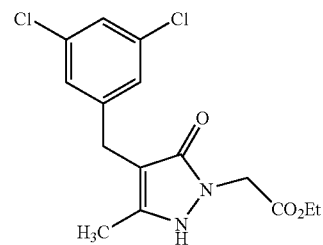

A solution of the β-ketoester of Preparation 25 (100 mg, 0.35 mmol) in ethanol (2 ml) was treated with triethylamine (53 μL, 0.38 mmol) and by ethyl hydrazinoacetate hydrochloride (54 mg, 0.35 mmol) and the resulting mixture was heated at 80° C. in a sealed Reacti-vial (Trade Mark) for 18 hours. After cooling, the mixture was concentrated under reduced pressure. The residue was partitioned between aqueous saturated sodium hydrogen carbonate solution and dichloromethane. The organic phase was dried over anhydrous magnesium sulphate, filtered and evaporated under reduced pressure. The resulting solid was purified by flash chromatography on silica gel eluting with methanol:dichloromethane (1:99, by volume) to afford the title compound (40 mg) as a white solid, m.p. 183.1–184.4° C.

$^1$H-NMR (300 MHz, CDCl$_3$): δ=1.20 (t, 3H), 1.97 (s, 3H), 3.45 (brs, 1H), 3.52 (s, 2H), 4.16 (q, 2H), 4.48 (s, 2H), 7.06 (s, 2H), 7.13 (s, 1H).

LRMS (thermospray): m/z [MH$^+$] 343.

Microanalysis: Found: C, 52.39; H, 4.68; N, 8.08. C$_{15}$H$_{16}$Cl$_2$N$_2$O$_3$ requires C, 52.49; H, 4.70; N, 8.16%.

The mixture which was stirred at room temperature for 18 hours. The solution was concentrated under reduced pressure. The residue was dissolved in ethyl acetate and washed with water (×3). The organic phase was dried over anhydrous magnesium sulphate, filtered and evaporated under reduced pressure. The crude product was purified by flash chromatography on silica gel eluting with cyclohexane followed by cyclohexane:ethyl acetate (40:1, by volume) to afford the title compound as a yellow oil (995 mg).

$^1$H-NMR (300 MHz, CDCl$_3$): (1.7:1 keto tautomer:enol tautomer) δ=1.00 (t, 6H, keto), 1.10 (t, 6H, enol), 2.28 (s, 6H, keto), 2.30 (s, 6H, enol), 2.40 (m, 2×4H, keto and enol), 3.10 (d, 2H, keto), 3.61 (s, 2H, enol), 4.00 (t, 1H, keto), 6.77 (s, 2×2H, keto and enol), 6.87 (s, 2×1H, keto and enol), 16.97 (s, 1H, enol).

LRMS (thermospray): m/z [MH$^+$] 247.

Preparation 25

Ethyl 2-(3,5-dichlorobenzyl)-3-oxobutanoate

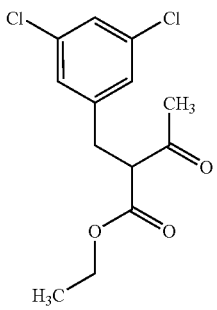

Sodium metal (1.01 g, 44 mmol) was added to ethanol (100 ml) and stirred until all the metal had dissolved. Ethylacetoacetate (15.6 g, 111 mmol) was added and the reaction mixture was stirred under a nitrogen atmosphere for 10 minutes. 3,5-dichlorobenzyl chloride (7.24 g, 40 mmol) was added and the reaction mixture was stirred at room temperature for 3 days. The reaction mixture was filtered and the solution was concentrated under reduced pressure. The orange oil was purified by flash chromatography on silica gel eluting with pentane followed by pentane:ethyl acetate (30:1, by volume) to afford the title compound as a colourless oil (6.4 g).

$^1$H-NMR (300 MHz, CDCl$_3$): (3.3:1 keto tautomer:enol tautomer) δ=1.23 (t, 2×3H, keto and enol), 2.10 (s, 3H, enol), 2.26 (s, 3H, keto), 3.13 (m, 2H, keto), 3.55 (s, 2H, enol), 3.74 (t, 1H, keto), 4.23 (q, 2H, keto and enol), 7.10 (s, 2H, enol), 7.13 (s, 2H, keto), 7.20 (s, 1H, enol), 7.29 (s, 1H, keto), 12.97 (s, 1H, enol).

LRMS (thermospray): m/z [MNH$_4^+$] 306, 308.

Preparation 27

2-(3,5-Dichlorobenzyl)-1-(2-furyl)-1,3-butanedione

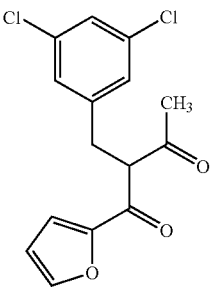

The title compound was prepared by a similar method to that of Preparation 24 using 1-(2-furyl)-1,3-butanedione except that the reaction mixture was heated at 85° C. The crude product was purified by flash chromatography on silica gel eluting with pentane:ethyl actetate (10:1, by volume) to afford the title compound (1.8 g) as a yellow oil.

$^1$H-NMR (400 MHz, CDCl$_3$): δ=2.13 (s, 3H), 3.17 (d, 2H), 4.54 (t, 1H), 6.57 (m, 1H), 7.05 (s, 2H), 7.12 (s, 1H), 7.22 (m, 1H), 7.60 (m, 1H).

LRMS (thermospray): m/z [MH+] 312.

Microanalysis: Found: C, 57.85H, 4.23. $C_{15}H_{12}Cl_2O_3$ requires C, 57.90; H, 3.89.

Preparation 28

3,5-Diethyl-1H-pyrazole

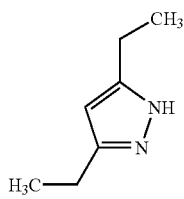

A solution of 3,5-heptanedione (10.0 g, 0.078 mmol) in ethanol (40 ml) was treated dropwise with hydrazine hydrate (4.2 ml, 0.086 mmol) at room temperature producing an exotherm that was cooled by use of an ice bath. After the addition was complete the reaction mixture was allowed to warm to room temperature. The solution was concentrated under reduced pressure. The oil was partitioned between dichloromethane and brine. The aqueous layer was extracted with dichloromethane (×2). The combined organic phases were dried over anhydrous magnesium sulphate, filtered and evaporated under reduced pressure to afford the title compound (9.66 g) as a pale yellow oil that partly solidified on standing.

$^1$H-NMR (400 MHz, CDCl$_3$): δ=1.22 (t, 6H), 2.60 (q, 4H), 5.85 (s, 1H).

LRMS (thermospray): m/z [MH+] 124.

Microanalysis: Found: C, 67.00H, 9.85; N, 22.37. $C_7H_{12}N_2$ requires C, 66.73; H, 9.76; N, 22.23%.

Preparation 29

3,5-Diethyl-4-iodo-1H-pyrazole

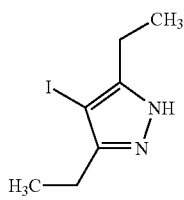

A solution of the pyrazole of Preparation 28 (2.0 g, 16.1 mmol) in dichloromethane (80 ml) was cooled to 0° C. and treated with N-iodosuccinimide (3.97 g, 17.7 mmol) and the resulting mixture was stirred for 18 hours. Further N-iodosuccinimide (360 mg, 1.77 mmol) was added and the solution was stirred for a further hour. The reaction mixture was washed with saturated aqueous sodium hydrogencarbonate solution. The organic layer was dried over anhydrous magnesium sulphate, filtered and evaporated under reduced pressure. The crude product was purified by flash chromatography on silica gel eluting with a solvent gradient of pentane:ethyl actetate (4:1, by volume) gradually changing to pentane:ethyl actetate (2:1, by volume). Methanol was added to the resulting solid, which was collected by filtration and the filtrate was concentrated under reduced pressure. The resulting oil was dissolved in dichloromethane and washed with 10% aqueous sodium metabisulphite solution. The organic layer was dried over anhydrous magnesium sulphate, filtered and evaporated under reduced pressure to afford the title compound (3.3 g) as a white solid.

$^1$H-NMR (400 MHz, CDCl$_3$): δ=1.26 (t, 6H), 2.68 (q, 4H).

LRMS (thermospray): m/z [MH+] 251.

Microanalysis: Found: C, 33.41H, 4.38; N, 11.14. $C_7H_{11}N_2$I requires C, 33.62; H, 4.43; N, 11.20%.

Preparation 30

1-(2-{[tert-Butyl(dimethyl)silyl]oxy}ethyl)-3,5-diethyl-4-iodo-1H-pyrazole

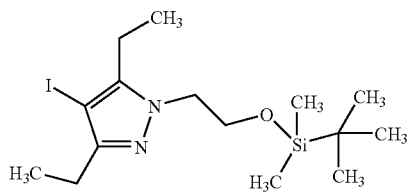

A solution of the pyrazole of Preparation 29 (3.3 g, 13.2 mmol) in dimethylformamide (70 ml) was cooled to 0° C. and treated with sodium hydride (60% dispersion in oil) (580 mg, 14.5 mmol). After 20 minutes sodium iodide (2.17 g, 14.5 mmol) and (2-bromoethoxy)-tert-butyldimethylsilane (3.11 ml, 14.5 mmol) were added and the resulting mixture was stirred at 0° C. for 30 minutes. The reaction mixture was allowed to warm to room temperature and was stirred for 18 hours at this temperature. Further (2-bromoethoxy)-tert-butyldimethylsilane (2×2.8 ml) was added over a 2 hour period. The reaction mixture was then heated at 50° C. for 1 hour. After cooling to 0° C., the reaction mixture was diluted with water (2 ml) and evaporated under reduced pressure. The resulting solid was partitioned between dichloromethane and water. The organic layer was dried over anhydrous magnesium sulphate, filtered and evaporated under reduced pressure. The resulting oil was then dissolved in ethyl acetate and washed with brine (×4). The organic phase was dried over anhydrous magnesium sulphate, filtered and evaporated under reduced pressure. The crude product was purified by flash chromatography on silica gel eluting with a solvent gradient of cyclohexane gradually changing to cyclohexane:ethyl acetate (10:1, by volume) to afford the title compound (2.6 g) as a colourless oil.

$^1$H-NMR (400 MHz, CDCl$_3$): δ=−0.10 (s, 6H), 0.80 (s, 9H), 1.16 (t, 3H), 1.23 (t, 3H), 2.60 (q, 2H), 2.74 (q, 2H), 3.97 (t, 2H), 4.16 (t, 2H).

LRMS (thermospray): m/z [MH+] 409.

Preparation 31

[1-(2-{[tert-Butyl(dimethyl)sily]oxy}ethyl)-3,5-diethyl-1H-pyrazol-4-yl](3,5-dichlorophenyl)methanol

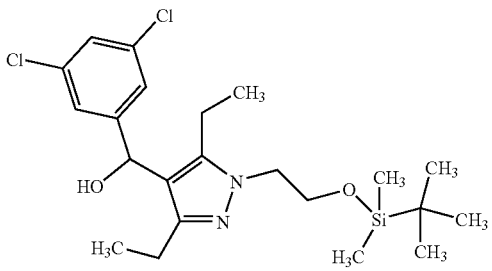

A solution of the iodo-pyrazole (500 mg, 1.22 mmol) of Preparation 30 in tetrahydrofuran (7.5 ml) at 0° C. was treated with iso-propylmagnesium chloride (2M in diethyl-ether) (725 μL, 1.46 mmol). After 1 hour, 3,5-dichlorobenzaldehyde (252 mg, 1.46 mmol) was added and after a further 10 minutes the reaction mixture was allowed to warm to room temperature. After 3 days saturated aqueous ammonium chloride solution was added to the reaction mixture which was then extracted with dichloromethane. The organic extract was dried over anhydrous magnesium sulphate, filtered and evaporated under reduced pressure. The crude product was purified by flash chromatography on silica gel eluting with a solvent gradient of pentane:ethyl acetate (5:1, by volume) gradually changing to pentane:ethyl acetate (2:1, by volume) to afford the title compound (190 mg) as a white solid.

$^1$H-NMR (400 MHz, CDCl$_3$): δ=−0.10 (s, 6H), 0.80 (s, 9H), 1.03 (t, 3H), 1.16 (t, 3H), 2.58 (m, 4H), 4.00 (t, 2H), 4.10 (t, 2H), 5.80 (s, 1H), 7.39 (m, 3H).

LRMS (thermospray): m/z [MH$^+$] 457.

Preparation 32

[1-(2-{[tert-Butyl(dimethyl)silyl]oxy}ethyl)-3,5-diethyl-1H-pyrazol-4-yl](3,5-dichlorophenyl)methanone

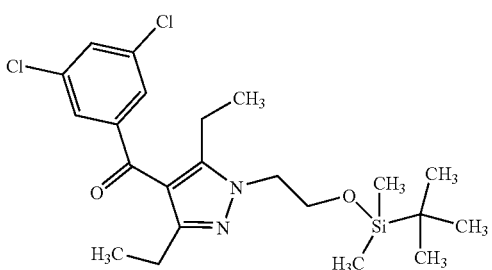

A solution of the alcohol of Preparation 31 (75 mg, 0.16 mmol) in dichloromethane (2 ml) was treated with N-methylmorpholine N-oxide (28 mg, 0.24 mmol) and tetra-n-propylammonium perruthenate (VII) (3 mg, 0.008 mmol) and stirred at room temperature, under a nitrogen atmosphere for 2 hours. The reaction was diluted with dichloromethane and washed with aqueous sodium sulphite solution (×3). The organic layer was dried over anhydrous magnesium sulphate, filtered and evaporated under reduced pressure. The crude material was pre-absorbed onto silica and purified by flash chromatography on silica gel eluting with a solvent gradient of pentane gradually changing to pentane:ethyl acetate (10:1, by volume) to afford the title compound (73 mg) as a colourless oil.

$^1$H-NMR (400 MHz, CDCl$_3$): δ=−0.03 (s, 6H), 0.84 (s, 9H), 1.13 (m, 6H), 2.48 (m, 2H), 2.77 (m, 2H), 4.06 (m, 2H), 4.19 (m, 2H), 7.29 (s, 1H), 7.58 (s, 2H).

LRMS (thermospray): m/z [MH$^+$] 455.

Preparation 33

1-(2-{[Tert-butyl(dimethyl)silyl]oxy}ethyl)-4-[(3,5-dichlorophenyl)(methoxy)methyl]-3,5-diethyl-1H-pyrazole

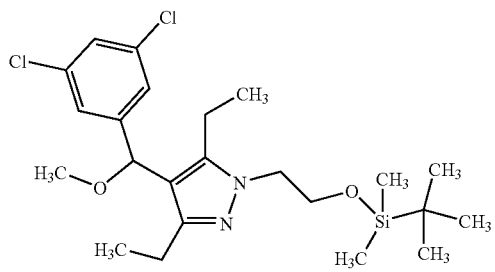

A solution of the alcohol of Preparation 31 (75 mg, 0.16 mmol) in dimethylformamide (1 ml) was treated with sodium hydride (60% dispersion in oil) (7 mg, 0.18 mmol) and stirred under a nitrogen atmosphere, at room temperature for 30 minutes. Methyl iodide (11 μL, 0.18 mmol) was added and the resulting mixture was stirred for 7 days. The solution was concentrated under reduced pressure. The residue was partitioned between dichloromethane and saturated aqueous sodium hydrogencarbonate solution. The organic phase was dried over anhydrous magnesium sulphate, filtered and evaporated under reduced pressure. The crude material was purified by flash chromatography on silica gel eluting with cyclohexane:ethyl acetate (10:1, by volume) to afford the title compound (30 mg) as a colourless oil.

$^1$H-NMR (400 MHz, CDCl$_3$): δ=−0.10 (m, 6H), 0.81 (s, 9H), 1.03 (t, 3H), 1.16 (t, 3H), 2.58 (m, 4H), 3.39 (s, 3H), 4.03 (m, 2H), 4.13 (m, 2H), 5.20 (s, 1H), 7.29 (s, 3H).

LRMS (thermospray): m/z [MH$^+$] 471.

Preparation 34

4-(2,6-Difluorobenzylidene)-3,5-heptanedione

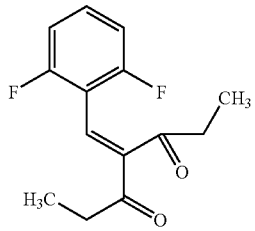

A mixture of 3,5-heptanedione (1.36 ml, 10 mmol), 2,6-difluorobenzaldehyde (1.08 ml, 10 mmol), piperidine (20 µL, 0.2 mmol), glacial acetic acid (149 µL, 2.6 mmol), molecular sieves and toluene (7 ml) was heated at 70° C., under a nitrogen atmosphere for 3 hours. Further 2,6-difluorobenzaldehyde (540 µL, 5 mmol) was added and the resulting mixture was stirred at 70° C. for a further 7 hours. After cooling, the molecular sieves were filtered off. The filtrate was concentrated under reduced pressure. The residue was partitioned between dichloromethane and water. The organic phase was dried over anhydrous magnesium sulphate, filtered and concentrated under reduced pressure. The crude material was purified by flash chromatography on silica gel eluting with pentane:dichloromethane (4:1, by volume) and then with a solvent gradient of pentane:diethylether (20:1, by volume) gradually changing to pentane:diethylether (10:1, by volume) to afford the title compound (775 mg) as a colourless oil.

$^1$H-NMR (400 MHz, CDCl$_3$): δ=1.11 (t, 3H), 1.20 (t, 3H), 2.63 (q, 2H), 2.80 (q, 2H), 6.95 (m, 2H), 7.40, (s, 1H), 7.65 (m, 1H).

LRMS (electrospray): m/z [MH$^+$] 253.

Preparation 35

4-(2,6-Difluorobenzyl)-3,5-heptanedione

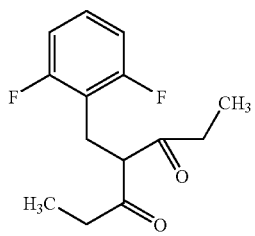

The title compound was prepared by the same method as Preparation 2 using the alkene of Preparation 34 and was obtained as a white solid, m.p. 55–56° C.

$^1$H-NMR (400 MHz, CDCl$_3$): δ=1.00 (t, 6H), 2.46 (m, 4H), 3.20 (d, 2H), 4.03 (t, 1H), 6.84 (m, 2H), 7.18 (m, 1H).

LRMS (thermospray): m/z [MNH$_4^+$] 272.

Microanalysis: Found: C, 66.22H, 6.34. C$_{14}$H$_{16}$F$_2$O$_2$ requires C, 66.13; H, 6.34.

Preparation 36

Ethyl 3-[(3,5-dichlorophenyl)sulfanyl]-2,4-dioxohexanoate

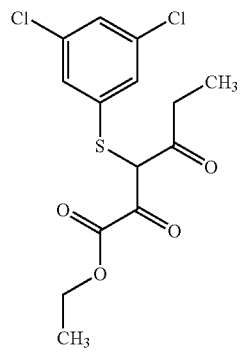

A solution of ethyl 3-chloro-2,4-dioxohexanoate (EP117082 A2) (7.10 g, 34.4 mmol) in acetone (175 ml) was treated with 3,5-dichlorothiophenol (6.16 g, 34.4 mmol), potassium carbonate (5.22 g, 37.8 mmol) and sodium iodide (5.16 g, 34.4 mmol) and the resulting mixture was stirred at room temperature for 18 hours. The reaction mixture was diluted with water (70 ml) and concentrated under reduced pressure. The residue was diluted with 2M aqueous hydrochloric acid (70 ml) and extracted with dichloromethane (3×150 ml). The combined organic extracts were dried over anhydrous magnesium sulphate, filtered and concentrated under reduced pressure. The crude product was purified by flash chromatography on silica gel eluting with a solvent gradient of cyclohexane:ethyl acetate (3:1, by volume) gradually changing to cyclohexane:ethyl acetate (1:1, by volume) to afford the title compound (12.3 g) as a red oil.

$^1$H-NMR (400 MHz, CDCl$_3$): δ=1.14 (t, 3H), 1.19 (t, 3H), 2.70 (q, 2H), 4.28 (q, 2H), 7.02 (s, 2H), 7.14 (s, 1H), 16.15 (brs, 1H).

LRMS (electrospray): m/z [M−H$^+$] 347.

Preparation 37

Ethyl 1-(2-{[tert-butyl(dimethyl)silyl]oxy}ethyl)-4-[(3,5-dichlorophenyl)sulfanyl]-5-ethyl-1H-pyrazole-3-carboxylate

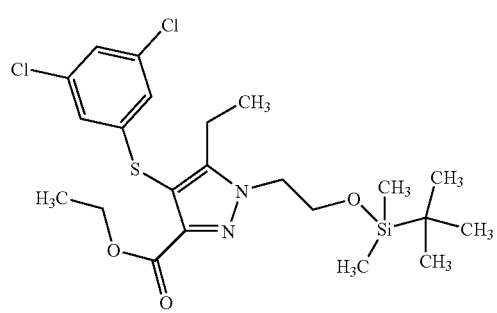

To a solution of Example 46 (1.03 g, 2.65 mmol) in dimethylformamide (5 ml) was added imidazole (361 mg, 5.30 mmol), followed by tert-butyldimethylchlorosilane (600 mg, 3.97 mmol). The solution was stirred at room temperature for 4 days. The reaction mixture was partitioned between ethyl acetate and water and the aqueous phase was further extracted with ethyl acetate. The combined organic phases were dried over anhydrous magnesium sulphate, filtered and evaporated under reduced pressure to give a yellow oil. The crude product was purified by flash chromatography on silica gel eluting with cyclohexane:ethyl acetate (20:1, by volume), followed by cyclohexane:ethyl actetate (5:1, by volume) to afford the title compound (1.1 g) as a white powder, m.p. 83–84° C.

$^1$H-NMR (400 MHz, CDCl$_3$): δ=−0.08 (s, 6H), 0.80 (s, 9H), 1.12 (t, 3H), 1.22 (t, 3H), 2.84 (q, 2H), 4.04 (t, 2H), 4.32 (m, 4H), 6.91 (s, 2H), 7.04 (s, 1H).

LRMS (thermospray): m/z [MH$^+$] 503.

Microanalysis: Found: C, 52.35; H, 6.43; N, 5.46. C$_{22}$H$_{32}$Cl$_2$N$_2$O$_3$SSi requires C, 52.47; H, 6.41; N, 5.56%.

Preparation 38

{1-(2-{[tert-Butyl(dimethyl)silyl]oxy}ethyl)-4-[(3,5-dichlorophenyl)sulfanyl]-5-ethyl-1H-pyrazol-3-yl}methanol

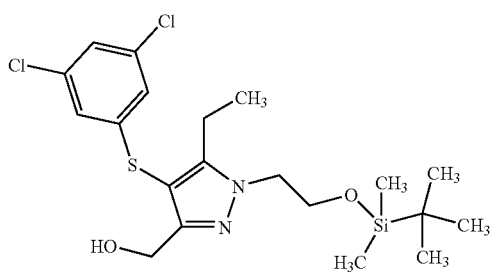

A stirred solution of the pyrazole (1.119, 2.21 mmol) of Preparation 37 in THF (20 ml) was cooled to −78° C. and treated dropwise with a solution of lithium aluminium hydride in THF (2.65 ml of a 1.0M solution). After 1 hour the mixture was warmed to 0° C. and after a further 2 hours water (2 ml) was carefully added. The reaction mixture was partitioned between ethyl acetate and water and then the aqueous phase was further extracted with ethyl acetate. The combined organic phases were dried over anhydrous magnesium sulphate, filtered and evaporated under reduced pressure to give a colourless oil. The crude product was purified by flash chromatography on silica gel eluting with cyclohexane:ethyl acetate (10:1, by volume) followed by cyclohexane:ethyl actetate (5:1, by volume) to afford the title compound (891 mg) as a colourless oil.

$^1$H-NMR (400 MHz, CDCl$_3$): δ=−0.08 (s, 6H), 0.80 (s, 9H), 1.04 (t, 3H), 2.00 (t, 1H), 2.75 (q, 2H), 4.00 (t, 2H), 4.18 (t, 2H), 4.60 (d, 2H), 6.84 (s, 2H), 7.02 (s, 1H).

LRMS (thermospray): m/z [MH$^+$] 461.

Preparation 39

{1-(2-{[tert-Butyl(dimethyl)silyl]oxy}ethyl)-4-[(3,5-dichlorophenyl)sulfanyl]-5-ethyl-1H-pyrazol-3-yl}acetonitrile

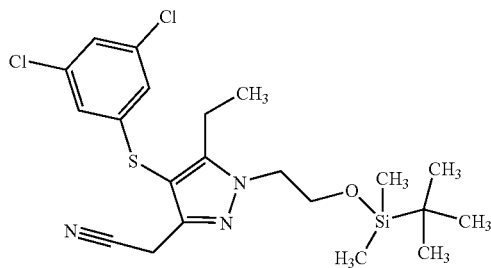

To a stirred solution of the alcohol (340 mg, 0.74 mmol) of Preparation 38 in dichloromethane (6 ml) was added triethylamine (113 μl, 0.81 mmol) and methanesulfonyl chloride (63 μl, 0.81 mmol). After 1 hour at room temperature the reaction mixture was partitioned between dichloromethane and water and then the aqueous phase was further extracted with dichloromethane. The combined organic phases were dried over anhydrous magnesium sulphate, filtered and evaporated under reduced pressure to give a colourless oil. This crude mesylate was dissolved in dimethylformamide (5 ml) and sodium cyanide (109 mg, 2.22 mmol) was added. The reaction mixture was heated at 60° C. for 1 hour. After cooling to room temperature, the mixture was concentrated under reduced pressure and the residue was partitioned between dichloromethane and water. The organic phase was separated, washed with water and brine, dried over anhydrous magnesium sulphate, filtered and evaporated under reduced pressure to give a yellow oil. The crude product was purified by flash chromatography on silica gel eluting with cyclohexane:ethyl acetate (3:1, by volume) to afford the title compound (240 mg) as a colourless oil.

$^1$H-NMR (400 MHz, CDCl$_3$): δ=−0.04 (s, 6H), 0.82 (s, 9H), 1.11 (t, 3H), 2.78 (q, 2H), 3.62 (s, 2H), 4.02 (t, 2H), 4.20 (t, 2H), 6.82 (s, 2H), 7.10 (s, 1H).

LRMS (electrospray): m/z [M+Na$^+$] 492.

Accurate Mass: Found: 470.1250 [MH$^+$]; C$_{21}$H$_{30}$Cl$_2$N$_3$OSSi requires 470.1250 [MH$^+$].

Preparation 40

4-Chloro-3,5-heptanedione

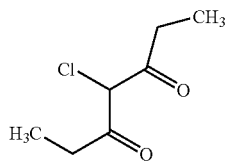

Chlorotrimethylsilane (29.7 ml, 0.234 mol) was added dropwise to a stirred pale yellow solution of tetrabutylammonium bromide (1.26 g, 3.9 mmol) in dry acetonitrile (116 ml) at room temperature under nitrogen. The resulting solution was cooled in ice and 3,5-heptanedione (10.6 ml, 78.0 mmol) and then dry dimethylsulphoxide (16.6 ml, 0.234 mol) were added dropwise over 5 minutes producing a yellow solution which was allowed to warm slowly to room temperature, with stirring, over 4 hours. The mixture was diluted with water (1 liter), stirred for 10 min and then extracted with ether (1×500 ml, 2×250 ml). The combined ether layers were dried over magnesium sulphate, filtered and concentrated under reduced pressure to leave a yellow oil. The crude product was purified by distillation under reduced pressure to afford the title compound (5.5 g) as a pale yellow oil, b.p. 102–105° C./54 mmHg containing ca. 10% 4,4-dichloro-3,5-heptanedione as estimated by microanalysis.

$^1$H-NMR (400 MHz, CDCl$_3$): δ=1.12 (t, 6H), 2.59 (q, 4H), 4.77 (s, 0.2H, diketone), 15.50 (s, 0.8H, enol).

LRMS (thermospray): m/z [MNH$_4^+$] 180 for title compound and 214 for dichlorinated impurity.

Preparation 41

4-[(3,5-Dichlorophenyl)sulfanyl]-3,5-heptanedione

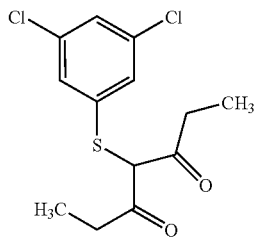

To a stirred solution of the chlorodiketone (1.0 g) of Preparation 40 in acetone (30 ml) was added 3,5-dichlorothiophenol (1.1 g, 6.15 mmol), potassium carbonate (900 mg, 6.77 mmol) and sodium iodide (900 mg, 6.15 mmol). After 18 hours the reaction mixture was diluted with water (20 ml) and the acetone was removed under reduced pressure. The residue was partitioned between 2M HCl and dichloromethane. The aqueous phase was separated and further extracted with dichloromethane. The combined organic phases were washed with brine, dried over magnesium sulphate, filtered and concentrated under reduced pressure to leave a yellow oil (2 g). The crude product was used without further purification.

$^1$H-NMR (400 MHz, CDCl$_3$): enol tautomer, δ=1.03 (t, 6H), 2.62 (m, 4H), 6.91 (s, 2H), 7.08 (s, 1H).

LRMS (electrospray): m/z [M–H$^+$] 303.

Preparation 42

3-Oxopentanenitrile

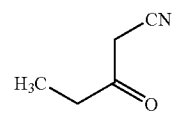

A mixture of ethyl propionate (20 g, 196 mmol) and sodium ethoxide (13.3 g, 196 mmol) was heated at 80° C. After 15 mins acetonitrile (13.3 ml, 255 mmol) was added and the mixture was heated at 120° C. After 13 hours the reaction mixture was cooled and acidified to pH2 using 1M HCl. The volatile reaction components were removed under reduced pressure and the mixture was extracted using dichloromethane. The organic phase was separated, washed with water, washed with brine and concentrated under reduced pressure to give a brown oil (10 g). The crude product was used without further purification.

H-NMR (400 MHz, CDCl$_3$): δ=1.01 (t, 3H), 2.56 (q, 2H), 3.43 (s, 2H).

Preparation 43

2-(3,5-Dichlorobenzyl)-3-oxopentanenitrile

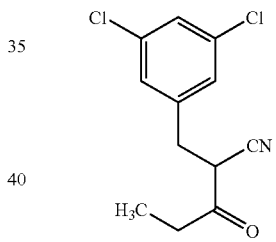

A stirred solution of the nitrile (11.3 g, 117 mmol) of Preparation 42 and 3,5-dichlorobenzylchloride (27.8 g, 117 mmol) in N,N-dimethylformamide (200 ml) was cooled to 0° C. before addition of sodium hydride (60% W/w suspension in mineral oil) (9.3 g, 234 mmol) portionwise. After 2 hours the reaction mixture was quenched by the addition of saturated aqueous ammonium chloride solution (500 ml) and the resulting mixture was extracted with ethyl acetate. The organic phase was separated and twice washed with water, washed with brine, dried over magnesium sulphate, filtered and concentrated under reduced pressure to give a dark oil. The crude product was purified by flash chromatography on silica gel eluting with cyclohexane:ethyl acetate (9:1, by volume) to afford the title compound (7 g) as a white solid, m.p. 59–60° C.

$^1$H-NMR (400 MHz, CDCl$_3$): δ=1.04 (t, 3H), 2.68 (m, 2H), 3.02 (m, 1H), 3.18 (m, 1H), 3.58 (m, 1H), 7.10 (s, 2H), 7.25 (s, 1H).

LRMS (thermospray): m/z [M+NH$_4^+$] 273.

Microanalysis: Found: C, 56.06; H, 4.33; N, 5.41. C$_{12}$H$_{11}$Cl$_2$NO requires C, 56.27; H, 4.33; N, 5.47%.

Preparation 44

1-(2-{[tert-Butyl(dimethyl)silyl]oxy}ethyl)-4-(3,5-dichlorobenzyl)-3-ethyl-1H-pyrazol-5-amine

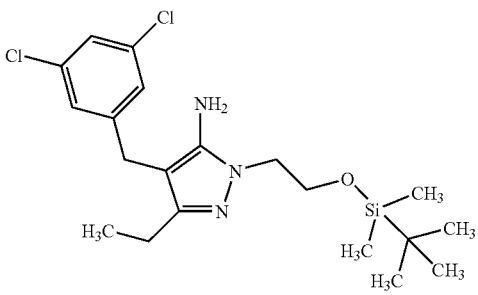

To a solution of the pyrazole of Example 89 (3.0 g, 9.6 mmol) in dimethylformamide (20 ml) was added imidazole (850 mg, 12.5 mmol), followed by tert-butyldimethylchlorosilane (1.58 g, 10.6 mmol). The solution was stirred at room temperature for 20 hours. The reaction mixture was partitioned between diethyl ether and aqueous sodium carbonate and the aqueous phase was separated and further extracted with diethyl ether. The combined organic phases were washed with water, washed with brine, dried over anhydrous magnesium sulphate, filtered and evaporated under reduced pressure. The crude product was purified by flash chromatography on silica gel eluting with dichloromethane:methanol:ammonia (95:5:0.5, by volume) to afford the title compound (4.0 g) as a colourless oil.

$^1$H-NMR (400 MHz, CDCl$_3$): δ=−0.08 (s, 6H), 0.79 (s, 9H), 1.11 (t, 3H), 2.42 (q, 2H), 3.58 (s, 2H), 3.63 (s, 2H), 3.87 (t, 2H), 4.07 (t, 2H), 7.00 (s, 2H), 7.14 (s, 1H).

LRMS (thermospray): m/z [MH$^+$] 428.

Microanalysis: Found: C, 55.92; H, 7.28; N, 9.74. C$_{20}$H$_{31}$Cl$_2$N$_3$OSi requires C, 56.06; H, 7.29; N, 9.81%.

Preparation 45

5-(3-Oxo-2-propionylpentyl)isophthalonitrile

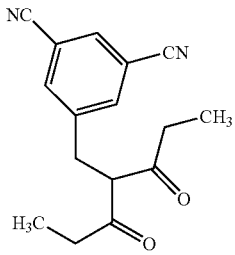

Sodium hydride (60% dispersion in oil, 116 mg, 2.90 mmol) was added to a stirred solution of 3,5-heptanedione (358 μl, 2.64 mmol) in 2-butanone (5 ml) at room temperature under nitrogen. After evolution of hydrogen had ceased, sodium iodide (396 mg, 2.64 mmol) and then a solution of 5-bromomethyl-isophthalonitrile (J. Org. Chem., 1990, 55 (3), 1040–1043) (584 mg, 2.64 mmol) in 2-butanone (6 ml) was added and the mixture was heated at reflux for 6 hours. After cooling, the mixture was quenched with water (1 ml) and the 2-butanone was removed under reduced pressure. The residue was partitioned between water (40 ml) and dichloromethane (40 ml) and the organic layer was separated, dried over magnesium sulphate, filtered and concentrated under reduced pressure. The crude product was purified by flash chromatography on silica gel eluting with a solvent gradient starting with pentane:ethyl acetate (10:1, by volume) and finishing with pentane:ethyl acetate (3:1, by volume) to give the title compound (370 mg) as a white solid m.p. 67–69° C.

$^1$H-NMR (300 MHz, CDCl$_3$): δ=1.1 (6H, m), 2.44 (4H, m), 3.20 (2H, d, keto), 3.79 (2H, s, enol), 3.98 (1H, t, keto), 7.61 (2H, s), 7.8 (1H, s), 17.11 (1H, s, enol).

LRMS (electrospray): m/z [M−H$^+$] 267.

Microanalysis: Found: C, 71.35; H, 6.02; N, 10.41. C$_{16}$H$_{16}$N$_2$O$_2$ requires C, 71.62; H, 6.01; N, 10.44%.

Preparation 46

O-(3,5-Dibromophenyl) diethylthiocarbamate

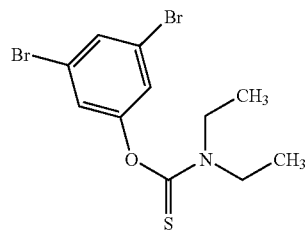

A solution of 3,5-dibromophenol (prepared according to Recl. Trav. Chim. Pays-Bas. 1908, 27, 30) (10.08 g, 40 mmol) and diethylthiocarbamyl chloride (7.9 g, 52 mmol) in 1-methyl-2-pyrrolidinone (80 ml) was cooled to 0° C. under an atmosphere of nitrogen. Sodium hydride (60% dispersion in mineral oil, 1.92 g, 48 mmol) was added portionwise with stirring. The mixture was allowed to warm to 20° C. and stirred under nitrogen for two hours. The mixture was partitioned between diethyl ether (250 ml) and water (350 ml) and the aqueous layer was further extracted with diethyl ether (250 ml then 100 ml). The organic layers were combined, washed with water (150 ml) and brine (150 ml), dried over magnesium sulphate, filtered and concentrated under reduced pressure to leave a yellow solid. The crude product was purified by flash chromatography on silica gel eluting with dichloromethane:pentane (1:1, by volume) to provide the title compound (13.4 g) as a white solid, m.p. 72–74° C.

$^1$H-NMR (400 MHz, CDCl$_3$): δ=1.27 (m, 6H), 3.62 (q, 2H), 3.84 (q, 2H), 7.17 (d, 2H), 7.51 (d, 1H).

Microanalysis: Found: C, 35.99; H, 3.54; N, 3.73. C$_{11}$H$_{13}$Br$_2$NOS requires C, 35.99; H, 3.57; N, 3.82%.

Preparation 47

S-(3,5-dibromophenyl) diethylthiocarbamate

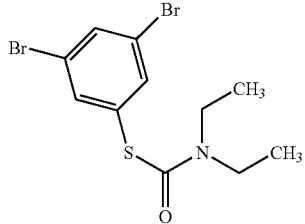

O-(3,5-dibromophenyl) diethylthiocarbamate (13.24 g, 36.1 mmol) (Preparation 46) was heated to 200° C., with stirring, under an atmosphere of nitrogen, for 15 hours to leave a yellow oil. A sample of this material (19) was purified by flash chromatography on silica gel eluting with pentane:dichloromethane (1:1, by volume) to provide the title compound (700 mg) as a colourless oil.

$^1$H-NMR (300 MHz, CDCl$_3$): δ=1.26 (m, 6H), 3.43 (q, 4H), 7.62 (s, 2H), 7.68 (s, 1H).

Microanalysis: Found: C, 35.92; H, 3.47; N, 3.69. C$_{11}$H$_{13}$Br$_2$NOS requires C, 35.99; H, 3.57; N, 3.82%.

Preparation 48

3,5-Dibromobenzenethiol

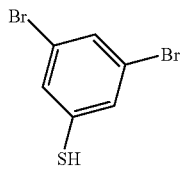

Sodium hydroxide (1.96 g, 49 mmol) was added to a solution of S-(3,5-dibromophenyl) diethylthiocarbamate (12 g, 32.7 mmol) (Preparation 47) in methanol (33 ml) and the mixture was heated at reflux for 15 hours. The mixture was cooled to 20° C. and concentrated under reduced pressure. The residue was partitioned between dichloromethane (90 ml) and water (250 ml) and the aqueous layer was further extracted with dichloromethane (90 ml). The combined organic layers were washed with a solution of sodium hydroxide (1N, 100 ml). The combined aqueous layers were cooled to 0° C. and the pH was adjusted to 2 by the addition of concentrated hydrochloric acid, giving a white suspension. This suspension was extracted with dichloromethane (2×250 ml) and the combined extracts were washed with brine (25 ml), dried over magnesium sulphate, filtered and concentrated under reduced pressure to leave the title compound as a yellow solid (6.7 g).

$^1$H-NMR (300 MHz, CDCl$_3$): δ=3.55 (s, 1H), 7.36 (m, 2H), 7.46 (s, 1H).

LRMS (electrospray): m/z [M−H] 267.

Microanalysis: Found: C, 27.01; H, 1.42. C$_6$H$_4$Br$_2$S requires C, 26.89; H, 1.50%.

Preparation 49

4-[(3,5-Dibromophenyl)sulfanyl]-3,5-heptanedione

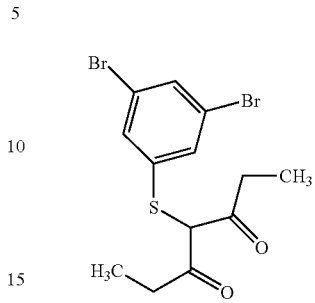

Potassium carbonate (1.9 g, 14 mmol) was added to a solution of 3,5-dibromobenzenethiol (2.84 g, 10.5 mmol) (Preparation 48) and 4-chloroheptane-3,5-dione (1.7 g, 10.5 mmol) (Preparation 40) in acetone (12 ml) producing a white suspension. The mixture was stirred at room temperature for 15 hours. The mixture was concentrated under reduced pressure and the residue was partitioned between dichloromethane (100 ml) and 1N hydrochloric acid (70 ml). The aqueous layer was extracted with further dichloromethane (2×100 ml). The combined organic layers were washed with brine (50 ml), dried over magnesium sulphate, filtered and concentrated under reduced pressure to leave a pink oil. The crude product was purified by flash chromatography on silica gel eluting with pentane:dichloromethane (1:1, by volume) to provide the title compound (3 g) as a pink oil.

$^1$H-NMR (300 MHz, CDCl$_3$): δ=1.13 (m, 6H), 2.7 (m, 4H), 7.12 (s, 2H), 7.42 (s, 1H), 17.70 (s, 1H).

LRMS (thermospray): m/z [MNH$_4^+$] 412.

LRMS (electrospray): m/z [M−H] 393.

Preparation 50

1-(2-{[tert-Butyl(dimethyl)silyl]oxy}ethyl)-4-[(3,5-dibromophenyl)sulfanyl]-3,5-diethyl-1H-pyrazole

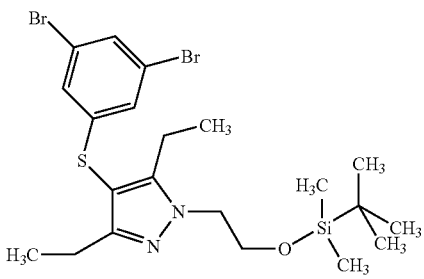

A solution of 2-{4-[(3,5-dibromophenyl)sulfanyl]-3,5-diethyl-1H-pyrazol-1-yl}ethanol (1.3 g, 3 mmol) (Example 93) in dimethylformamide (3 ml) was treated with imidazole (270 mg, 4 mmol) and tert-butyl(chloro)dimethylsilane (500 mg, 3.3 mmol) and stirred at 20° C. for 15 hours. The mixture was partitioned between diethyl ether (70 ml) and citric acid solution (5% weight:volume in water, 150 ml). The aqueous layer was further extracted with diethyl ether (70 ml) and the combined organic layers were washed with brine (2×70 ml), dried over magnesium sulphate, filtered and concentrated under reduced pressure. The crude product was purified by flash chromatography on silica gel eluting with pentane:dichloromethane (1:1, by volume) to provide the title compound (1.2 g) as a colourless oil.

$^1$H-NMR (300 MHz, CDCl$_3$): δ=−0.05 (s, 6H), 0.84 (s, 9H), 1.10 (t, 3H), 1.19 (t, 3H), 2.58 (q, 2H), 2.75 (q, 2H), 4.04 (m, 2H), 4.18 (m, 2H), 7.05 (s, 2H), 7.35 (s, 1H).

LRMS (electrospray): m/z [MH$^+$] 549.

Preparation 51

5-{[1-(2-{[tert-Butyl(dimethyl)silyl]oxy}ethyl)-3,5-diethyl-1H-pyrazol-4-yl]sulfanyl}isophthalonitrile

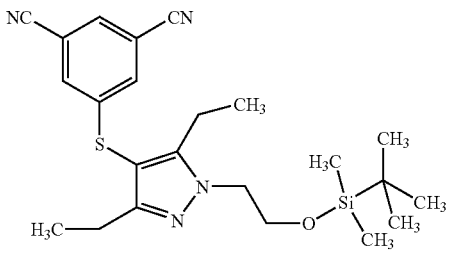

A solution of 1-(2{[tert-butyl(dimethyl)silyl]oxy}ethyl)-4-[(3,5-dibromophenyl)sulfanyl]-3,5-diethyl-1H-pyrazole (500 mg, 0.9 mmol) (Preparation 50) in dimethylformamide (2 ml) was treated with zinc cyanide (130 mg, 1.1 mmol), 1,1′-bis(diphenylphosphino)ferrocene (65 mg, 0.12 mmol) and tris(dibenzylideneacetone)dipalladium (92 mg, 0.1 mmol) and the resulting brown suspension was heated at 100° C. for 2½ days. After cooling the mixture was diluted with water (70 ml) and extracted with ethyl acetate (2×60 ml). The combined organic layers were washed with water (20 ml) and brine (30 ml), dried over magnesium sulphate, filtered and concentrated under reduced pressure to leave a brown oil. The crude product was purified by flash chromatography on silica gel eluting with pentane:dichloromethane (1:1, by volume) then dichloromethane and finally with dichloromethane:ethyl acetate (19:1, by volume) to provide the title compound (180 mg) as a brown oil.

$^1$H-NMR (300 MHz, CDCl$_3$): δ=−0.03 (s, 6H), 0.84 (s, 9H), 1.10 (t, 3H), 1.18 (t, 3H), 2.56 (q, 2H), 2.72 (q, 2H), 4.06 (m, 2H), 4.20 (m, 2H), 7.43 (s, 2H), 7.60 (s, 1H).

LRMS (thermospray): m/z [MH$^+$] 441.

PHARMACOLOGICAL ACTIVITY

All the compounds of the Examples were tested for their ability to inhibit HIV-1 reverse transcriptase by the method described on page 36 and all had an IC$_{50}$ of less than 100 micromolar.

The invention claimed is:

1. A method for the treatment of a human immunodeficiency viral (HIV), or genetically related retroviral, infection or a resulting acquired immunodeficiency syndrome (AIDS) comprising the administration of an effective amount of a compound of the formula Ib

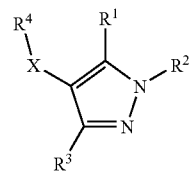

or a pharmaceutically acceptable salt or solvate thereof, wherein either (i) R$^1$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, —OCONR$^5$R$^5$, —NR$^5$CO$_2$R$^7$, —NR$^5$R$^5$, —NR$^5$COR$^5$, —NR$^5$CO—(C$_1$–C$_6$ alkylene)-OR$^5$, —NR$^5$CONR$^5$R$^5$, —NR$^5$SO$_2$R$^7$ or R$^6$, said C$_1$–C$_6$ alkyl, C$_3$–C$_7$ cycloalkyl, phenyl and benzyl being optionally substituted by halo, —CN, —OR$^5$, —OR$^8$, —CO$_2$R$^5$, —CONR$^5$R$^5$, —OCONR$^5$R$^5$, —NR$^5$CO$_2$R$^7$, —NR$^5$R$^5$, —NR$^8$R$^9$, —NR$^5$COR$^5$, —NR$^5$COR$^6$, —NR$^5$COR$^8$, —SO$_2$NR$^5$R$^5$, —NR$^5$CONR$^5$R$^5$, —NR$^5$SO$_2$R$^7$ or R$^6$ and R$^2$ is —Y-Z, or, R$^1$ and R$^2$, when taken together, represent unbranched C$_3$–C$_4$ alkylene, optionally wherein one methylene group of said C$_3$–C$_4$ alkylene is replaced by an oxygen atom or a nitrogen atom, said nitrogen atom being optionally substituted by R$^5$ or R$^8$, and R$^3$ is H, C$_1$–C$_6$ alkyl, C$_3$–C$_7$ cycloalkyl, phenyl, benzyl, —CN, halo, —OR$^7$, —CO$_2$R$^5$, —CONR$^5$R$^5$, —OCONR$^5$R$^5$, —NR$^5$CO$_2$R$^7$, —NR$^5$R$^5$, —NR$^5$COR$^5$, —NR$^5$CONR$^5$R$^5$, —NR$^5$SO$_2$R$^7$ or R$^6$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^7$, —NR$^5$R$^5$, —NR$^5$COR$^5$, —SO$_2$NR$^5$R$^5$, —NR$^5$CONR$^5$R$^5$NR$^5$SO$_2$R$^7$ or R$^6$, or (ii) R$^1$ and R$^3$ are each independently C$_1$–C$_6$ alkyl, C$_3$–C$_7$ cycloalkyl or halo-(C$_1$–C$_6$ alkyl), and R$^2$ is H, provided that (a) for definition (i), R$^1$ and R$^3$ are not both H, (b) for definition (i), R$^1$ and R$^3$ are not both optionally substituted phenyl, as defined therein, (c) for definition (i), when R$^1$ and R$^3$ are both methyl, R$^2$ is not phenyl or methyl, and (d) for definition (ii), R$^1$ and R$^3$ are not both methyl;

Y is a direct bond or C$_1$–C$_6$ alkylene;

Z is R$^{10}$ or, where Y is C$_1$–C$_6$ alkylene, Z is —NR$^5$COR$^{10}$, —NR$^5$CONR$^5$R$^{10}$, —NR$^5$CONR$^5$COR$^{10}$ or —NR$^5$SO$_2$R$^{10}$;

R$^4$ is dichloro-substituted phenyl;

each R$^5$ is independently either H, C$_1$–C$_6$ alkyl, C$_3$–C$_7$ cycloalkyl, fluoro-(C$_1$–C$_6$)-alkyl, phenyl or benzyl, or, when two such groups are attached to the same nitrogen atom, those two groups taken together with the nitrogen atom to which they are attached represent piperidinyl, said piperidinyl being optionally substituted by C$_1$–C$_6$ alkyl or C$_3$–C$_7$ cycloalkyl;

R⁶ is a four to six-membered, aromatic, partially unsaturated or saturated non-heterocyclic group, said non-heterocyclic group being optionally substituted by —OR⁵, —NR⁵R⁵, —CN, oxo, $C_1$–$C_6$ alkyl, $C_3$–$C_7$ cycloalkyl, —COR⁷ or halo;

R⁷ is $C_1$–$C_6$ alkyl, $C_3$–$C_7$ cycloalkyl, fluoro-($C_1$–$C_6$)-alkyl, phenyl or benzyl;

R⁸ is $C_1$–$C_6$ alkyl substituted by phenyl or pyridyl, said phenyl or pyridyl being optionally substituted by halo, —CN, —CONR⁵R⁵, —SO₂NR⁵R⁵, —NR⁵SO₂R⁷, —NR⁵R⁵, —($C_1$–$C_6$ alkylene)-NR⁵R⁵, $C_1$–$C_6$ alkyl, fluoro-($C_1$–$C_6$)-alkyl, $C_3$–$C_7$ cycloalkyl or $C_1$–$C_6$ alkoxy;

R⁹ is H, $C_1$–$C_6$ alkyl or $C_3$–$C_7$ cycloalkyl, said $C_1$–$C_6$ alkyl and $C_3$–$C_7$ cycloalkyl being optionally substituted by —OR⁵, —NR⁵R⁵, —NR⁵COR⁵, —CONR⁵R⁵ or R⁶;

R¹⁰ is (a) benzyl or C-linked R⁶, said benzyl being optionally substituted by halo, —OR⁵, —OR¹², —CN, —CO₂R⁷, —CONR⁵R⁵, —OCONR⁵R⁵, —C(=NR⁵)NR⁵OR⁵, —CONR⁵NR⁵R⁵, —OCONR⁵CO₂R⁷, —NR⁵R⁵, —NR⁵R¹², —NR⁵COR⁵, —NR⁵CO₂R⁷, —NR⁵CONR⁵R⁵, —NR⁵COCONR⁵R⁵, —NR⁵SO₂R⁷, —SO₂NR⁵R⁵ or R⁶, or (b) when R¹ and R³ are each independently $C_1$–$C_6$ alkyl, $C_3$–$C_7$ cycloalkyl or halo-($C_1$–$C_6$ alkyl), R¹⁰ is phenyl, $C_1$–$C_6$ alkyl or $C_3$–$C_7$ cycloalkyl each being optionally substituted by halo, —OR⁵, —OR¹², —CN, —CO₂R⁷, —CONR⁵R⁵, —OCONR⁵R⁵, —C(=NR⁵)NR⁵OR⁵, —CONR⁵NR⁵R⁵, —OCONR⁵CO₂R⁷, —NR⁵R⁵, —NR⁵R¹², —NR⁵COR⁵, —NR⁵CO₂R⁷, NR⁵CONR⁵R⁵, —NR⁵COCONR⁵R⁵, —NR⁵SO₂R⁷, —SO₂NR⁵R⁵ or R⁶;

X is —CH₂—, —CHR¹¹—, —CO—, —S—, —SO— or —SO₂—;

R¹¹ is $C_1$–$C_6$ alkyl, $C_3$–$C_7$ cycloalkyl, fluoro-($C_1$–$C_6$)-alkyl or $C_1$–$C_6$ alkoxy; and R¹² is $C_1$–$C_6$ alkyl substituted by R⁶, —OR⁵, —CONR⁵R⁵, —NR⁵COR⁵ or —NR⁵R⁵.

2. The method according to claim 1 wherein R¹ is $C_1$–$C_6$ alkyl, —OR⁷, —CO₂R⁵, —NR⁵CO₂R⁷, —NR⁵R⁵, —NR⁵CO—($C_1$–$C_6$ alkylene)-OR⁵ or R⁶, said $C_1$–$C_6$ alkyl being optionally substituted by —CN, —OR⁵, —OR⁸, —CO₂R⁵, —CONR⁵R⁵, —OCONR⁵R⁵, —NR⁵CO₂R⁷, —NR⁵R⁵, —NR⁸R⁹, —NR⁵COR⁵, —NR⁵COR⁶, —NR⁵COR⁸, —SO₂NR⁵R⁵, —NR⁵CONR⁵R⁵, —NR⁵SO₂R⁷ or R⁶.

3. The method according to claim 2 wherein R¹ is $C_1$–$C_6$ alkyl, —OR⁷, —CO₂R⁵, —NR⁵CO₂R⁷, —NR⁵R⁵, —NR⁵CO—($C_1$–$C_6$ alkylene)-OR⁵ or R⁶, said $C_1$–$C_6$ alkyl being optionally substituted by halo or —OR⁵.

4. The method according to claim 3 wherein R¹ is $C_1$–$C_3$ alkyl, —OCH₃, —CO₂($C_1$–$C_2$ alkyl), —NHCO₂($C_1$–$C_2$ alkyl), —NH₂, —N(CH₃)₂, —NHCOCH₂OCH₃ or furanyl, said $C_1$–$C_3$ alkyl being optionally substituted by fluoro or —OH.

5. The method according to claim 4 wherein R¹ is methyl, ethyl, prop-2-yl, hydroxymethyl, trifluoromethyl, —OCH₃, —CO₂CH₂CH₃, —NHCO₂CH₂CH₃, —NH₂, —N(CH₃)₂, —NHCOCH₂OCH₃ or furan-2-yl.

6. The method according to claim 5 wherein R¹ is ethyl.

7. The method according to claim 1 wherein R¹ is methyl, ethyl, trifluoromethyl or —CH₂NHCH₂(4-cyanophenyl).

8. The method according to claim 1 wherein R² is H, $C_1$–$C_6$ alkyl, —($C_1$–$C_3$ alkylene)-NR⁵CO—($C_1$–$C_6$ alkyl), —($C_1$–$C_3$ alkylene)-NR⁵CONR⁵—($C_1$–$C_6$ alkyl), —($C_1$–$C_3$ alkylene)-NR⁵CONR⁵CO-(phenyl), —($C_1$–$C_3$ alkylene)-NR⁵SO₂(C-linked R⁶), —($C_1$–$C_3$ alkylene)-NR⁵CO(C-linked R⁶), —($C_1$–$C_3$ alkylene)-NR⁵CO-(phenyl), each $C_1$–$C_6$ alkyl and phenyl being optionally substituted by halo, —OR⁵, —OR¹², —CN, —CO₂R⁷, —CONR⁵R⁵, —OCONR⁵R⁵, —C(=NR⁵)NR⁵OR⁵, —CONR⁵NR⁵R⁵, —OCONR⁵CO₂R⁷, —NR⁵R⁵, —NR⁵R¹², —NR⁵COR⁵, —NR⁵CO₂R⁷, NR⁵CONR⁵R⁵, —NR⁵COCONR⁵R⁵, —NR⁵SO₂R⁷, —SO₂NR⁵R⁵ or R⁶.

9. The method according to claim 8 wherein R² is H, $C_1$–$C_6$ alkyl, —($C_1$–$C_3$ alkylene)-NR⁵CO—($C_1$–$C_6$ alkyl), —($C_1$–$C_3$ alkylene)-NR⁵CONR⁵—($C_1$–$C_6$ alkyl), —($C_1$–$C_3$ alkylene)-NR⁵CONR⁵CO-(phenyl), —($C_1$–$C_3$ alkylene)-NR⁵SO₂R⁶, —($C_1$–$C_3$ alkylene)-NR⁵COR⁶, —($C_1$–$C_3$ alkylene)-NR⁵CO-(phenyl), each $C_1$–$C_6$ alkyl and phenyl being optionally substituted by halo, —OR⁵, —CN, —CO₂R⁷, —CONR⁵R⁵, —OCONR⁵R⁵, —OCONR⁵CO₂R⁷, —NR⁵R⁵, —NR⁵CONR⁵R⁵, —NR⁵COCONR⁵R⁵ or R⁶.

10. The method according to claim 9 wherein R² is H, $C_1$–$C_3$ alkyl, —($C_1$–$C_2$ alkylene)-NHCO—($C_1$–$C_3$ alkyl), —($C_1$–$C_2$ alkylene)-NHCONH—($C_1$–$C_3$ alkyl), —($C_1$–$C_2$ alkylene)-NHCONHCO-(phenyl), —($C_1$–$C_2$ alkylene)-NHSO₂R⁶, —($C_1$–$C_2$ alkylene)-NHCOR⁶, —($C_1$–$C_2$ alkylene)-NHCO-(phenyl), each $C_1$–$C_3$ alkyl and phenyl being optionally substituted by fluoro, —OH, —O($C_1$–$C_6$ alkyl), —CN, —CO₂($C_1$–$C_6$ alkyl), —CONH₂, —OCONH₂, —OCONHCO₂Ph, —NH₂, —N($C_1$–$C_6$ alkyl)₂, —NHCONH₂, —NHCOCONH₂ or R⁶.

11. The method according to claim 9 wherein R⁶ is 2,4-dihydroxypyrimidinyl, 1-methylimidazolyl, tetrahydrofuranyl, 1,5-dimethylpyrazolyl, tetrazolyl, pyridinyl, pyrimidinyl, 3-hydroxypyridazinyl, 2-hydroxypyridinyl, 2-oxo-2H-pyranyl or 1,2,3-thiadiazolyl.

12. The method according to claim 10 wherein R² is H, —CH₂OH, —CH₂CH₂OH, —CH₂CH₂CH₂OH, —CH₂OCONH₂, —CH₂CH₂OCONH₂, —CH₂OCONHCO₂Ph, —CH₂CO₂CH₂CH₃, —CH₂CH₂CO₂CH₃, —CH₂CH₂CO₂CH₂CH₃, —CH₂CH₂CONH₂, —CH₂CH₂NH₂, —CH₂CH₂CH₂NH₂, —CH₂CH₂NHCOCHF₂, —CH₂CH₂NHCOCH₂CN, —CH₂CH₂NHCOCH₂N(CH₃)₂, —CH₂CH₂NHCOCH₂OCH₃, —CH₂CH₂NHCOCH₂OH, —CH₂CH₂NHCOCH₂OCH₂CH₃, —CH₂CH₂NHCOCH₂NHCONH₂, —CH₂CH₂NHCOCONH₂, —CH₂CH₂NHCONHCH₂CH₂CH₃, —CH₂CH₂NHCONHCOPh, —CH₂CH₂NHCONHCO(2,6-difluorophenyl), —CH₂CH₂NHSO₂(2,4-dihydroxypyrimidin-5-yl), —CH₂CH₂NHSO₂(1-methylimidazol-4-yl), —CH₂CH₂NHCO(tetrahydrofuran-2-yl), —CH₂CH₂NHCO(1,5-dimethylpyrazol-3-yl), —CH₂CH₂NHCOCH₂(tetrazol-1-yl), —CH₂CH₂NHCOPh, —CH₂CH₂NHCO(pyridin-2-yl), —CH₂CH₂NHCO(pyrimidin-2-yl), —CH₂CH₂NHCO(2-fluorophenyl), —CH₂CH₂NHCO(3-hydroxyphenyl), —CH₂CH₂NHCO(3-hydroxypyridazin-6-yl), —CH₂CH₂NHCO(2-hydroxypyridin-6-yl), —CH₂CH₂NHCO(2-oxo-2H-pyran-5-yl) or —CH₂CH₂NHCO(1,2,3-thiadiazol-4-yl).

13. The method according to claim 1 wherein R² is H, methyl, —CH₂CH₂OH, —CH₂CH₂CH₂OH, —CH₂CH₂NH₂, —CH₂CH₂CH₂NH₂, —CH₂CN, —CH₂CH₂OCH₃, —CH₂CONH₂, —CH₂CH₂NHCOCH₂OCH₃ or azetidin-3-yl.

14. The method according to claim 13 wherein R² is —CH₂CH₂OH, —CH₂CH₂NH₂, —CH₂CN or azetidin-3-yl.

15. The method according to claim 1 wherein R³ is $C_1$–$C_6$ alkyl, —CO₂R⁵, —CONR⁵R⁵, —NR⁵CO₂R⁷ or —NR⁵R⁵, said $C_1$–$C_6$ alkyl being optionally substituted by halo, —CN, —OR$^5$, —CO$_2$R$^5$, —CONR$^5$R$^5$, —OCONR$^5$R$^5$, —NR$^5$CO$_2$R$^7$, —NR$^5$R$^5$, —NR$^5$COR$^5$, —SO$_2$NR$^5$R$^5$, —NR$^5$CONR$^5$R$^5$, —NR$^5$SO$_2$R$^7$ or R$^6$.

16. The method according to claim 15 wherein R$^3$ is $C_1$–$C_6$ alkyl, —CO$_2$R$^5$, —CONR$^5$R$^5$, —NR$^5$CO$_2$R$^7$ or —NR$^5$R$^5$, said $C_1$–$C_6$ alkyl being optionally substituted by halo, CN or —OR$^5$.

17. The method according to claim 16 wherein R$^3$ is $C_1$–$C_3$ alkyl, —CO$_2$($C_1$–$C_2$ alkyl), —CONH$_2$, —NHCO$_2$($C_1$–$C_4$ alkyl), —N(CH$_3$)$_2$ or —NH$_2$, said $C_1$–$C_3$ alkyl being optionally substituted by halo, —CN or —OH.

18. The method according to claim 17 wherein R$^3$ is methyl, ethyl, prop-2-yl, hydroxymethyl, cyanomethyl, trifluoromethyl, —CO$_2$CH$_2$CH$_3$, —CONH$_2$, —NHCO$_2$C(CH$_3$)$_3$, —N(CH$_3$)$_2$ or —NH$_2$.

19. The method according to claim 18 wherein R$^3$ is methyl, ethyl, prop-2-yl or trifluoromethyl.

20. The method according to claim 19 wherein R$^3$ is ethyl.

21. The method according to claim 1 wherein R$^4$ is 3,5-dichlorophenyl.

22. The method according to claim 1 wherein X is —CH$_2$—, —CHR$^{11}$—, —CO—, —S— or —SO$_2$—.

23. The method according to claim 22 wherein X is —CH$_2$—, —CH(OCH$_3$)—, —CO—, —S— or —SO$_2$—.

24. The method according to claim 23 wherein X is —CH$_2$— or —S—.

25. The method according to claim 1 wherein the compound of formula Ib is selected from the group consisting of:

2-[4-(3,5-dichlorobenzyl)-3,5-diethyl-1H-pyrazol-1-yl]ethanol;

2-[4-(3,5-dichlorobenzyl)-5-isopropyl-3-methyl-1H-pyrazol-1-yl]ethanol;

ethyl [4-(3,5-dichlorobenzyl)-3,5-diethyl-1H-pyrazol-1-yl]acetate;

N$^1$-{2-[4-(3,5-dichlorobenzyl)-3,5-diethyl-1H-pyrazol-1-yl]ethyl}ethanediamide;

2-[(aminocarbonyl)amino]-N-{2-[4-(3,5-dichlorobenzyl)-3,5-diethyl-1H-pyrazol-1-yl]ethyl}acetamide;

N-{2-[4-(3,5-dichlorobenzyl)-3,5-diethyl-1H-pyrazol-1-yl]ethyl}-2-ethoxyacetamide;

N-{2-[4-(3,5-dichlorobenzyl)-3,5-diethyl-1H-pyrazol-1-yl]ethyl}-2-methoxyacetamide;

N-{2-[4-(3,5-dichlorobenzyl)-3,5-diethyl-1H-pyrazol-1-yl]ethyl}-3-hydroxybenzamide;

N-{2-[4-(3,5-dichlorobenzyl)-3,5-diethyl-1H-pyrazol-1-yl]ethyl}-2-hydroxyacetamide;

N-{2-[4-(3,5-dichlorobenzyl)-3,5-diethyl-1H-pyrazol-1-yl]ethyl}-2-(dimethylamino)acetamide;

2-cyano-N-{2-[4-(3,5-dichlorobenzyl)-3,5-diethyl-1H-pyrazol-1-yl]ethyl}acetamide;

N-{2-[4-(3,5-dichlorobenzyl)-3,5-diethyl-1H-pyrazol-1-yl]ethyl}-2-fluorobenzamide;

N-{2-[4-(3,5-dichlorobenzyl)-3,5-diethyl-1H-pyrazol-1-yl]ethyl}-N'-propylurea;

N-benzoyl-N'-{2-[4-(3,5-dichlorobenzyl)-3,5-diethyl-1H-pyrazol-1-yl]ethyl}urea;

2-[4-(3,5-dichlorobenzyl)-3-isopropyl-5-methyl-1H-pyrazol-1-yl]ethanol;

ethyl [4-(3,5-dichlorobenzyl)-3-isopropyl-5-methyl-1H-pyrazol-1-yl]acetate;

ethyl [4-(3,5-dichlorobenzyl)-5-isopropyl-3-methyl-1H-pyrazol-1-yl]acetate;

4-(3,5-dichlorobenzyl)-3,5-diethyl-1H-pyrazole;

2-[4-(3,5-dichlorobenzyl)-3,5-dimethyl-1H-pyrazol-1-yl]ethanol;

2-[4-(3,5-dichlorobenzyl)-5-methyl-3-(trifluoromethyl)-1H-pyrazol-1-yl]ethanol;

4-(3,5-dichlorobenzyl)-3-isopropyl-5-methyl-1H-pyrazole;

2-{4-[(3,5-dichlorophenyl)sulfanyl]-3,5-dimethyl-1H-pyrazol-1-yl}ethanol;

2-{4-[(3,5-dichlorophenyl)sulfonyl]-3,5-dimethyl-1H-pyrazol-1-yl}ethanol;

4-(3,5-dichlorobenzyl)-3,5-dimethyl-1H-pyrazole;

2-[4-(3,5-dichlorobenzyl)-3,5-dimethyl-1H-pyrazol-1-yl]ethanamine;

2-[4-(3,5-dichlorobenzyl)-5-ethyl-3-(trifluoromethyl)-1H-pyrazol-1-yl]ethanol;

2-[4-(3,5-dichlorobenzyl)-3-ethyl-5-(trifluoromethyl)-1H-pyrazol-1-yl]ethanol;

2-[4-(3,5-dichlorobenzyl)-5-ethyl-3-methyl-1H-pyrazol-1-yl]ethanol;

2-[4-(3,5-dichlorobenzyl)-3-ethyl-5-methyl-1H-pyrazol-1-yl]ethanol;

2-[4-(3,5-dichlorobenzyl)-3-(dimethylamino)-5-methyl-1H-pyrazol-1-yl]ethanol;

2-[4-(3,5-dichlorobenzyl)-5-methoxy-3-methyl-1H-pyrazol-1-yl]ethanol;

2-[4-(3,5-dichlorobenzyl)-5-(2-furyl)-3-methyl-1H-pyrazol-1-yl]ethanol;

(3,5-dichlorophenyl)[3,5-diethyl-1-(2-hydroxyethyl)-1H-pyrazol-4-yl]methanone;

(±)-2-{4-[(3,5-dichlorophenyl)(methoxy)methyl]-3,5-diethyl-1H-pyrazol-1-yl}ethanol;

2-[4-(3,5-dichlorobenzyl)-3,5-diethyl-1H-pyrazol-1-yl]ethyl carbamate;

methyl 3-[4-(3,5-dichlorobenzyl)-3,5-diethyl-1H-pyrazol-1-yl]propanoate;

ethyl 3-[4-(3,5-dichlorobenzyl)-3,5-diethyl-1H-pyrazol-1-yl]propanoate;

3-[4-(3,5-dichlorobenzyl)-3,5-diethyl-1H-pyrazol-1-yl]propanamide;

3-[4-(3,5-dichlorobenzyl)-3,5-diethyl-1H-pyrazol-1-yl]-1-propanol;

[4-(3,5-dichlorobenzyl)-3,5-diethyl-1H-pyrazol-1-yl]methanol;

[4-(3,5-dichlorobenzyl)-3,5-diethyl-1H-pyrazol-1-yl]methyl carbamate;

2-[4-(3,5-dichlorobenzyl)-3,5-diethyl-1H-pyrazol-1-yl]ethanamine;

N-{2-[4-(3,5-dichlorobenzyl)-3,5-diethyl-1H-pyrazol-1-yl]ethyl}benzamide;

2-[4-[(3,5-dichlorophenyl)sulfanyl]-5-ethyl-3-(hydroxymethyl)-1H-pyrazol-1-yl]ethanol;

3-[4-(3,5-dichlorobenzyl)-3,5-diethyl-1H-pyrazol-1-yl]-1-propanamine;

2-[4-[(3,5-dichlorophenyl)sulfanyl]-3-ethyl-5-(hydroxymethyl)-1H-pyrazol-1-yl]ethanol;

N-{2-[4-(3,5-dichlorobenzyl)-3,5-diethyl-1H-pyrazol-1-yl]ethyl}-2,2-difluoroacetamide;

ethyl 4-[(3,5-dichlorophenyl)sulfanyl]-5-ethyl-1H-pyrazole-3-carboxylate;

[4-[(3,5-dichlorophenyl)sulfanyl]-5-ethyl-1-(2-hydroxyethyl)-1H-pyrazol-3-yl]acetonitrile;

[4-[(3,5-dichlorophenyl)sulfonyl]-5-ethyl-1-(2-hydroxyethyl)-1H-pyrazol-3-yl]acetonitrile;

2-{4-[(3,5-dichlorophenyl)sulfanyl]-3,5-diethyl-1H-pyrazol-1-yl}ethanol;

4-(3,5-dichlorobenzyl)-3-ethyl-1H-pyrazol-5-amine;

ethyl 4-(3,5-dichlorobenzyl)-3-ethyl-1-(2-hydroxyethyl)-1H-pyrazol-5-ylcarbamate;

N-[4-(3,5-dichlorobenzyl)-3-ethyl-1-(2-hydroxyethyl)-1H-pyrazol-5-yl]-2-methoxyacetamide;
2-[4-(3,5-dichlorobenzyl)-5-(dimethylamino)-3-ethyl-1H-pyrazol-1-yl]ethanol;
ethyl 4-(3,5-dichlorobenzyl)-1-(2-hydroxyethyl)-5-methyl-1H-pyrazole-3-carboxylate;
ethyl 4-(3,5-dichlorobenzyl)-1-(2-hydroxyethyl)-3-methyl-1H-pyrazole-5-carboxylate;
2-[3-amino-4-(3,5-dichlorobenzyl)-5-methyl-1H-pyrazol-1-yl]ethanol;
ethyl [4-(3,5-dichlorobenzyl)-5-methoxy-3-methyl-1H-pyrazol-1-yl]acetate;
2-[5-amino-4-(3,5-dichlorobenzyl)-3-ethyl-1H-pyrazol-1-yl]ethanol;
and the pharmaceutically acceptable salts and solvates thereof.

26. The method of claim 25, wherein said compound is selected from the group consisting of:
2-{4-[(3,5-dichlorophenyl)sulfanyl]-3,5-dimethyl-1H-pyrazol-1-yl}ethanol; 2-[4-[(3,5-dichlorophenyl)sulfanyl]-3-ethyl-5-(hydroxymethyl)-1H-pyrazol-1-yl]ethanol; and 2-{4-[(3,5-dichlorophenyl)sulfanyl]-3,5-diethyl-1H-pyrazol-1-yl}ethanol.

27. A method for the treatment of a disorder treatable by the inhibition of reverse transcriptase, comprising the administration of an effective amount of a compound of the formula Ib

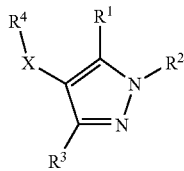

(Ib)

or a pharmaceutically acceptable salt or solvate thereof, wherein
either (i) $R^1$ is H, $C_1$–$C_6$ alkyl, $C_3$–$C_7$ cycloalkyl, phenyl, benzyl, halo, —CN, —$OR^7$, —$CO_2R^5$, —$CONR^5R^5$, —$OCONR^5R^5$, —$NR^5CO_2R^7$, —$NR^5R^5$, —$NR^5COR^5$, —$NR^5CO$—($C_1$–$C_6$ alkylene)-$OR^5$, —$NR^5CONR^5R^5$, —$NR^5SO_2R^7$ or $R^6$, said $C_1$–$C_6$ alkyl, $C_3$–$C_7$ cycloalkyl, phenyl and benzyl being optionally substituted by halo, —CN, —$OR^5$, —$OR^8$, —$CO_2R^5$, —$CONR^5R^5$, —$OCONR^5R^5$, —$NR^5CO_2R^7$, —$NR^5R^5$, —$NR^8R^9$, —$NR^5COR^5$, —$NR^5COR^6$, —$NR^5COR^8$, —$SO_2NR^5R^5$, —$NR^5CONR^5R^5$, —$NR^5SO_2R^7$ or $R^6$ and
$R^2$ is —Y-Z,
or, $R^1$ and $R^2$, when taken together, represent unbranched $C_3$–$C_4$ alkylene, optionally wherein one methylene group of said $C_3$–$C_4$ alkylene is replaced by an oxygen atom or a nitrogen atom, said nitrogen atom being optionally substituted by $R^5$ or $R^8$,
and $R^3$ is H, $C_1$–$C_6$ alkyl, $C_3$–$C_7$ cycloalkyl, phenyl, benzyl, —CN, halo, —$OR^7$, —$CO_2R^5$, —$CONR^5R^5$, —$OCONR^5R^5$, —$NR^5CO_2R^7$, —$NR^5R^5$, —$NR^5COR^5$, —$NR^5CONR^5R^5$, —$NR^5SO_2R^7$ or $R^6$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, $OCONR^5R^5$, —$NR^5CO_2R^7$, —$NR^5R^5$, —$NR^5COR^5$, —$SO_2NR^5R^5$, —$NR^5CONR^5R^5$, $NR^5SO_2R^7$ or $R^6$, or (ii) $R^1$ and $R^3$ are each independently $C_1$–$C_6$ alkyl, $C_3$–$C_7$ cycloalkyl or halo-($C_1$–$C_6$ alkyl), and $R^2$ is H, provided that
(a) for definition (i), $R^1$ and $R^3$ are not both H,
(b) for definition (i), $R^1$ and $R^3$ are not both optionally substituted phenyl, as defined therein,
(c) for definition (i), when $R^1$ and $R^3$ are both methyl, $R^2$ is not phenyl or methyl, and
(d) for definition (ii), $R^1$ and $R^3$ are not both methyl;

Y is a direct bond or $C_1$–$C_6$ alkylene;

Z is $R^{10}$ or, where Y is $C_1$–$C_3$ alkylene, Z is —$NR^5COR^{10}$, —$NR^5CONR^5R^{10}$, —$NR^5CONR^5COR^{10}$ or —$NR^5SO_2R^{10}$;

$R^4$ is dichloro-substituted phenyl;

each $R^5$ is independently either H, $C_1$–$C_6$ alkyl, $C_3$–$C_7$ cycloalkyl, fluoro-($C_1$–$C_6$)-alkyl, phenyl or benzyl, or, when two such groups are attached to the same nitrogen atom, those two groups taken together with the nitrogen atom to which they are attached represent piperidinyl said piperidinyl being optionally substituted by $C_1$–$C_6$ alkyl or $C_3$–$C_7$ cycloalkyl;

$R^6$ is a four to six-membered, aromatic, partially unsaturated or saturated non-heterocyclic group said non-heterocyclic group being optionally substituted by —$OR^5$, —$NR^5R^5$, —CN, oxo, $C_1$–$C_6$ alkyl, $C_3$–$C_7$ cycloalkyl, —$COR^7$ or halo;

$R^7$ is $C_1$–$C_6$ alkyl, $C_3$–$C_7$ cycloalkyl, fluoro-($C_1$–$C_6$)-alkyl, phenyl or benzyl;

$R^8$ is $C_1$–$C_6$ alkyl substituted by phenyl, pyridyl or pyrimidinyl, said phenyl, pyridyl and pyrimidinyl being optionally substituted by halo, —CN, —$CONR^5R^5$, —$SO_2NR^5R^5$, —$NR^5SO_2R^7$, —$NR^5R^5$, —($C_1$–$C_6$ alkylene)-$NR^5R^5$, $C_1$–$C_6$ alkyl, fluoro-($C_1$–$C_6$)-alkyl, $C_3$–$C_7$ cycloalkyl or $C_1$–$C_6$ alkoxy;

$R^9$ is H, $C_1$–$C_6$ alkyl or $C_3$–$C_7$ cycloalkyl, said $C_1$–$C_6$ alkyl and $C_3$–$C_7$ cycloalkyl being optionally substituted by —$OR^5$, —$NR^5R^5$, —$NR^5COR^5$, —$CONR^5R^5$ or $R^6$;

$R^{10}$ is (a) benzyl or C-linked $R^6$, said benzyl being optionally substituted by halo, —$OR^5$, —$OR^{12}$, —CN, —$CO_2R^7$, —$CONR^5R^5$, —$OCONR^5R^5$, —$C(=NR^5)NR^5OR^5$, —$CONR^5NR^5R^5$, —$OCONR^5CO_2R^7$, —$NR^5R^5$, —$NR^5R^{12}$, —$NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$, or (b) when $R^1$ and $R^3$ are each independently $C_1$–$C_6$ alkyl, $C_3$–$C_7$ cycloalkyl or halo-($C_1$–$C_6$ alkyl), $R^{10}$ is phenyl, $C_1$–$C_6$ alkyl or $C_3$–$C_7$ cycloalkyl each being optionally substituted by halo, —$OR^5$, —$OR^{12}$, —CN, —$CO_2R^7$, —$CONR^5R^5$, —$OCONR^5R^5$, —$C(=NR^5)NR^5OR^5$, $CONR^5NR^5R^5$, —$OCONR^5CO_2R^7$, —$NR^5R^5$, —$NR^5R^{12}$, —$NR^5COR^5$, —$NR^5CO_2R^7$, —$NR^5CONR^5R^5$, —$NR^5COCONR^5R^5$, —$NR^5SO_2R^7$, —$SO_2NR^5R^5$ or $R^6$;

X is —$CH_2$—, —$CHR^{11}$—, —CO—, —S—, —SO— or —$SO_2$—;

$R^{11}$ is $C_1$–$C_6$ alkyl, $C_3$–$C_7$ cycloalkyl, fluoro-($C_1$–$C_6$)-alkyl or $C_1$–$C_6$ alkoxy; and $R^{12}$ is $C_1$–$C_6$ alkyl substituted by $R^6$, —$OR^5$, —$CONR^5R^5$, —$NR^5COR^5$ or —$NR^5R^5$.

* * * * *